United States Patent
Ko et al.

(10) Patent No.: US 10,219,936 B2
(45) Date of Patent: Mar. 5, 2019

(54) THERAPEUTIC AGENT DELIVERY DEVICE WITH ADVANCEABLE CANNULA AND NEEDLE

(71) Applicant: ORBIT BIOMEDICAL LIMITED, London (GB)

(72) Inventors: Benjamin L. Ko, Cincinnati, OH (US); Robert H. Roth, Cincinnati, OH (US); Thomas E. Meyer, Cincinnati, OH (US); Paul D. Gordon, Shreve, OH (US); Isaac J. Khan, Bridgewater, NJ (US); Daniel W. Price, Loveland, OH (US); Brendan J. Oberkircher, Cincinnati, OH (US)

(73) Assignee: ORBIT BIOMEDICAL LIMITED, London (GB)

( * ) Notice: Subject to any disclaimer, the term of this patent is extended or adjusted under 35 U.S.C. 154(b) by 554 days.

(21) Appl. No.: 14/840,676

(22) Filed: Aug. 31, 2015

(65) Prior Publication Data
US 2016/0074211 A1    Mar. 17, 2016

Related U.S. Application Data

(60) Provisional application No. 62/049,135, filed on Sep. 11, 2014.

(51) Int. Cl.
*A61F 9/00* (2006.01)
*A61B 17/34* (2006.01)
*A61F 9/007* (2006.01)

(52) U.S. Cl.
CPC ........ *A61F 9/0008* (2013.01); *A61B 17/3421* (2013.01); *A61B 17/3478* (2013.01); *A61F 9/007* (2013.01); *A61M 2210/0612* (2013.01)

(58) Field of Classification Search
CPC .... A61F 9/0008; A61F 9/007; A61F 9/00781; A61B 17/3421; A61B 17/3438; A61M 2210/0612
See application file for complete search history.

(56) References Cited

U.S. PATENT DOCUMENTS

| 6,368,315 B1 | 4/2002 | Gillis et al. |
| 6,585,694 B1 * | 7/2003 | Smith ............... A61M 25/0084 600/563 |

(Continued)

FOREIGN PATENT DOCUMENTS

WO    WO 2017/042584 A1    3/2017

OTHER PUBLICATIONS

International Search Report and Written Opinion dated Dec. 3, 2015 for Application No. PCT/US2015/049432, 12 pgs.
U.S. Appl. No. 62/049,135, filed Sep. 11, 2014.

*Primary Examiner* — Nathan R Price
*Assistant Examiner* — John A Doubrava
(74) *Attorney, Agent, or Firm* — Frost Brown Todd LLC

(57) ABSTRACT

An apparatus for delivering therapeutic agent to an eye comprises a body, a cannula, a hollow needle, a cannula actuation assembly, and a needle actuation assembly. The cannula extends distally from the body and is sized and configured to be insertable between a choroid and a sclera of a patient's eye. The cannula actuation assembly is operable to actuate the cannula relative to the body. The needle actuation assembly is operable to actuate the needle relative to the cannula. The cannula may be inserted through a sclerotomy to position a distal end of the cannula at a posterior region of the eye, between the choroid and sclera. The needle may be advanced through the choroid to deliver the therapeutic agent adjacent to the potential space between (Continued)

the neurosensory retina and the retinal pigment epithelium layer, adjacent to the area of geographic atrophy.

20 Claims, 64 Drawing Sheets

(56) References Cited

U.S. PATENT DOCUMENTS

| | | | |
|---|---|---|---|
| 6,824,532 B2 | 11/2004 | Gillis et al. | |
| 7,189,245 B2 | 3/2007 | Kaplan | |
| 7,207,980 B2 | 4/2007 | Christian et al. | |
| 7,413,734 B2 | 8/2008 | Mistry et al. | |
| 8,197,435 B2 | 6/2012 | Prausnitz et al. | |
| 8,287,494 B2 | 10/2012 | Ma | |
| 8,425,473 B2 | 4/2013 | Ho et al. | |
| 9,408,746 B2 | 8/2016 | Lerner et al. | |
| 2004/0199130 A1* | 10/2004 | Chornenky | A61K 31/205 604/289 |
| 2005/0143363 A1 | 6/2005 | de Juan et al. | |
| 2005/0266047 A1* | 12/2005 | Tu | A61F 9/00781 424/427 |
| 2007/0191863 A1* | 8/2007 | De Juan, Jr. | A61F 9/0017 606/108 |
| 2008/0058704 A1 | 3/2008 | Hee et al. | |
| 2008/0281292 A1* | 11/2008 | Hickingbotham | A61F 9/0017 604/521 |
| 2009/0182421 A1* | 7/2009 | Silvestrini | A61F 9/00781 623/6.13 |
| 2009/0227934 A1* | 9/2009 | Euteneuer | A61F 9/00781 604/8 |
| 2012/0191064 A1 | 7/2012 | Conston et al. | |
| 2012/0197175 A1 | 8/2012 | Horvath et al. | |
| 2012/0271272 A1 | 10/2012 | Hammack et al. | |
| 2013/0216623 A1 | 8/2013 | Yamamoto et al. | |
| 2013/0245600 A1 | 9/2013 | Yamamoto et al. | |
| 2013/0253438 A1* | 9/2013 | Badawi | A61F 9/0017 604/239 |
| 2015/0209180 A1 | 7/2015 | Prausnitz et al. | |
| 2015/0223977 A1 | 8/2015 | Oberkircher et al. | |
| 2015/0258120 A1 | 9/2015 | Zarnitsyn et al. | |
| 2017/0095369 A1 | 4/2017 | Andino et al. | |
| 2017/0252209 A1* | 9/2017 | Gooi | A61M 5/19 |
| 2017/0333416 A1 | 11/2017 | Zarnitsyn et al. | |
| 2018/0042765 A1 | 2/2018 | Noronha et al. | |

* cited by examiner

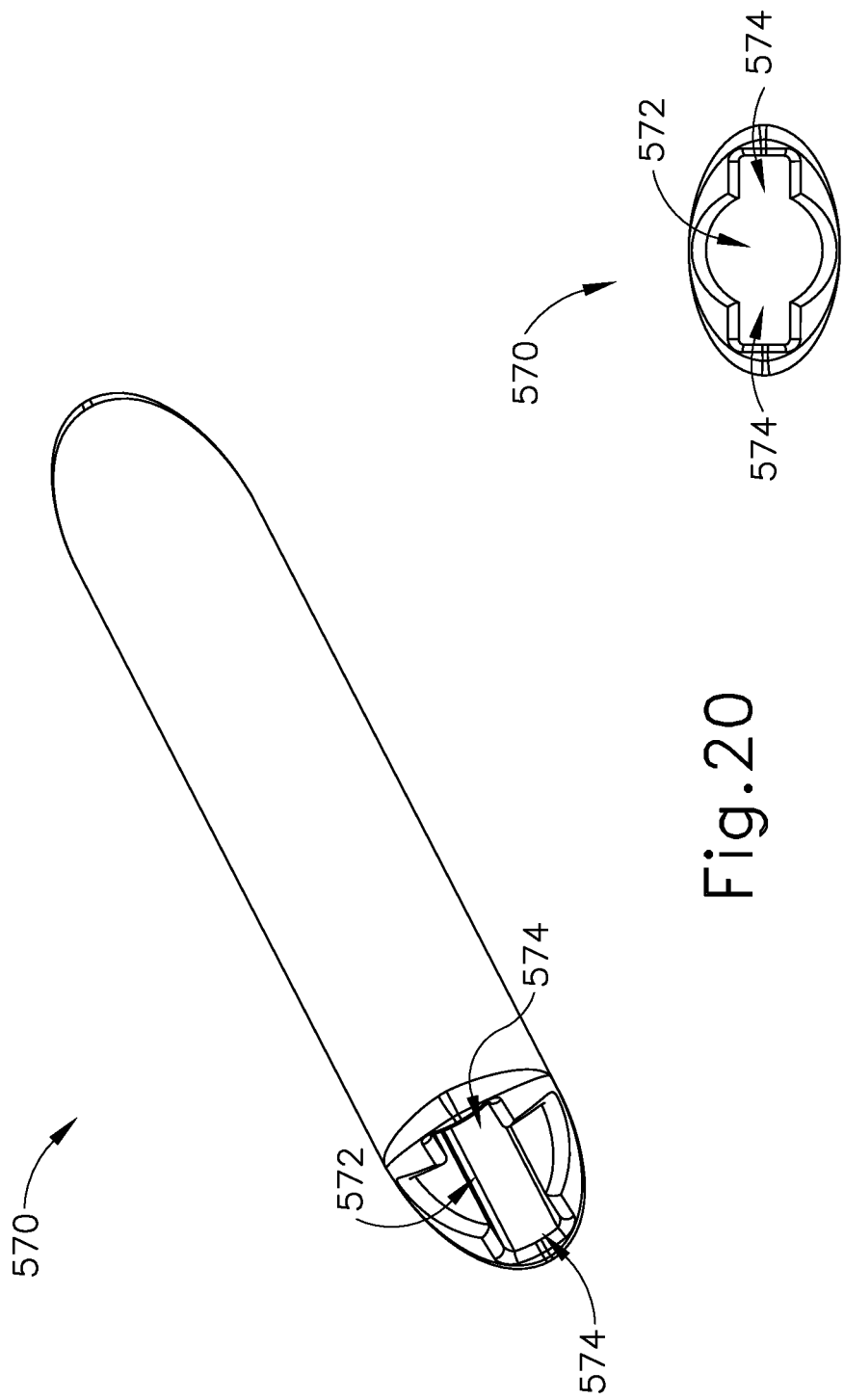

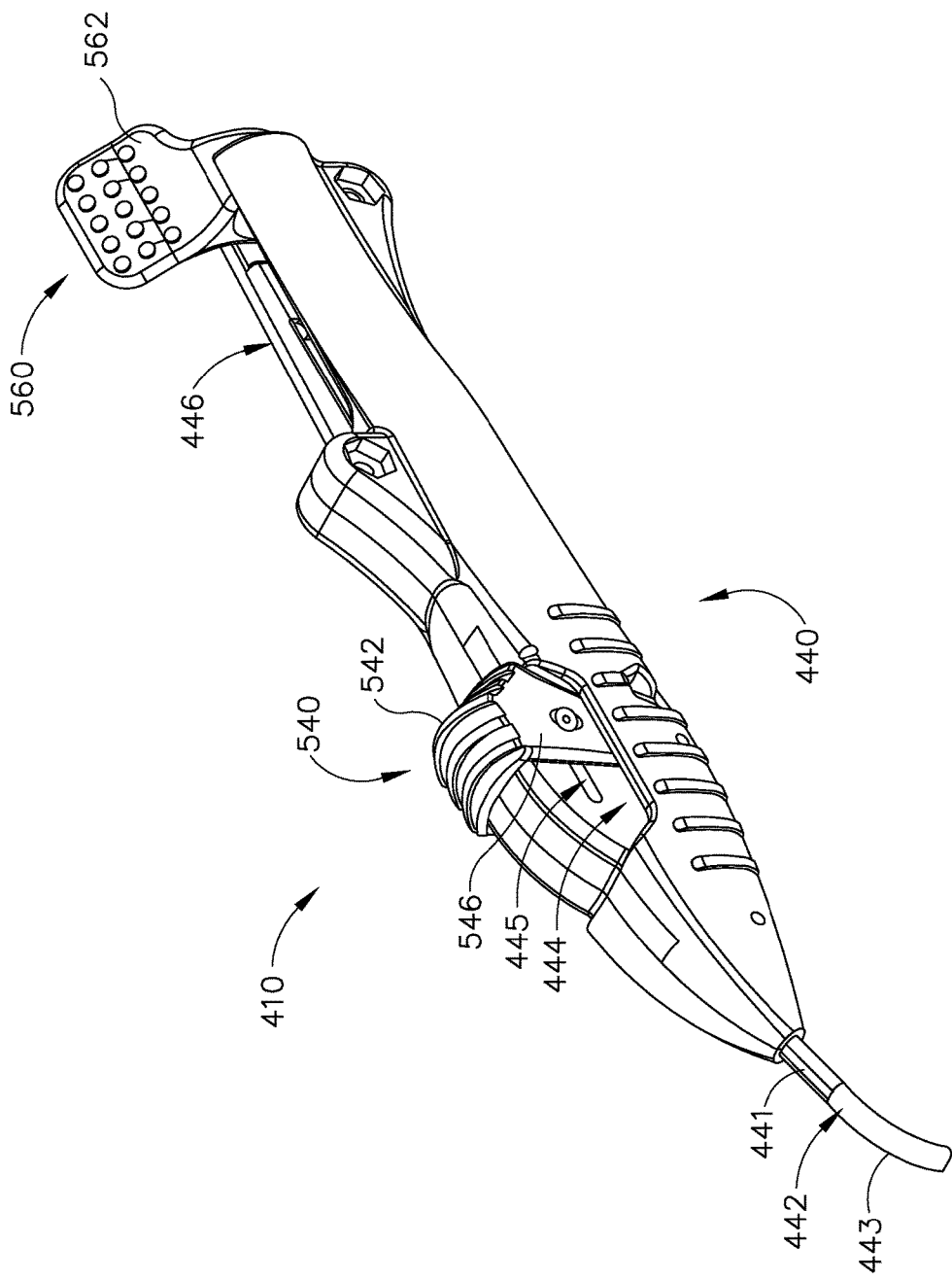

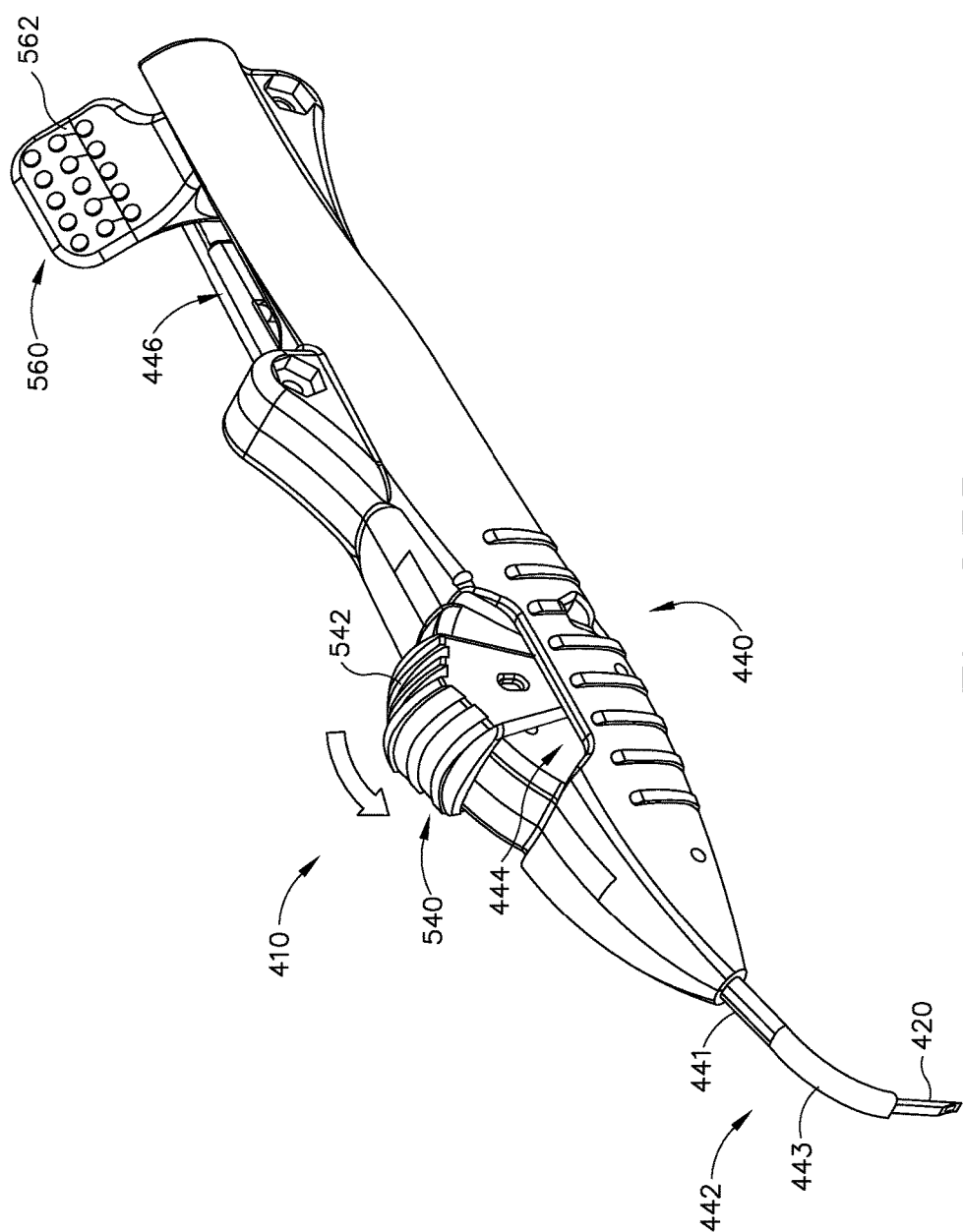

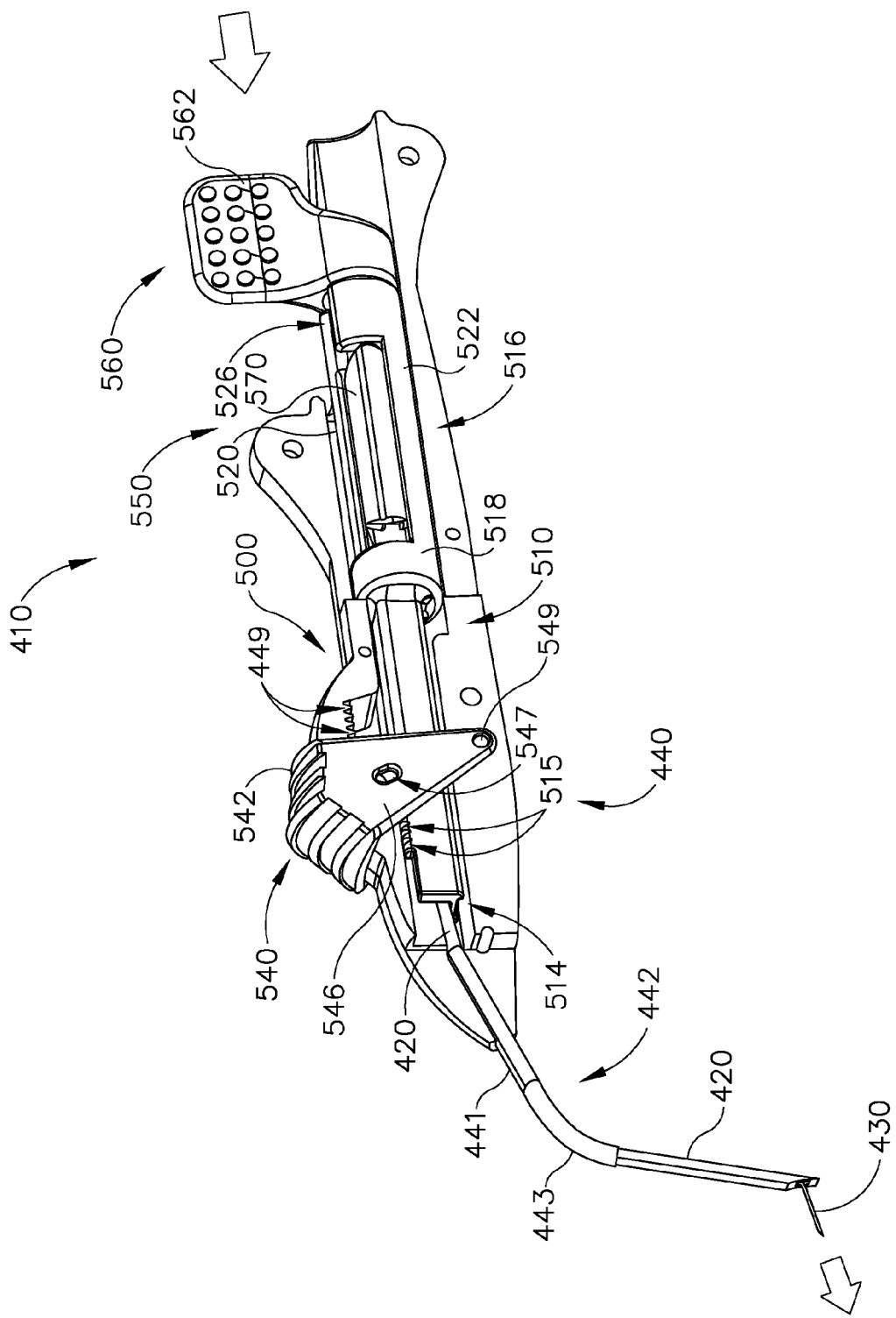

ND NEEDLE

THERAPEUTIC AGENT DELIVERY DEVICE WITH ADVANCEABLE CANNULA AND NEEDLE

PRIORITY

This application claims priority to U.S. Provisional Patent Application No. 62/049,135, entitled "Suprachoroidal Cannula Advancement Injector," filed Sep. 11, 2014, the disclosure of which is incorporated by reference herein.

JOINT RESEARCH STATEMENT

Subject matter disclosed in this application was developed and the claimed invention was made by, or on behalf of, one or more parties to a joint research agreement that was in effect on or before the effective filing date of the claimed invention. The claimed invention was made as a result of activities undertaken within the scope of the joint research agreement. The parties to the joint research agreement include Ethicon Endo-Surgery, Inc. and Janssen Research & Development, LLC.

BACKGROUND

The human eye comprises several layers. The white outer layer is the sclera, which surrounds the choroid layer. The retina is interior to the choroid layer. The sclera contains collagen and elastic fiber, providing protection to the choroid and retina. The choroid layer includes vasculature providing oxygen and nourishment to the retina. The retina comprises light sensitive tissue, including rods and cones. The macula is located at the center of the retina at the back of the eye, generally centered on an axis passing through the centers of the lens and cornea of the eye (i.e., the optic axis). The macula provides central vision, particularly through cone cells.

Macular degeneration is a medical condition that affects the macula, such that people suffering from macular degeneration may experience lost or degraded central vision while retaining some degree of peripheral vision. Macular degeneration may be caused by various factors such as age (also known as "AMD") and genetics. Macular degeneration may occur in a "dry" (nonexudative) form, where cellular debris known as drusen accumulates between the retina and the choroid, resulting in an area of geographic atrophy. Macular degeneration may also occur in a "wet" (exudative) form, where blood vessels grow up from the choroid behind the retina. Even though people having macular degeneration may retain some degree of peripheral vision, the loss of central vision may have a significant negative impact on the quality of life. Moreover, the quality of the remaining peripheral vision may be degraded and in some cases may disappear as well. It may therefore be desirable to provide treatment for macular degeneration in order to prevent or reverse the loss of vision caused by macular degeneration. In some cases it may be desirable to provide such treatment in a highly localized fashion, such as by delivering a therapeutic substance in the subretinal layer (under the neurosensory layer of the retina and above the retinal pigment epithelium) directly adjacent to the area of geographic atrophy, near the macula. However, since the macula is at the back of the eye and underneath the delicate layer of the retina, it may be difficult to access the macula in a practical fashion.

While a variety of surgical methods and instruments have been made and used to treat an eye, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 20 depicts a perspective view of a cam lock of the instrument of FIG. 12;

FIG. 21 depicts a front elevational view of the cam lock of FIG. 20;

FIG. 23A depicts another perspective view of the instrument of FIG. 12, with a cannula and a needle in a retracted position;

FIG. 23B depicts still another perspective view of the instrument of FIG. 12, with the cannula partially advanced and the needle locked and retracted;

FIG. 24E depicts yet another perspective view of the instrument of FIG. 12, with a housing of the instrument removed and the cannula and the needle in an advanced position;

Figure 1:
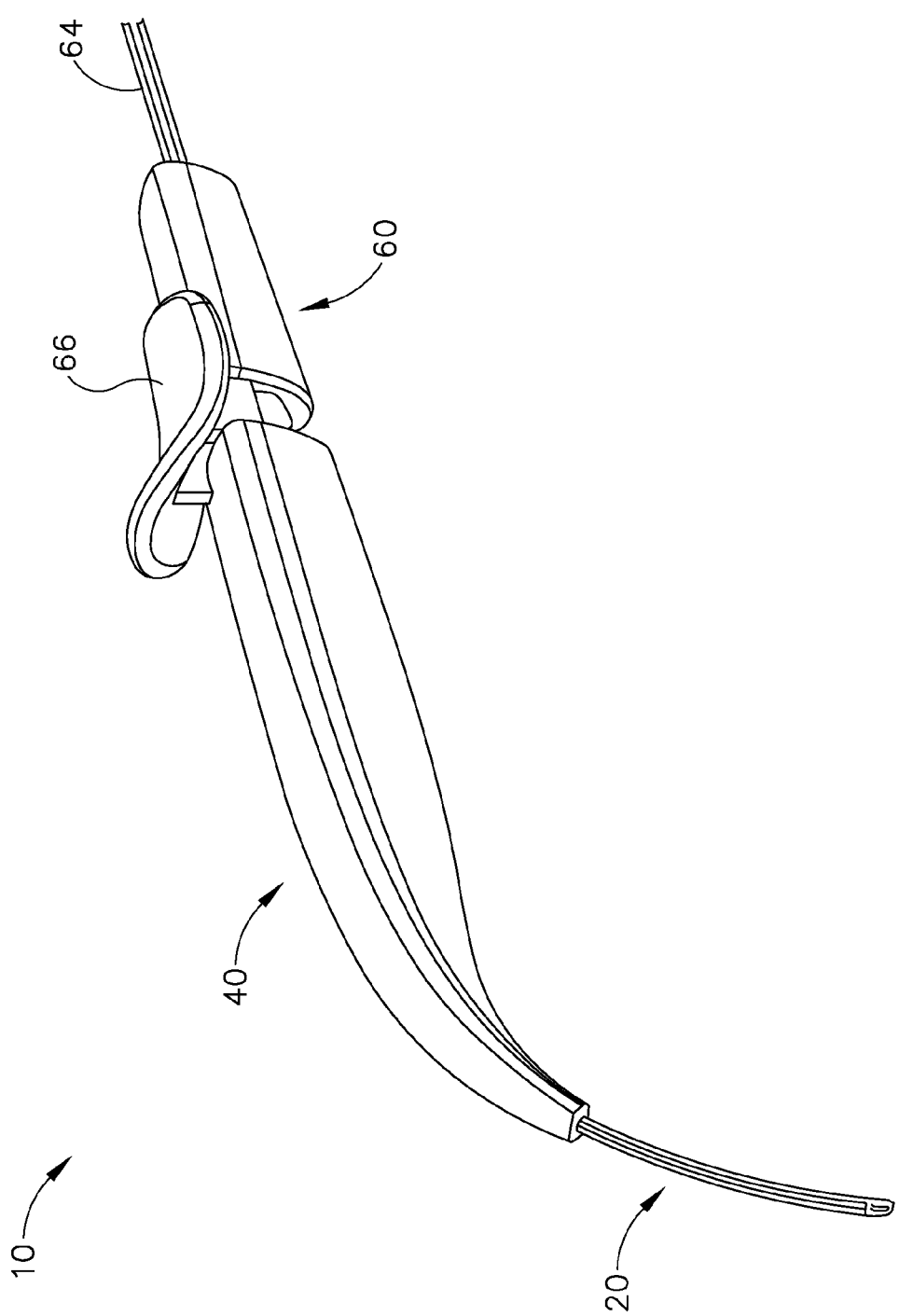
FIG. 1 depicts a perspective view of an exemplary instrument for subretinal administration of a therapeutic agent from a suprachoroidal approach.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Instrument with Slider Articulation Feature

FIGS. 1-4 show an exemplary instrument (10) that is configured for use in a procedure for the subretinal administration of therapeutic agent to an eye of a patient from a suprachoroidal approach. Instrument (10) comprises a flexible cannula (20), a body (40), and a slidable actuation assembly (60). Cannula (20) extends distally from body (40) and has a generally rectangular cross section. Cannula (20) is generally configured to support a needle (30) that is slidable within cannula (20), as will be described in greater detail below.

In the present example, cannula (20) comprises a flexible material such as Polyether block amide (PEBA), which may be manufactured under the trade name PEBAX. Of course, any other suitable material or combination of materials may be used. Also in the present example, cannula (20) has a cross-sectional profile dimension of approximately 2.0 mm by 0.8 mm, with a length of approximately 80 mm. Alternatively, any other suitable dimensions may be used.

As will be described in greater detail below, cannula (20) is flexible enough to conform to specific structures and contours of the patient's eye, yet cannula (20) has sufficient column strength to permit advancement of cannula (20) between the sclera and choroid of patient's eye without buckling. Several factors may contribute to suitable flexibility of cannula (20). For instance, the durometer of the material used to construct cannula (20) at least partially characterizes the flexibility of cannula (20). By way of example only, the material that is used to form cannula (20) may have a shore hardness of approximately 27 D, approximately 33 D, approximately 42 D, approximately 46 D, or any other suitable shore hardness. It should be understood that the shore hardness may fall within the range of approximately 27 D to approximately 46 D; or more particularly within the range of approximately 33 D to approximately 46 D; or more particularly within the range of approximately 40 D to approximately 45 D. The particular cross-sectional shape of cannula (20) may also at least partially characterize the flexibility of cannula (20). Additionally, the stiffness of needle (30) disposed within cannula (20) may at least partially characterize the flexibility of cannula (20).

In the present example, the flexibility of cannula (20) may be quantified by calculating a flexural stiffness for cannula (20). Flexural stiffness is calculated by the product of the elastic modulus and the area moment of inertia. By way of example only, one exemplary material that may be used to form cannula (20) may have a shore hardness of D27, an elastic modulus (E) of $1.2 \times 10^7$ N/m$^2$, and an area moment of inertia ($I_x$) of $5.52 \times 10^{-14}$ m$^4$, providing a calculated flexural stiffness about the x-axis at $0.7 \times 10^{-6}$ Nm$^2$. Another exemplary material that may be used to form cannula (20) may have a shore hardness of D33, an elastic modulus (E) of $2.1 \times 10^7$ N/m$^2$, and an area moment of inertia ($I_x$) of $5.52 \times 10^{-14}$ m$^4$, providing a calculated flexural stiffness about the x-axis at $1.2 \times 10^{-6}$ Nm$^2$. Another exemplary material that may be used to form cannula (20) may have a shore hardness of D42, an elastic modulus (E) of $7.7 \times 10^7$ N/m$^2$, and an area moment of inertia ($I_x$) of $5.52 \times 10^{-14}$ m$^4$, providing a calculated flexural stiffness about the x-axis at $4.3 \times 10^{-6}$ Nm$^2$. Another exemplary material that may be used to form cannula (20) may have a shore hardness of D46, an elastic modulus (E) of $17.0 \times 10^7$ N/m$^2$, and an area moment of inertia ($I_x$) of $5.52 \times 10^{-14}$ m$^4$, providing a calculated flexural stiffness about the x-axis at $9.4 \times 10^{-6}$ Nm$^2$. Thus, by way of example only, the flexural stiffness of cannula (20) may fall within the range of approximately $0.7 \times 10^{-6}$ Nm$^2$ to approximately $9.4 \times 10^{-6}$ Nm$^2$; or more particularly within the range of approximately $1.2 \times 10^{-6}$ Nm$^2$ to approximately $9.4 \times 10^{-6}$ Nm$^2$; or more particularly within the range of approximately $2.0 \times 10^{-6}$ Nm$^2$ to approximately $7.5 \times 10^{-6}$ Nm$^2$; or more particularly within the range of approximately $2.0 \times 10^{-6}$ Nm$^2$ to approximately $6.0 \times 10^{-6}$ Nm$^2$; or more particularly within the range of approximately $3.0 \times 10^{-6}$ Nm$^2$ to approximately $5.0 \times 10^{-6}$ Nm$^2$; or more particularly within the range of approximately $4.0 \times 10^{-6}$ Nm$^2$ to approximately $5.0 \times 10^{-6}$ Nm$^2$.

In the present example, the flexibility of cannula (20) may also be quantified by the following formula:

$$\delta = \frac{FL^3}{48EI} \tag{1}$$

In the above equation, flexural stiffness (EI) is calculated experimentally by deflecting cannula (20) having a fixed span (L) a set distance to yield a predetermined amount of deflection (δ). The amount of force (F) required for such a deflection may then be recorded. For instance, when using such a method cannula (20) may have a span of 0.06 m and may be deflected for a given distance. By way of example only, one exemplary material that may be used to form cannula (20) may require a force of 0.0188 N to achieve a deflection of 0.0155 m, providing a calculated flexural stiffness about the x-axis of $5.5 \times 10^{-6}$ $Nm^2$. In another exemplary material that may be used to form cannula (20) may require a force of 0.0205 N to achieve a deflection of 0.0135 m, providing a calculated flexural stiffness about the x-axis of $6.8 \times 10^{-6}$ $Nm^2$. In still another exemplary material that may be used to form cannula (20) may require a force of 0.0199 N to achieve a deflection of 0.0099 m, providing a calculated flexural stiffness about the x-axis of $9.1 \times 10^{-6}$ $Nm^2$. In yet another exemplary material that may be used to form cannula (20) may require a force of 0.0241 N to achieve a deflection of 0.0061 m, providing a calculated flexural stiffness about the x-axis of $1.8 \times 10^{-6}$ $Nm^2$. In yet another exemplary material that may be used to form cannula (20) may require a force of 0.0190 N to achieve a deflection 0.0081 m, providing a calculated flexural stiffness about the x-axis of $1.0 \times 10^{-6}$ $Nm^2$. In yet another exemplary material that may be used to form cannula (20) may require a force of 0.0215 N to achieve a deflection of 0.0114 m, providing a calculated flexural stiffness about the x-axis of $8.4 \times 10^{-6}$ $Nm^2$. In yet another exemplary material that may be used to form cannula (20) may require a force of 0.0193 N to achieve a deflection of 0.0170 m, providing a calculated flexural stiffness about the x-axis of $5.1 \times 10^{-6}$ $Nm^2$. In yet another exemplary material that may be used to form cannula (20) may require a force of 0.0224 N to achieve a deflection of 0.0152 m, providing a calculated flexural stiffness about the x-axis of $6.6 \times 10^{-6}$ $Nm^2$. In yet another exemplary material that may be used to form cannula (20) may require a force of 0.0183 N to achieve a deflection of 0.0119 m, providing a calculated flexural stiffness about the x-axis of $6.9 \times 10^{-6}$ $Nm^2$. In yet another exemplary material that may be used to form cannula (20) may require a force of 0.0233 N to achieve a deflection of 0.0147 m, providing a calculated flexural stiffness about the x-axis of $7.1 \times 10^{-6}$ $Nm^2$. In yet another exemplary material that may be used to form cannula (20) may require a force of 0.0192 N to achieve a deflection of 0.0122, providing a calculated flexural stiffness about the x-axis of $7.1 \times 10^{-6}$ $Nm^2$. In yet another exemplary material that may be used to form cannula (20) may require a force of 0.0201 N to achieve a deflection of 0.0201, providing a calculated flexural stiffness about the x-axis of $4.5 \times 10^{-6}$ $Nm^2$. Thus, by way of example only, the flexural stiffness of cannula (20) may fall within the range of approximately $1.0 \times 10^{-6}$ $Nm^2$ to approximately $9.1 \times 10^{-6}$ $Nm^2$. It should be understood that in other examples, the flexural stiffness of cannula may fall within the range of approximately $0.7 \times 10^{-6}$ $Nm^2$ to approximately $11.1 \times 10^{-6}$ $Nm^2$; or more particularly within the range of approximately $2.0 \times 10^{-6}$ $Nm^2$ to approximately $6.0 \times 10^{-6}$ $Nm^2$.

Needle (30) may have a flexural stiffness that differs from the flexural stiffness of cannula (20). By way of example only, needle (30) may be formed of a nitinol material that has an elastic modulus (E) of $7.9 \times 10^{10}$ $N/m^2$, and an area moment of inertia ($I_x$) of $2.12 \times 10^{-17}$ $m^4$, providing a calculated flexural stiffness about the x-axis at $1.7 \times 10^{-6}$ $Nm^2$. By way of further example only, the flexural stiffness of needle (30) may fall within the range of approximately $0.5 \times 10^{-6}$ $Nm^2$ to approximately $2.5 \times 10^{-6}$ $Nm^2$; or more particularly within the range of approximately $0.75 \times 10^{-6}$ $Nm^2$ to approximately $2.0 \times 10^{-6}$ $Nm^2$; or more particularly within the range of approximately $1.25 \times 10^{-6}$ $Nm^2$ to approximately $1.75 \times 10^{-6}$ $Nm^2$.

Figure 5:
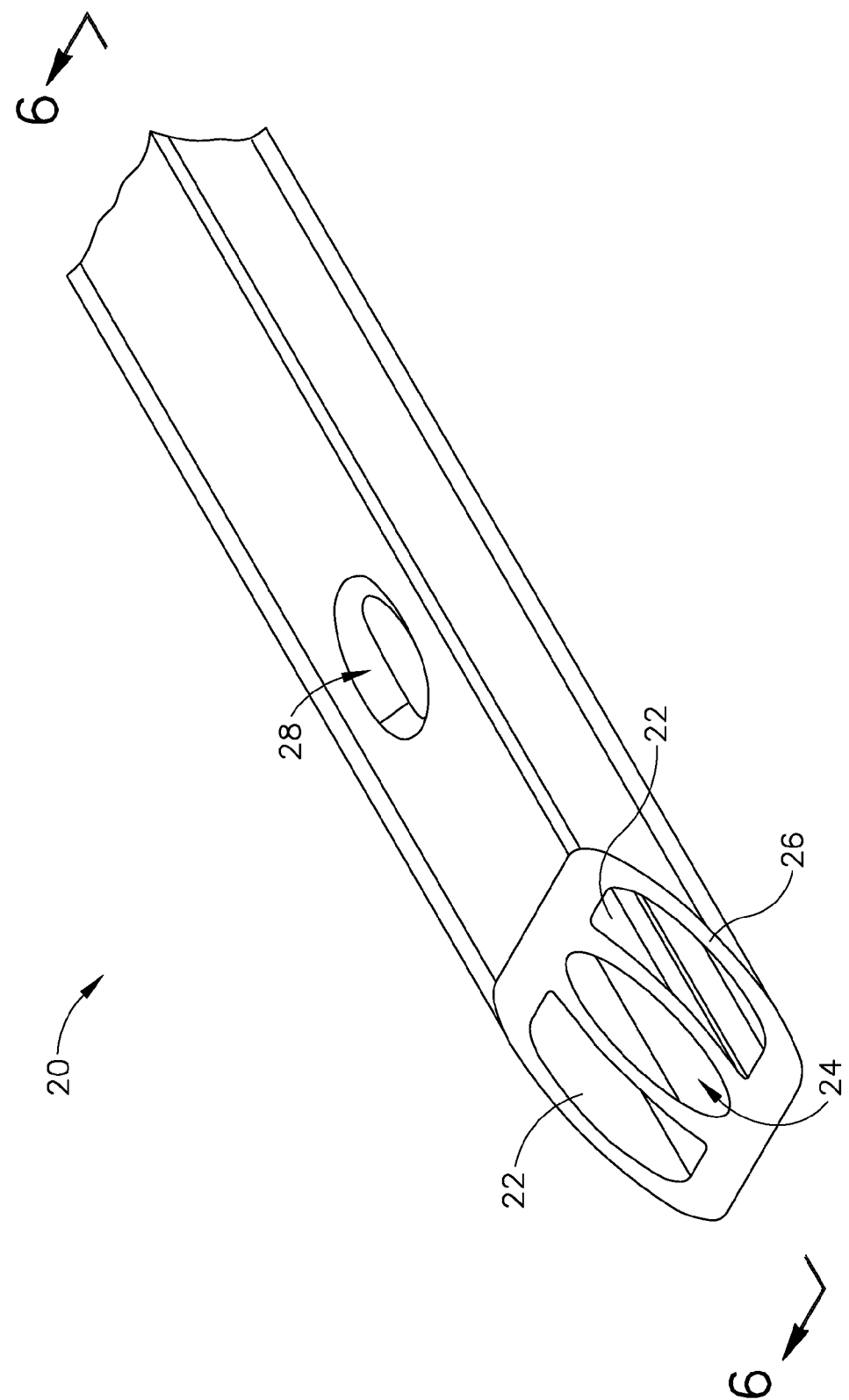
FIG. 5 depicts a perspective view of the distal end of an exemplary cannula that may be incorporated into the instrument of FIG. 1.
Figure 6:
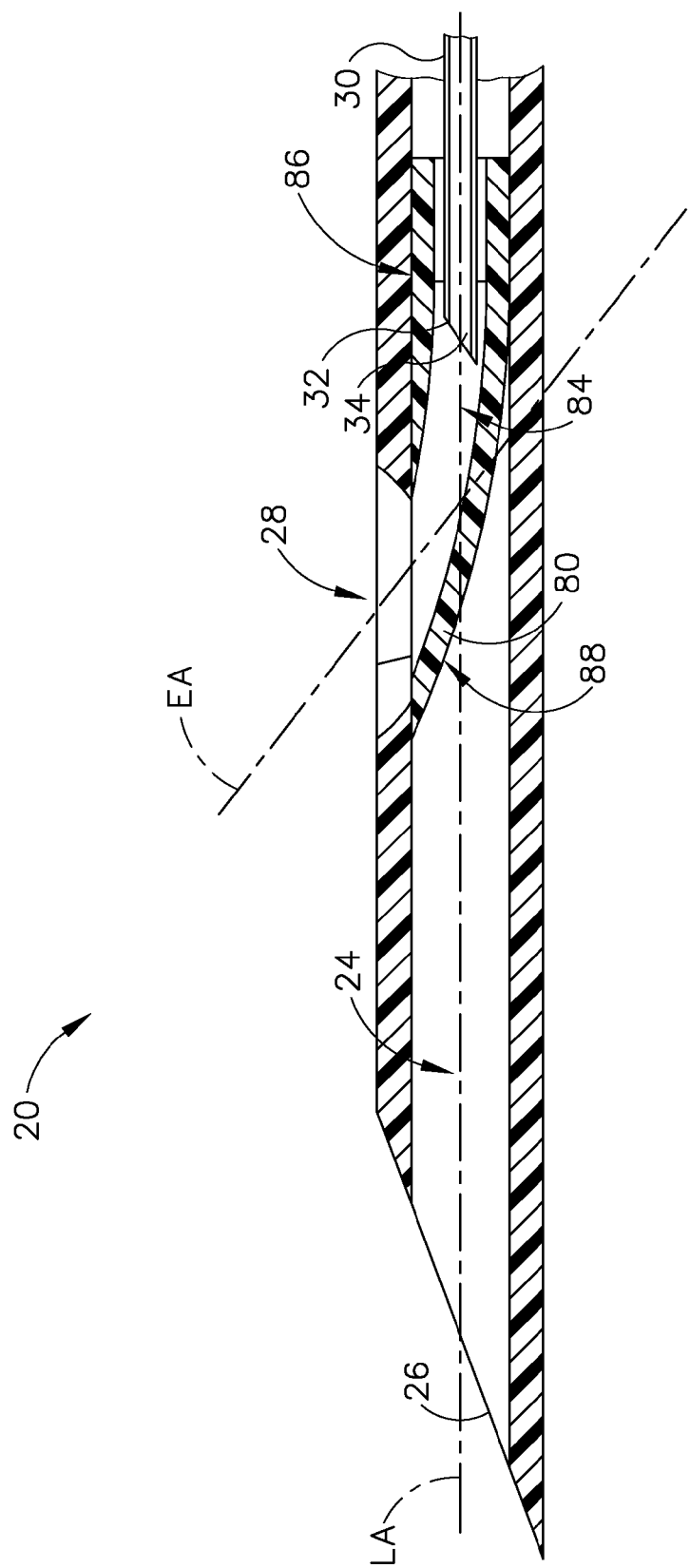
FIG. 6 depicts a cross-sectional view of the cannula of FIG. 5, with the cross-section taken along line 6-6 of FIG. 5.

As can be seen in FIGS. 5 and 6, cannula (20) comprises two side lumens (22) and a single central lumen (24) extending longitudinally through cannula (20) and terminating at an atraumatic, beveled distal end (26). A beveled lateral opening (28) is located proximal to beveled distal end (26). Side lumens (22) contribute to the flexibility of cannula (20). Although lumens (22, 24) are shown as being open at beveled distal end (26), it should be understood that in some examples, side lumens (22, 24) may be optionally closed at beveled distal end (26). As will be described in greater detail below, central lumen (24) is configured to receive needle (30) and a needle guide (80). In some versions, an optical fiber (not shown) is also disposed in central lumen (24) alongside needle (30). Such an optical fiber may be used to provide illumination and/or optical feedback.

Beveled distal end (26) is generally beveled to provide separation between the sclera and choroid layers to enable cannula (20) to be advanced between such layers while not inflicting trauma to the sclera or choroid layers. In the present example, beveled distal end (26) is beveled at an angle of approximately 15° relative to the longitudinal axis of cannula (20) in the present example. In other examples, beveled distal end (26) may have a bevel angle within the range of approximately 5° to approximately 50°; or more particularly within the range of approximately 5° to approximately 40°; or more particularly within the range of approximately 10° to approximately 30°; or more particularly within the range of approximately 10° to approximately 20°. Of course, distal end (26) may have any other suitable configuration. By way of example only, distal end (26) may be rounded instead of being beveled.

A needle guide (80) is disposed within lumen (24) such that the distal end of needle guide (80) abuts beveled lateral opening (28). Needle guide (80) is generally configured to direct needle (30) upwardly along an exit axis (EA) that is obliquely oriented relative to the longitudinal axis (LA) of cannula (20) through beveled opening (28) of cannula (20). Needle guide (80) may be formed of plastic, stainless steel, and/or any other suitable biocompatible material(s). The shape of needle guide (80) is configured for insertion into central lumen (24). In the present example, needle guide (80) is secured within central lumen (24) by a press or interference fit, although in other examples, adhesives and/or mechanical locking mechanisms may be used to secure needle guide (80).

As can best be seen in FIG. 6, needle guide (80) defines an internal lumen (84) that is configured to slidably receive needle (30). In particular, internal lumen (84) includes a generally straight proximal portion (86) and a curved distal portion (88). Straight proximal portion (86) corresponds to the longitudinal axis (LA) of cannula (20), while curved distal portion (88) curves upwardly away from the longitudinal axis of cannula (20). Curved distal portion (88) of the present example is curved to direct needle (30) along an exit axis (EA) that extends distally from cannula (20) at an angle of approximately 7° to approximately 9° relative to the longitudinal axis (LA) of cannula (20). It should be understood that such an angle may be desirable to deflect needle (30) in a direction to ensure penetration of needle into the choroid (306) and to minimize the possibility of needle (30) continuing beneath the choroid (306) through the suprachoroidal space (as opposed to penetrating through the choroid (306)) and the possibility of retinal perforation. By way of further example only, curved distal portion (88) may urge needle (30) to exit cannula (20) along an exit axis (EA) that is oriented at an angle within the range of approximately 5° to approximately 30° relative to the longitudinal axis (LA) of cannula (20); or more particularly within the range of approximately 5° to approximately 20° relative to the longitudinal axis (LA) of cannula (20); or more particularly within the range of approximately 5° to approximately 10° relative to the longitudinal axis (LA) of cannula (20).

Needle (30) is in the form of an inner cannula that has a sharp distal end (32) and defines an internal lumen (34). Distal end (32) of the present example has a lancet configuration. In some other versions, distal end (32) has a tri-bevel configuration or any other configuration as described in U.S. patent application Ser. No. 14/619,256, entitled "Method and Apparatus for Suprachoroidal Administration of Therapeutic Agent," filed Feb. 11, 2015, the disclosure of which is incorporated by reference herein. Still other suitable forms that distal end (32) may take will be apparent to those of ordinary skill in the art in view of the teachings herein. Needle (30) of the present example comprises a stainless steel hypodermic needle that is sized to deliver the therapeutic agent while being small enough to minimize incidental trauma as needle (30) penetrates tissue structures of the patient's eye, as will be described in greater detail below. By way of example only, needle (30) may be 35 gauge with a 100 µm inner diameter, although other suitable sizes may be used. For instance, the outer diameter of needle (30) may fall within the range of 27 gauge to 45 gauge; or more particularly within the range of 30 gauge to 42 gauge; or more particularly within the range of 32 gauge to 39 gauge. As another merely illustrative example, the inner diameter of needle (30) may fall within the range of approximately 50 µm to approximately 200 µm; or more particularly within the range of approximately 50 µm to approximately 150 µm; or more particularly within the range of approximately 75 µm to approximately 125 µm.

Referring back to FIGS. 1-2, body (40) is generally shaped as an elongate rectangle with a curved distal end. The particular shape of body (40) that is shown is configured to be grasped by an operator. Alternatively, body (40) may be mounted on a support device or robotic arm for ease of positioning instrument (10), as described in U.S. patent application Ser. No. 14/619,256, entitled "Method and Apparatus for Suprachoroidal Administration of Therapeutic Agent," filed Feb. 11, 2015, the disclosure of which is incorporated by reference herein.

Actuation assembly (60) includes an actuation member (62) and a locking member (66). Locking member (66) is removably attachable to body engagement portion (50), between body (40) and actuation member (62). As will be described in greater detail below, locking member (66) fills a space between body (40) and actuation member (62) to prevent actuation member (62) from being advanced distally relative to body (40). However, locking member (66) can be removed to selectively permit actuation member (62) to be advanced distally relative to body (40).

Figure 2:
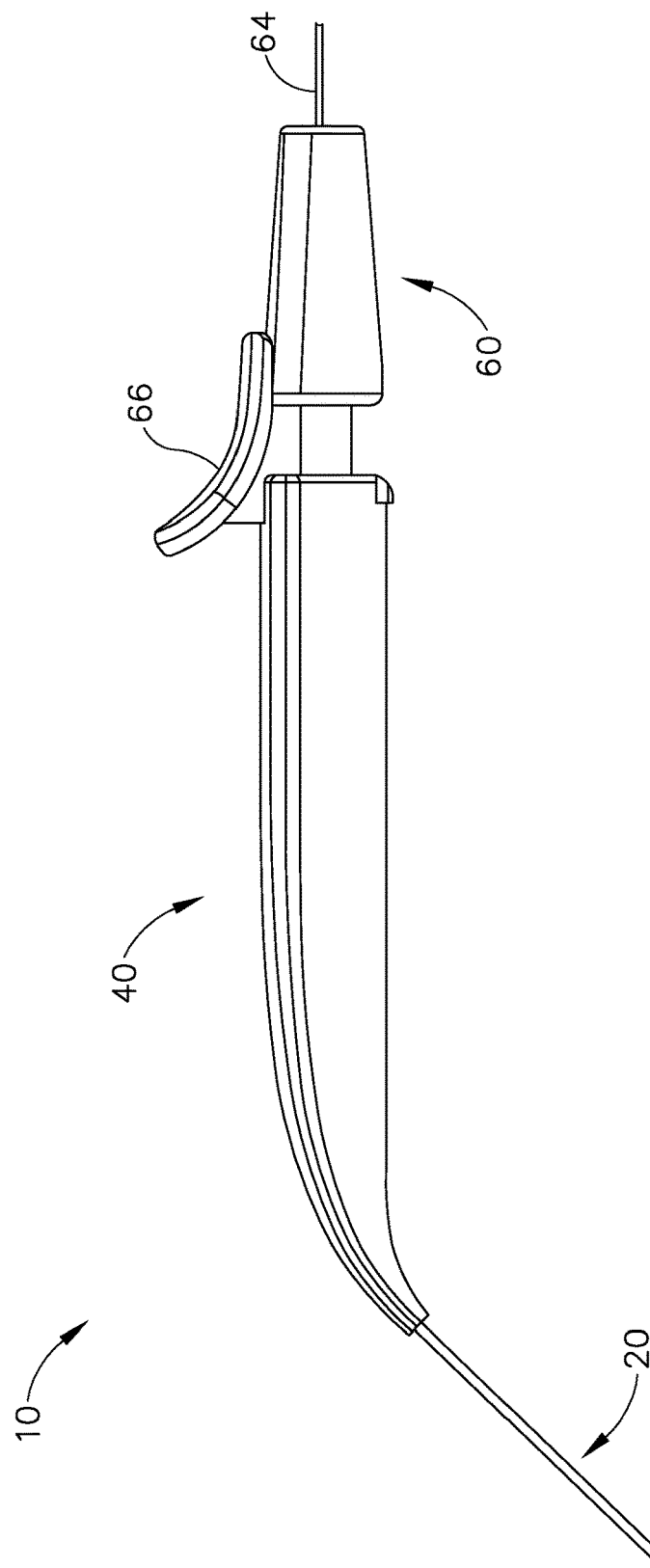
FIG. 2 depicts a side elevational view of the instrument of FIG. 1.
Figure 3:
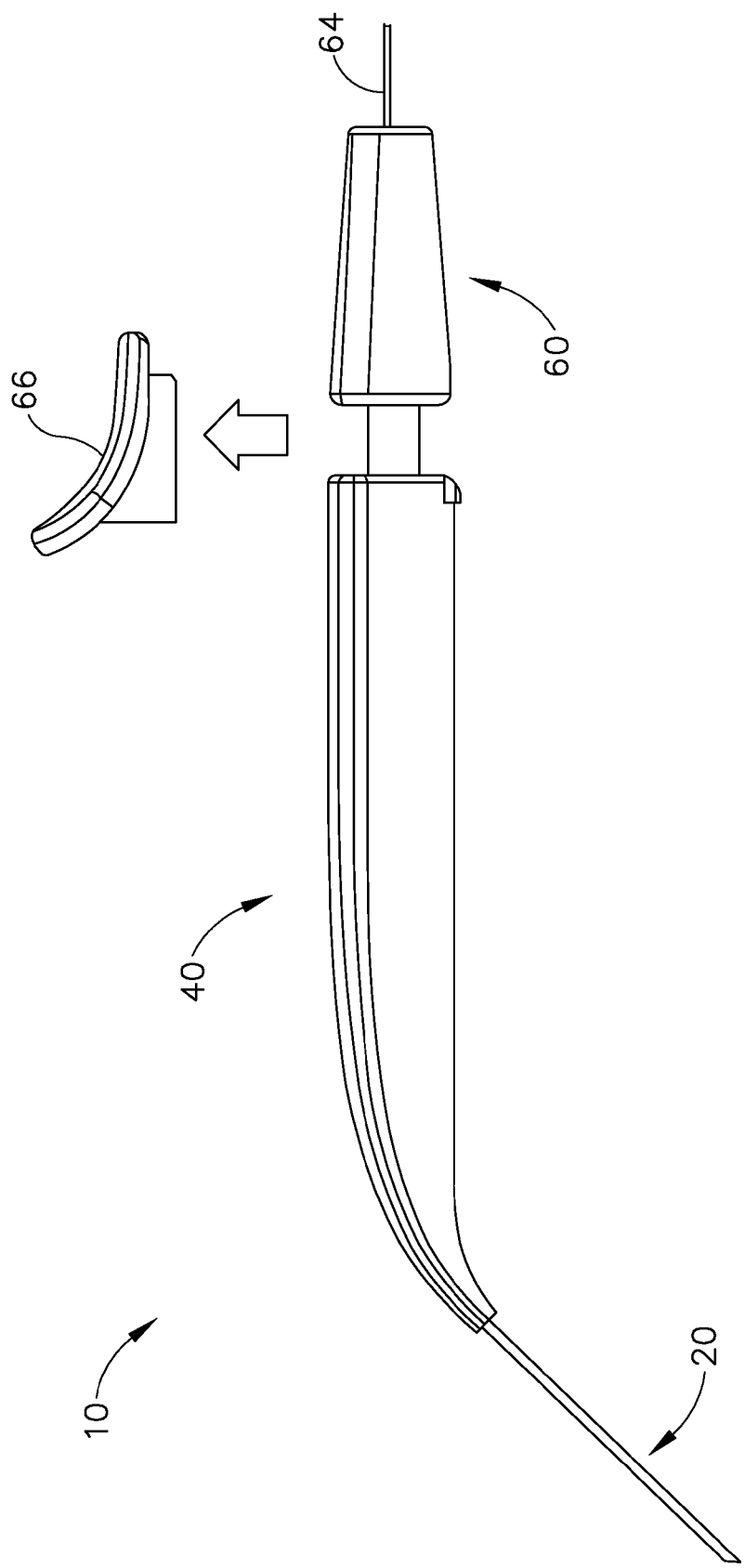
FIG. 3 depicts another side elevational view of the instrument of FIG. 1, with a locking member removed.
Figure 4:
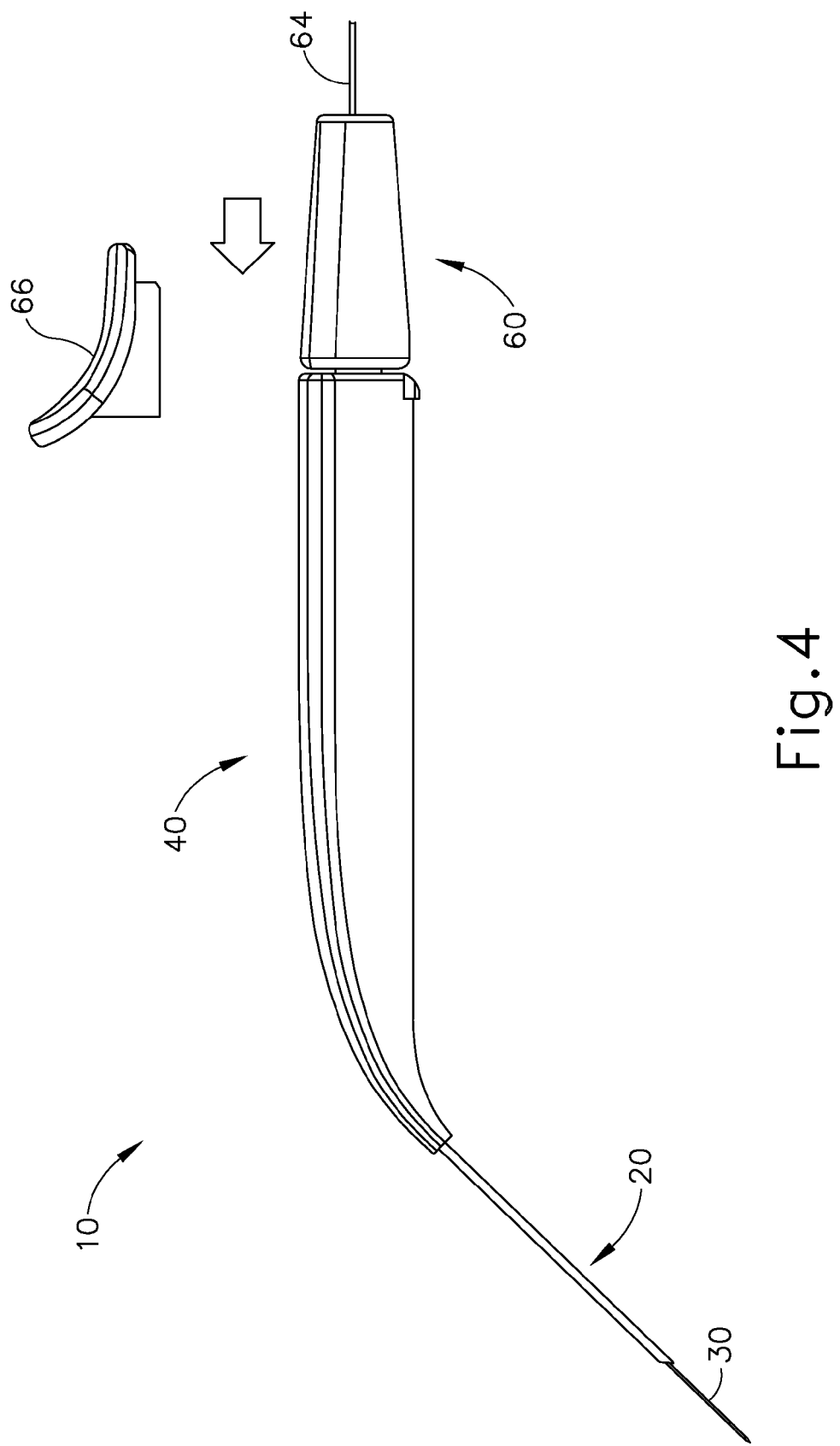
FIG. 4 depicts another side elevational view of the instrument of FIG. 1, with an actuation member advanced distally to extend the needle distally from the cannula.

FIGS. 2-4 show an exemplary actuation of instrument (10). In particular, as can be seen in FIG. 2, needle (30) is initially retracted into cannula (20) and locking member (66) is positioned between body (40) and actuation member (62), thereby preventing advancement of actuation member (62). With instrument (10) in this configuration, cannula (20) may be positioned within an eye of a patient as will be described in greater detail below.

Once cannula (20) is positioned within an eye of a patient, an operator may desire to advance needle (30) relative to cannula (20). To advance needle (30), an operator may first remove locking member (66) by pulling locking member (66) away from instrument (10), as can be seen in FIG. 3. Once locking member (66) is removed, actuation member (62) may be moved or translated relative to body (40) to advance needle (30) relative to cannula (20) as described in U.S. patent application Ser. No. 14/619,256, entitled "Method and Apparatus for Suprachoroidal Administration of Therapeutic Agent," filed Feb. 11, 2015, the disclosure of which is incorporated by reference herein. Actuation member (62) of the present example is only configured to translate needle (30) and not rotate needle (30). In other examples, it may be desirable to rotate needle (30). Accordingly, alternative examples may include features in actuation member (62) to rotate and translate needle (30).

In the present example, advancement of actuation member (62) into contact with body (40) as shown in FIG. 4 corresponds to advancement of needle (30) to a position relative to cannula (20) to a predetermined amount of penetration within an eye of a patient. In other words, instrument (10) is configured such that an operator only has to advance actuation member (62) into contact with body (40) to properly position needle (30) within an eye of a patient. In some examples, the predetermined amount of advancement of needle (30) relative to cannula (20) is between approximately 0.25 mm to approximately 10 mm; or more particularly within the range of approximately 0.1 mm to approximately 10 mm; or more particularly within the range of approximately 2 mm to approximately 6 mm; or more particularly to approximately 4 mm. In other examples, contact between actuation member (62) and body (40) may have no particular significance besides the maximum advancement of needle (30) relative to cannula (20). Instead, instrument (10) may be equipped with certain tactile feedback features to indicate to an operator when needle (30) has been advanced to certain predetermined distances relative to cannula (20). Accordingly, an operator may determine the desired depth of penetration of needle (30) into a patient's eye based on direct visualization of indicia on instrument and/or based on tactile feedback from instrument (10). Of course, such tactile feedback features may be combined with the present example, as will be apparent to those of ordinary skill in the art in view of the teachings herein.

II. Exemplary Alternative Instruments and Features

In some examples, it may be desirable to vary certain components or features of the instruments described herein. For instance, it may be desirable to utilize instruments similar to instrument (10) with alternative mechanisms to actuate needle (30). Yet in other examples, it may be desirable to utilize instruments similar to instrument (10) equipped with different cannula (20) or needle (30) geometries. Instruments having the above referenced variations may be desirable for different surgical procedures, or surgical procedures similar to the procedure discussed above, to engage tissue structures having varying physical properties. While certain examples of variations are described herein, it should be understood that the instruments described herein may include any other alternative features as will be apparent to those of ordinary skill in the art in view of the teachings herein.

Figure 7:
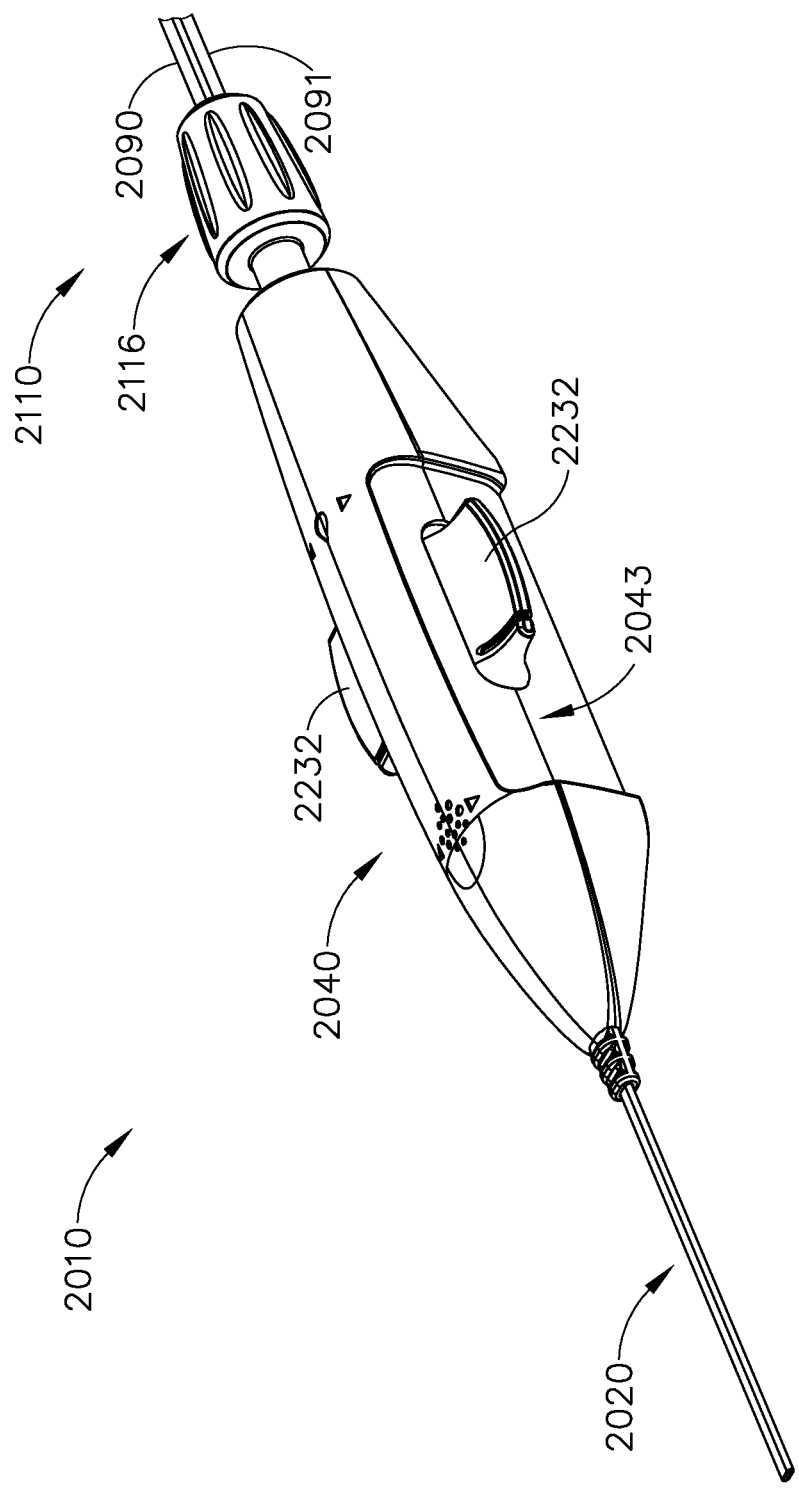
FIG. 7 depicts a perspective view of another exemplary alternative instrument for subretinal administration of a therapeutic agent from a suprachoroidal approach.

FIG. 7 shows an exemplary alternative instrument (2010) that is similar to instrument (10) described above. While certain features and operabilities of instrument (2010) are described below, it should be understood that, in addition to or in lieu of the following, instrument (2010) may be configured and/or operable in accordance with any of the teachings of U.S. patent application Ser. No. 14/619,256, entitled "Method and Apparatus for Suprachoroidal Administration of Therapeutic Agent," filed Feb. 11, 2015, the disclosure of which is incorporated by reference herein. Like with instrument (10), instrument (2010) of the present example is generally usable in the procedure described herein to deliver a therapeutic fluid suprachoroidally to an eye of a patient. It should therefore be understood that instrument (2010) may be readily used in place of instrument (10) to perform the medical procedures described herein. Like instrument (10), instrument (2010) of this example comprises a cannula (2020), a body (2040), and an actuation assembly (2100). Cannula (2020) includes a nitinol needle extending therethrough and is substantially the same as cannula (20) described above. In the present example, cannula (2020) and the needle are substantially identical to cannula (20) and needle (30) described above.

The primary difference between instrument (10) and instrument (2010) is that actuation assembly (2100) of instrument (2010) is rotatable instead of being slidable. Additionally, instrument (2010) includes a valve assembly (not shown) that is operable to change the fluid state of the needle. Actuation assembly (2100) is generally operable to translate the valve assembly longitudinally to thereby translate the needle longitudinally relative to cannula (2020) through rotation of a knob member (2110).

When actuation assembly (2100) is in the proximal position, an operator may rotate knob member (2110) in either a counter clockwise or clockwise direction. If knob member (2110) is rotated in the counter clockwise direction, rotation member (2110) will merely rotate freely. To begin advancement of actuation assembly (2100), the valve assembly, and the needle, an operator may rotate knob member (2110) in the clockwise direction. Clockwise rotation of knob member (2110) will act to translate knob member (2110) distally and will also act to translate the valve assembly and the needle distally. An operator may continue clockwise rotation of knob member (2110) to drive the needle out of the distal end of cannula (2020). Once the needle has been advanced to its furthest distal position relative to the distal end of cannula (2020), further clockwise rotation of knob member (2110) will merely result in free rotation of knob member (2110) due to slipping of clutch features that are integrated into actuation assembly (2100). With the needle in the distal position, the operator may actuate valve assembly to enable the delivery of therapeutic agent via the needle as described in greater detail below.

After the therapeutic agent is delivered, the operator may then wish to retract the needle. Counter clockwise rotation of knob member (2110) will cause proximal translation of actuation assembly (2100), the valve assembly, and the needle relative to body (2040). It should be understood that as actuation assembly (2100) is rotated to actuate the valve assembly, and the needle, the valve assembly and the needle remain substantially rotationally stationary relative to body (2040). It should also be understood that although rotation member (2110) of the present example is described as being manually rotated, rotation member (2110) may be rotated via a motor and/or some other motive source. Thus, it should be understood that translation of the needle may be mechanically/electrically driven via a servomotor. The actuation of a servomotor may be controlled by a servo controller as will be described in more detail below. Such a servo control may be manually operated. Additionally or alternatively, such a servo controller may be operated via a computer acting on feedback from instrument (2010) or any other component described herein.

III. Exemplary Suture Measurement Template

Figure 8:
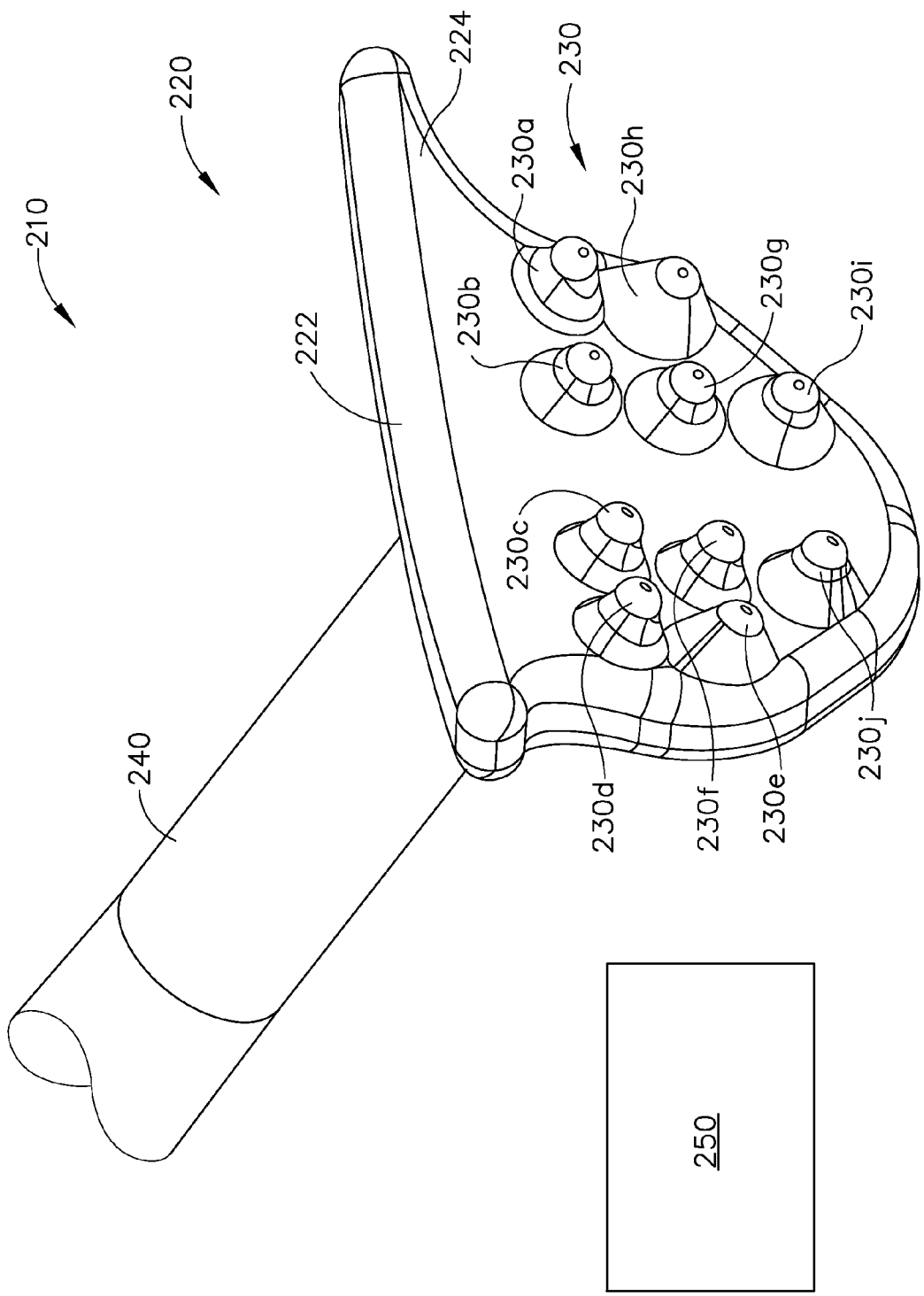
FIG. 8 depicts a perspective view of an exemplary suture measurement template for use in an exemplary method for the administration of a therapeutic agent from a suprachoroidal approach.

FIG. 8 shows an exemplary suture measurement template (210) that may be used in a procedure providing subretinal delivery of a therapeutic agent from a suprachoroidal approach, as will be described in greater detail below. Generally, template (210) is configured to be pressed against an eye of a patient to stamp a particular pattern of pigment onto the patient's eye. It should be understood that reference herein to pressing template (210) against an eye of a patent may include, but is not necessarily limited to, pressing template (210) directly against the sclera (304) surface (e.g., after the conjunctiva has been taken down or otherwise displaced). Template (210) comprises a rigid body (220) and a rigid shaft (240). As will be described in greater detail below, body (220) is generally contoured to correspond to the curvature of a patient's eye such that body (220) may be pressed or placed onto at least a portion of the patient's eye. Body (220) comprises an upper guide portion (222) and a plurality of protrusions (230) extending distally from an eye face (224) of body (220).

Upper guide portion (222) is generally semi-circular in shape and is disposed at the top of body (220). The semi-circular shape of upper guide portion (222) has a radius that corresponds to the curvature of the limbus of a patient's eye. In other words, upper guide portion (222) curves proximally along a first radius corresponding to a radius of curvature of a patient's eyeball; and downwardly (toward the longitudinal axis of shaft (240)) along a second radius corresponding to a radius of curvature of the limbus of the patient's eye. As will be described in greater detail below, upper guide portion (222) may be used to properly locate template (210) relative to the limbus of the patient's eye. Accordingly, any pigmentation that may be deposited onto a patient's eye by template may be positioned relative to the limbus of the patient's eye.

Protrusions (230) are spaced a predetermined distance from upper guide portion (222). In particular, protrusions (230) form a pattern that may correspond to relevant marks for use during the method described below. Protrusions (230) of the present example comprise four suture loop protrusions (230a-230h) and two sclerotomy protrusions (230i, 230j). Suture loop protrusions (230a-320h) and sclerotomy protrusions (230i, 230j) extend outwardly from body (220) an equal distance such that protrusions (230) collectively maintain the curvature defined by body (220). In other words, the tips of protrusions (230a-230j) all lie along a curved plane that is defined by a radius of curvature complementing the radius of curvature of the patient's eyeball. The tips of protrusions (230a-230j) are rounded and atraumatic such that protrusions (230a-230j) may be pressed against the eye without damaging the sclera or other portions of the patient's eye.

Shaft (240) extends proximally from body (220). Shaft (240) is configured to permit an operator to grasp template (210) and manipulate body (220). In the present example, shaft (240) is integral with body (220). In other examples, shaft (240) may be selectively attachable to body by a mechanical fastening means such as a threaded coupling or a mechanical snap fit, etc. In some versions, an operator may be presented with a kit comprising a shaft (240) and a plurality of bodies (220). The bodies (220) may have different curvatures to correspond with different eyeballs having different radii of curvature. The operator may thus select an appropriate body (220) from the kit based on the anatomy of the particular patient before the operator; and the operator may then secure the selected body (220) to the shaft (240). Although not shown, it should be understood that the proximal end of shaft (240) may additionally include a t-grip, knob, or other gripping feature to permit an operator to more readily grip shaft (240).

In an exemplary use, suture loop protrusions (232) and sclerotomy protrusions (234) each correspond to a particular portion of the method described below. In particular, prior to, or during the method described below, an operator may coat protrusions (230) with a biocompatible pigment or ink by pressing protrusions (230) onto a pigment or ink pad (250), by brushing the pigment or ink onto protrusions (230), or by otherwise applying the pigment or ink to protrusions (230). Of course, some versions may provide protrusions (230) pre-inked, such that the operator does not need to perform a step of applying ink to protrusions (230) during the presently described procedure. Once protrusions (230) have received the pigment or ink, an operator may mark an eye of a patent by pressing protrusions (230) of template (210) onto the eye of the patient, as will be described in greater detail below. Once template (210) is removed from an eye of a patient, the pigment from protrusions may remain adhered to the eye to mark particular points of interest, as will be described in greater detail below.

IV. Exemplary Method for Subretinal Delivery of Therapeutic Agent from a Suprachoroidal Approach FIGS. 9A-11C show an exemplary procedure for subretinal delivery of therapeutic agent from a suprachoroidal approach using instrument (10) described above. It should be understood however, that instrument (2010) may be readily used in addition to or in lieu of instrument (10) in the procedure described below. By way of example only, the method described herein may be employed to treat macular degeneration and/or other ocular conditions. Although the procedure described herein is discussed in the context of the treatment of age-related macular degeneration, it should be understood that no such limitation is intended or implied. For instance, in some merely exemplary alternative procedures, the same techniques described herein may be used to treat retinitis pigmentosa, diabetic retinopathy, and/or other ocular conditions. Additionally, it should be understood that the procedure described herein may be used to treat either dry or wet age-related macular degeneration.

Figure 9A:
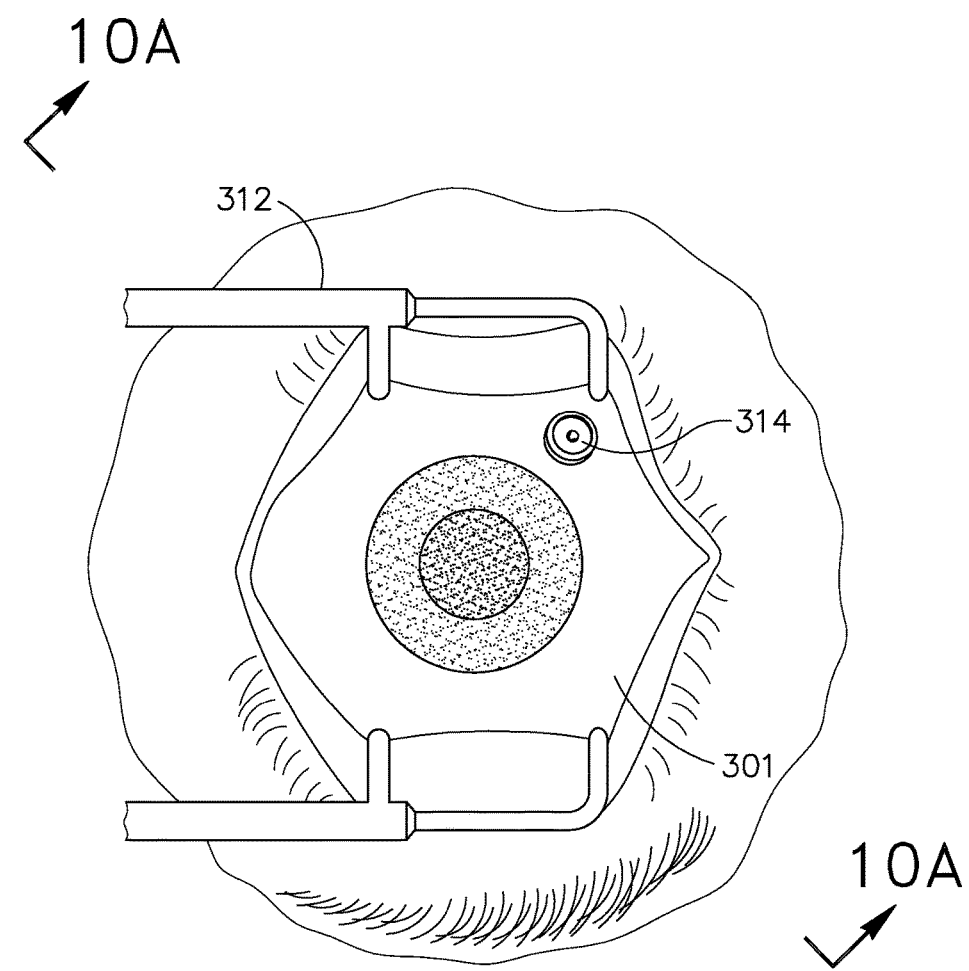
FIG. 9A depicts a top plan view of an eye of a patient, with surrounding structures of the eye immobilized and a chandelier installed.
Figure 10A:
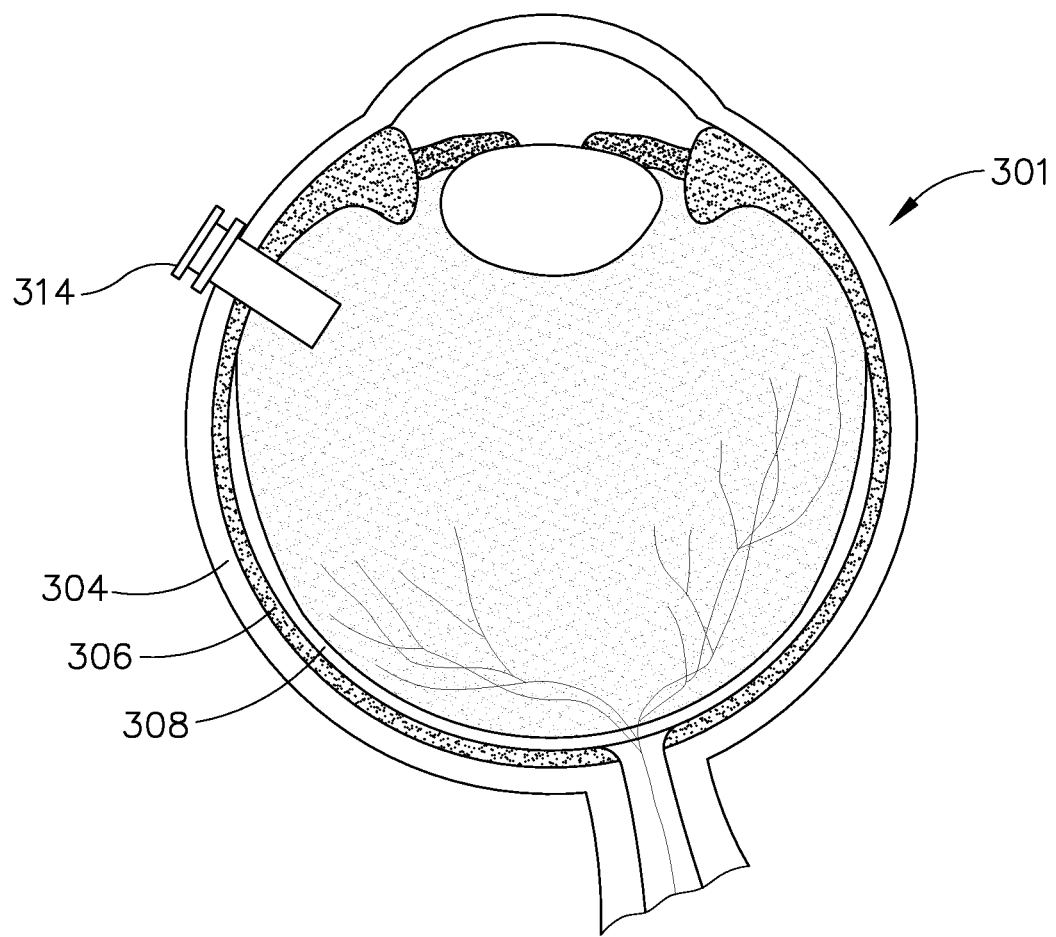
FIG. 10A depicts a cross-sectional view of the eye of FIG. 9A, with the cross-section taken about line 10A-10A of FIG. 9A.
Figure 10B:
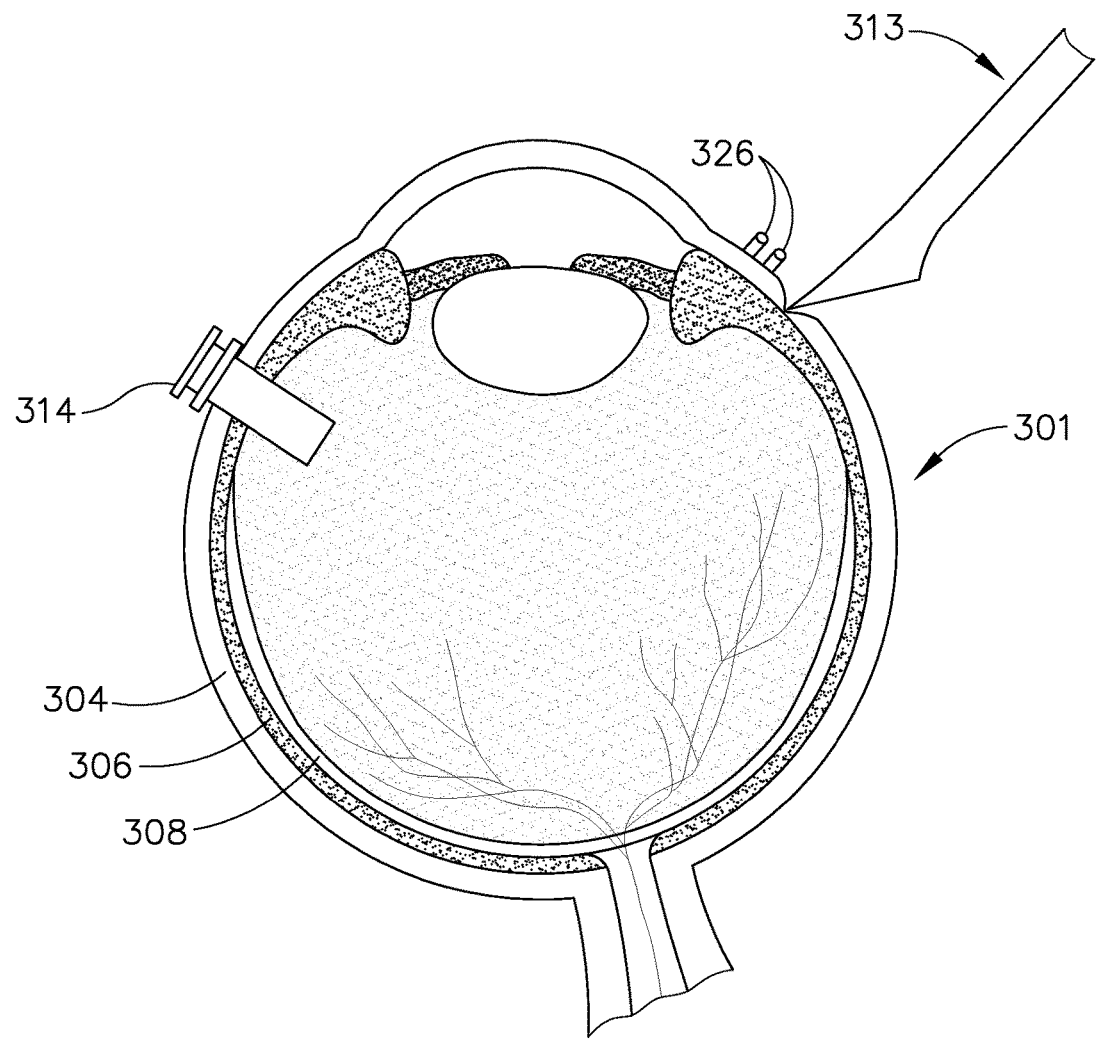
FIG. 10B depicts a cross-sectional view of the eye of FIG. 9A, with the cross-section taken about line 10B-10B of FIG. 9E.

As can be seen in FIG. 9A, the procedure begins by an operator immobilizing tissue surrounding a patient's eye (301) (e.g., the eyelids) using a speculum (312), and/or any other instrument suitable for immobilization. While is immobilization described herein with reference to tissue surrounding eye (301), it should be understood that eye (301) itself may remain free to move. Once the tissue surrounding eye (301) has been immobilized, an eye chandelier port (314) is inserted into eye (301) to provide intraocular illumination when the interior of eye (301) is viewed through the pupil. In the present example, eye chandelier port (314) is positioned in the inferior medial quadrant such that a superior temporal quadrant sclerotomy may be preformed. As can be seen in FIG. 10A, eye chandelier port (314) is positioned to direct light onto the interior of eye (314) to illuminate at least a portion of the retina (e.g., including at least a portion of the macula). As will be understood, such illumination corresponds to an area of eye (301) that is being targeted for delivery of therapeutic agent. In the present example, only chandelier port (314) is inserted at this stage, without yet inserting an optical fiber (315) into port (314). In some other versions, an optical fiber (315) may be inserted into chandelier port (314) at this stage. In either case, a microscope may optionally be utilized to visually inspect the eye to confirm proper positioning of eye chandelier port (314) relative to the target site. In some examples, the target region may be identified by a relative lack of retinal pigmentation. Although FIG. 9A shows a particular positioning of eye chandelier port (314), it should be understood that eye chandelier port (314) may have any other positioning as will be apparent to those of ordinary skill in the art in view of the teachings herein.

Figure 9B:
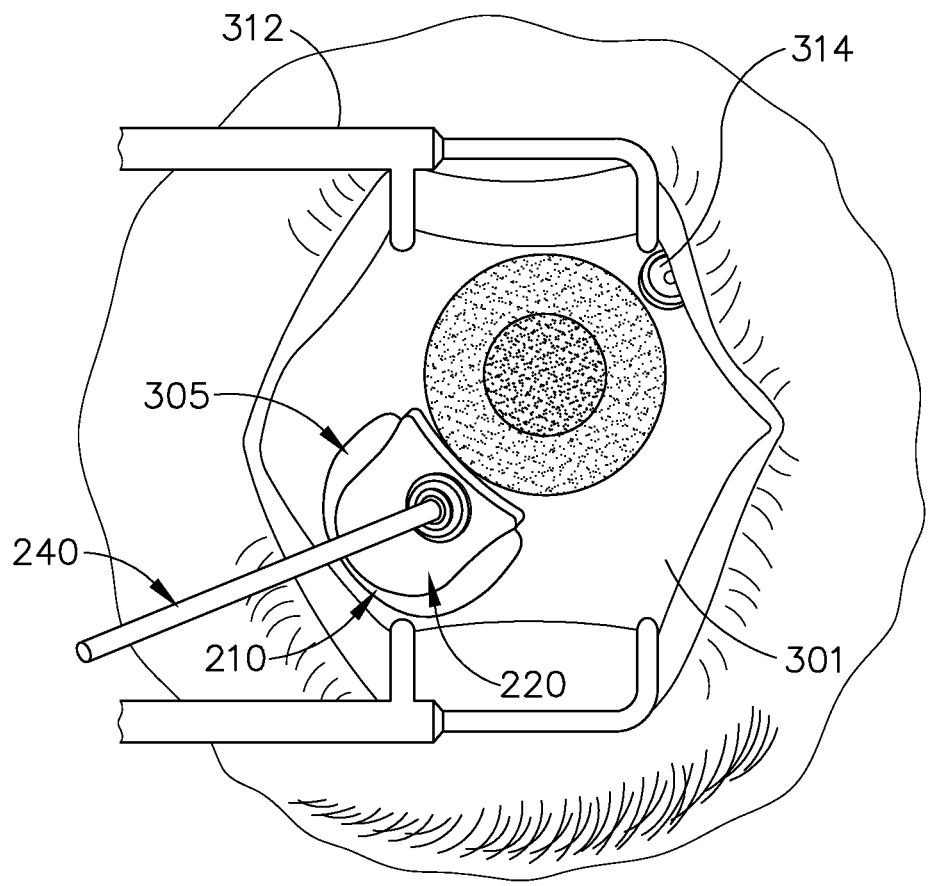
FIG. 9B depicts a top plan view of the eye of FIG. 9A, with the template of FIG. 8 disposed on the eye.
Figure 9C:
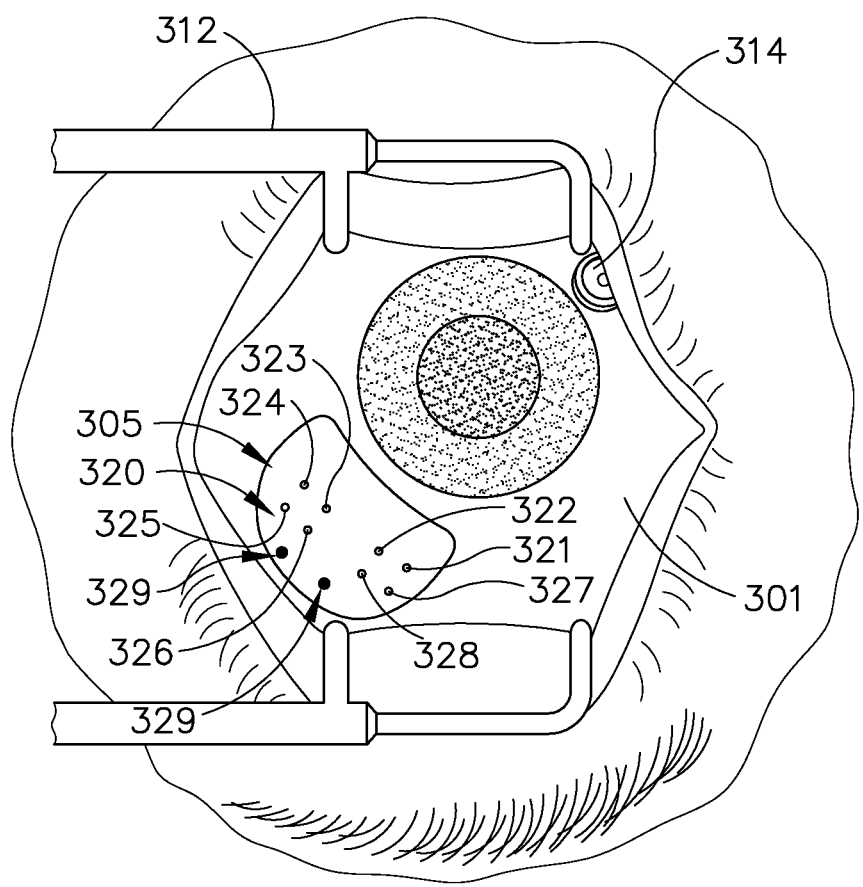
FIG. 9C depicts a top plan view of the eye of FIG. 9A, with a plurality of markers disposed on the eye.

Once eye chandelier port (314) has been positioned, the sclera (304) may be accessed by dissecting the conjunctiva by incising a flap in the conjunctiva and pulling the flap posteriorly. After such a dissection is completed, the exposed surface (305) of the sclera (304) may optionally be blanched using a cautery tool to minimize bleeding. Once conjunctiva dissection is complete, the exposed surface (305) of the sclera (304) may optionally be dried using a WECK-CEL or other suitable absorbent device. Template (210), described above, may then be used to mark eye (301). As can be seen in FIG. 9B, template (210) is positioned to align with the limbus of eye (301). An operator may apply a light force to template (210) to apply pigment to eye (301). Template (210) is then removed, leaving pigment adhered to the exposed surface (305) of the sclera (304) to provide a visual guide (320) for an operator, as can be seen in FIG. 9C. An operator may then use visual guide (320) to attach a suture loop assembly (330) and to perform a sclerotomy. Visual guide (320) comprises a set of suture loop markers (321, 322, 323, 324, 325, 326, 327) and a pair of sclerotomy markers (329).

Figure 9D:
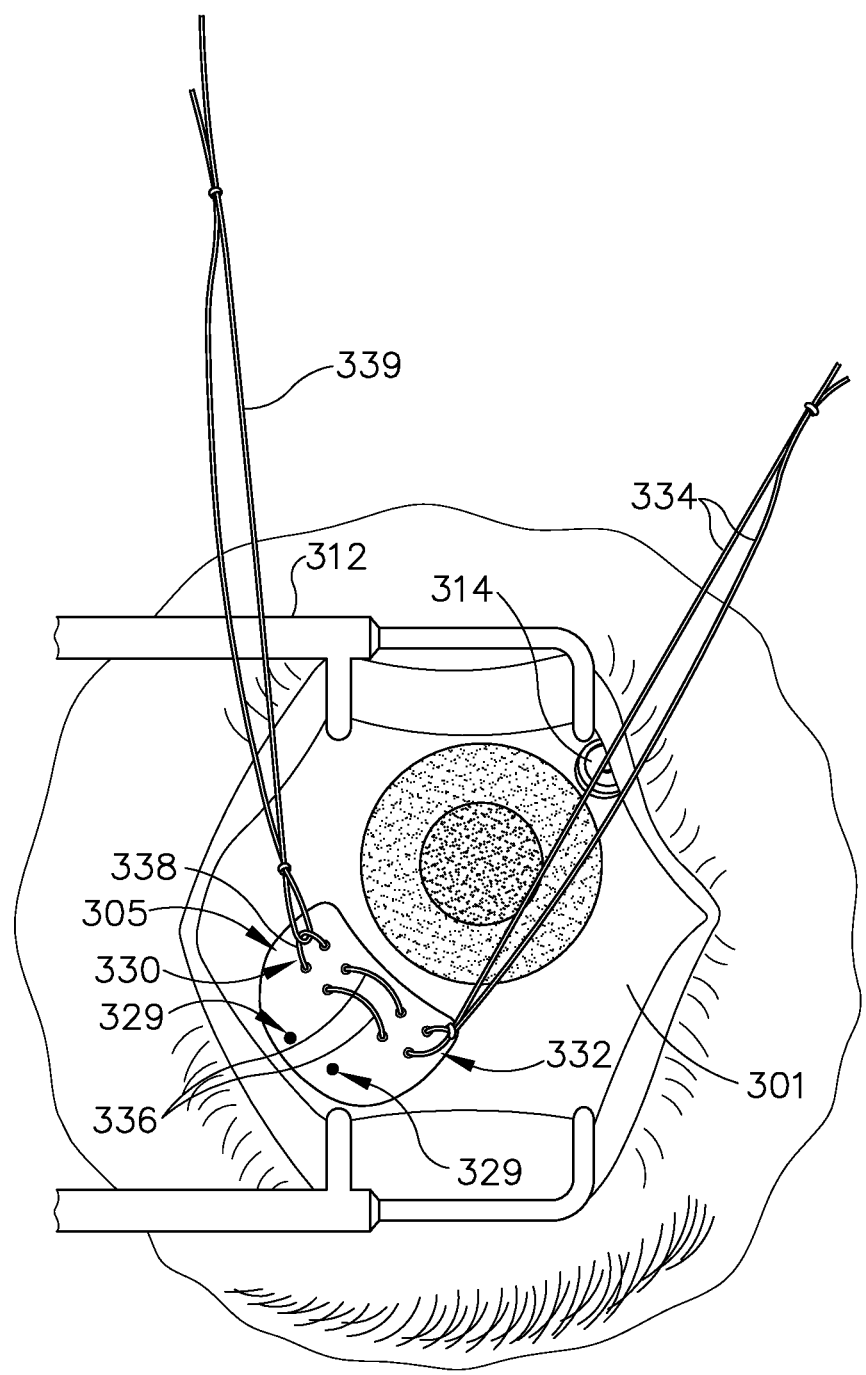
FIG. 9D depicts a top plan view of the eye of FIG. 9A, with a suture loop attached to the eye.
Figure 9E:
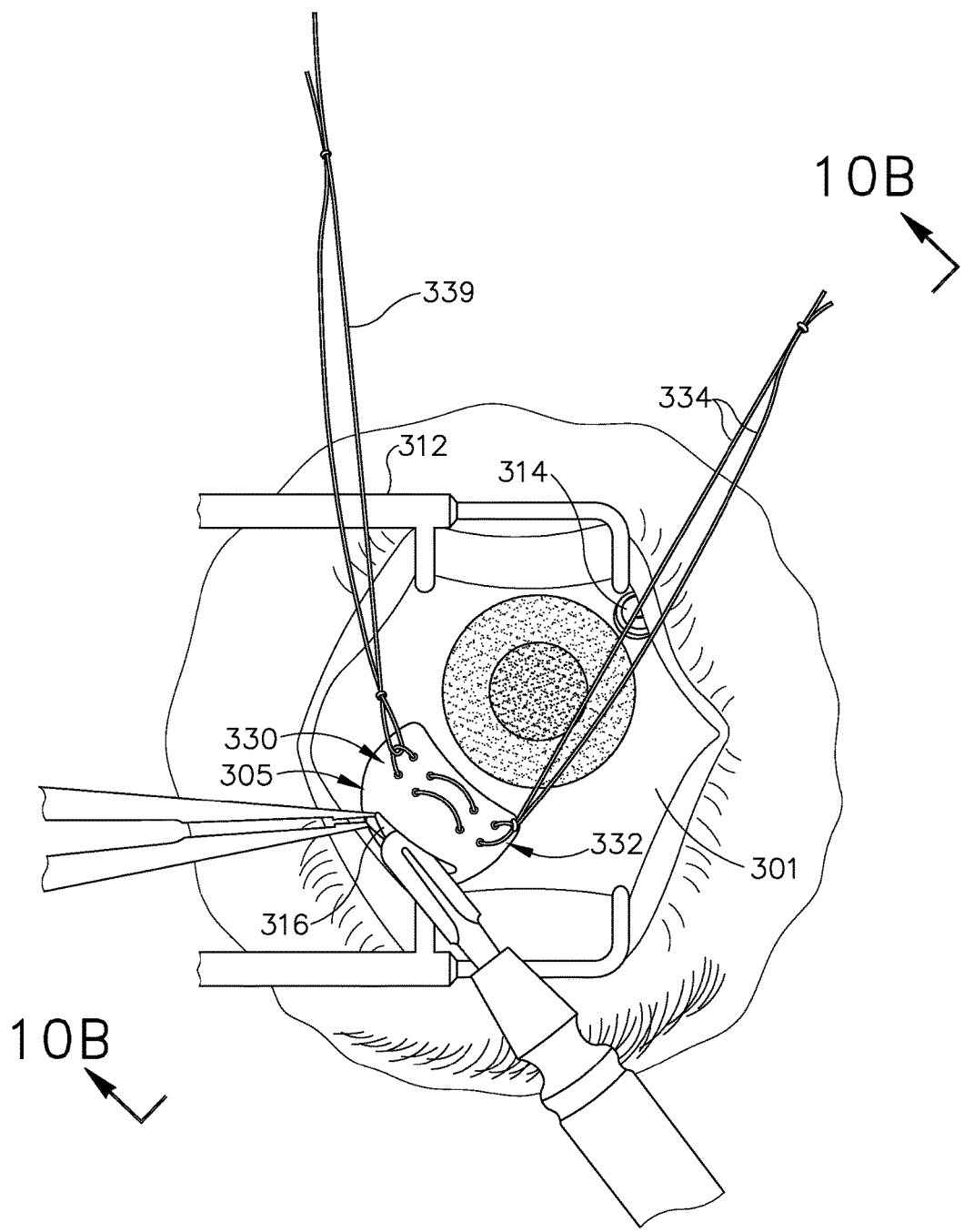
FIG. 9E depicts a top plan view of the eye of FIG. 9A, with a sclerotomy being performed.

FIG. 9D shows a completed suture loop assembly (330). As will be described in greater detail below, suture loop assembly (330) is generally configured to guide cannula (20) of instrument (10) through a sclerotomy and into eye (301). An exemplary procedure that may be employed to create the suture loop assembly (330) that is shown in FIG. 9D is described in U.S. patent application Ser. No. 14/619,256, entitled "Method and Apparatus for Suprachoroidal Administration of Therapeutic Agent," filed Feb. 11, 2015, the disclosure of which is incorporated by reference herein. Once suture loop assembly (330) has been attached to eye (301), a sclerotomy may be performed on eye (301). As seen in FIG. 9E, eye (301) is cut between sclerotomy markers (329) using a conventional scalpel (313) or other suitable cutting instrument. Although sclerotomy markers (329) are shown as comprising two discrete dots, it should be understood that in other examples, markers (329) may comprise any other type of markings such as a solid, dotted or dashed line. The sclerotomy procedure forms a small incision (316) through sclera (304) of eye (301). As can best be seen in FIG. 10B, the sclerotomy is preformed with particular care to avoid penetration of the choroid (306). Thus, the sclerotomy procedure provides access to the space between sclera (304) and choroid (306). Once incision (316) is made in eye (301), a blunt dissection may optionally be performed to locally separate sclera (304) from choroid (306). Such a dissection may be performed using a small blunt elongate instrument, as will be apparent to those of ordinary skill in the art in view of the teachings herein.

Figure 9F:
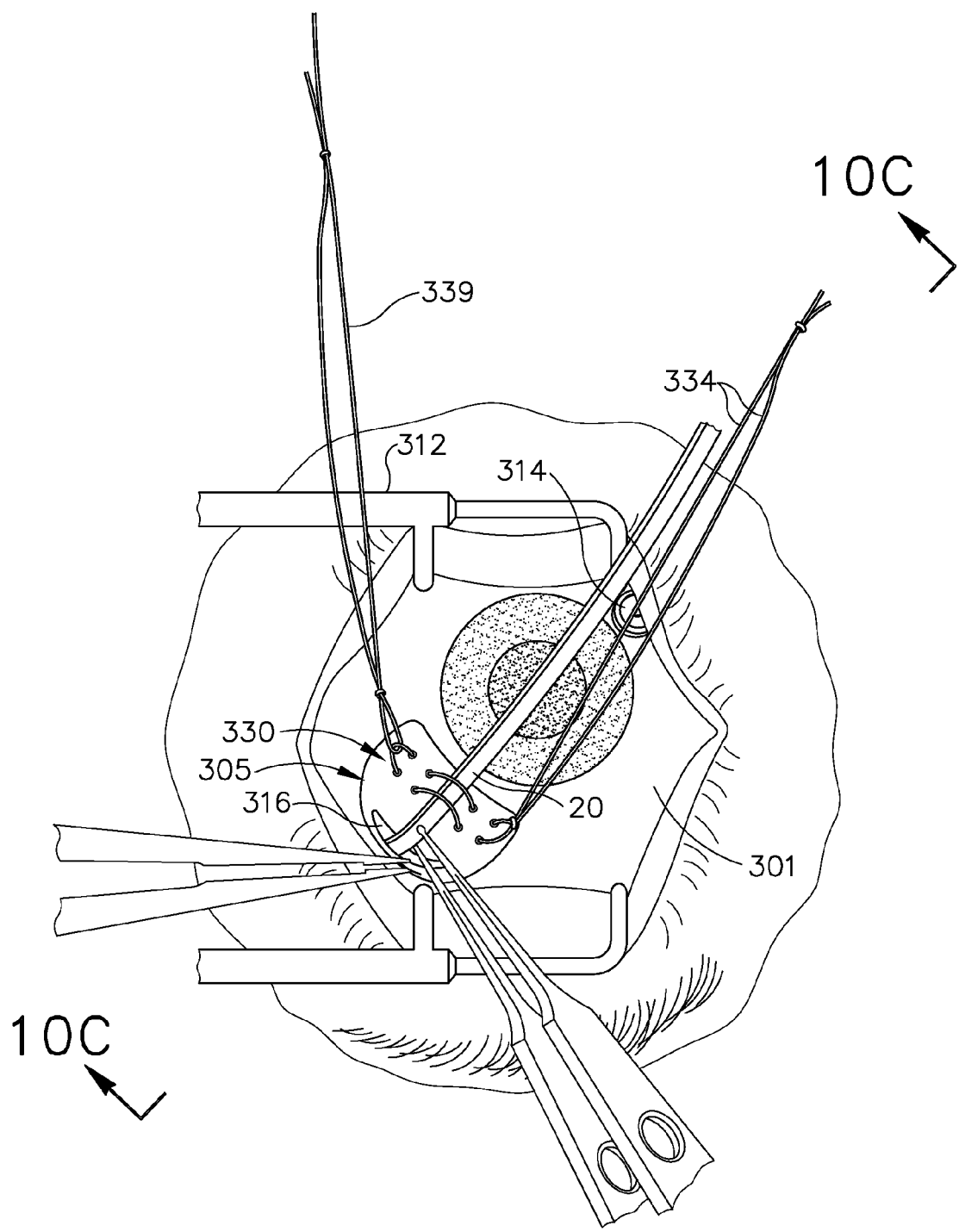
FIG. 9F depicts a top plan view of the eye of FIG. 9A, with the instrument of FIG. 1 being inserted through the sclerotomy opening and in between the sclera and choroid of the eye.

With the sclerotomy procedure performed, an operator may insert cannula (20) of instrument (10) through incision (316) and into the space between sclera (304) and choroid (306). As can be seen in FIG. 9F, cannula (20) is directed through guide loops (336) of suture loop assembly (330) and into incision (316). As described above, guide loops (336) may stabilize cannula (20). Additionally, guide loops (336) maintain cannula (20) in a generally tangential orientation relative to incision (316). Such tangential orientation may reduce trauma as cannula (20) is guided through incision (316) to stabilize cannula (20) and to prevent damage to surrounding tissue. As cannula (20) is inserted into incision (316) through guide loops (336), an operator may use forceps or other instruments to further guide cannula (20) along an atraumatic path. Of course, use of forceps or other instruments is merely optional, and may be omitted in some examples. Although not shown, it should be understood that in some examples cannula (20) may include one or more markers on the surface of cannula (20) to indicate various depths of insertion. While merely optional, such markers may be desirable to aid an operator in identifying the proper depth of insertion as cannula (20) is guided along an atraumatic path. For instance, the operator may visually observe the position of such markers in relation to guide loops (336) and/or in relation to incision (316) as an indication of the depth to which cannula (20) is inserted in eye (301). By way of example only, one such marker may correspond to an approximately 6 mm depth of insertion of cannula (20).

Once cannula (20) is at least partially inserted into eye (301), an operator may insert an optical fiber (315) into eye chandelier port (314) the fiber (315) had not yet been inserted at this stage. With eye chandelier port (314) in place and assembled with optical fiber (315), an operator may activate eye chandelier port (314) by directing light through optical fiber (315) to provide illumination of eye (301) and thereby visualize the interior of eye (301). Further adjustments to the positioning of cannula (20) may optionally be made at this point to ensure proper positioning relative to the area of geographic atrophy of retina (308). In some instances, the operator may wish to rotate the eye (301), such as by pulling on sutures (334, 339), to direct the pupil of the eye (301) toward the operator in order to optimize visualization of the interior of the eye (301) via the pupil.

Figure 9G:
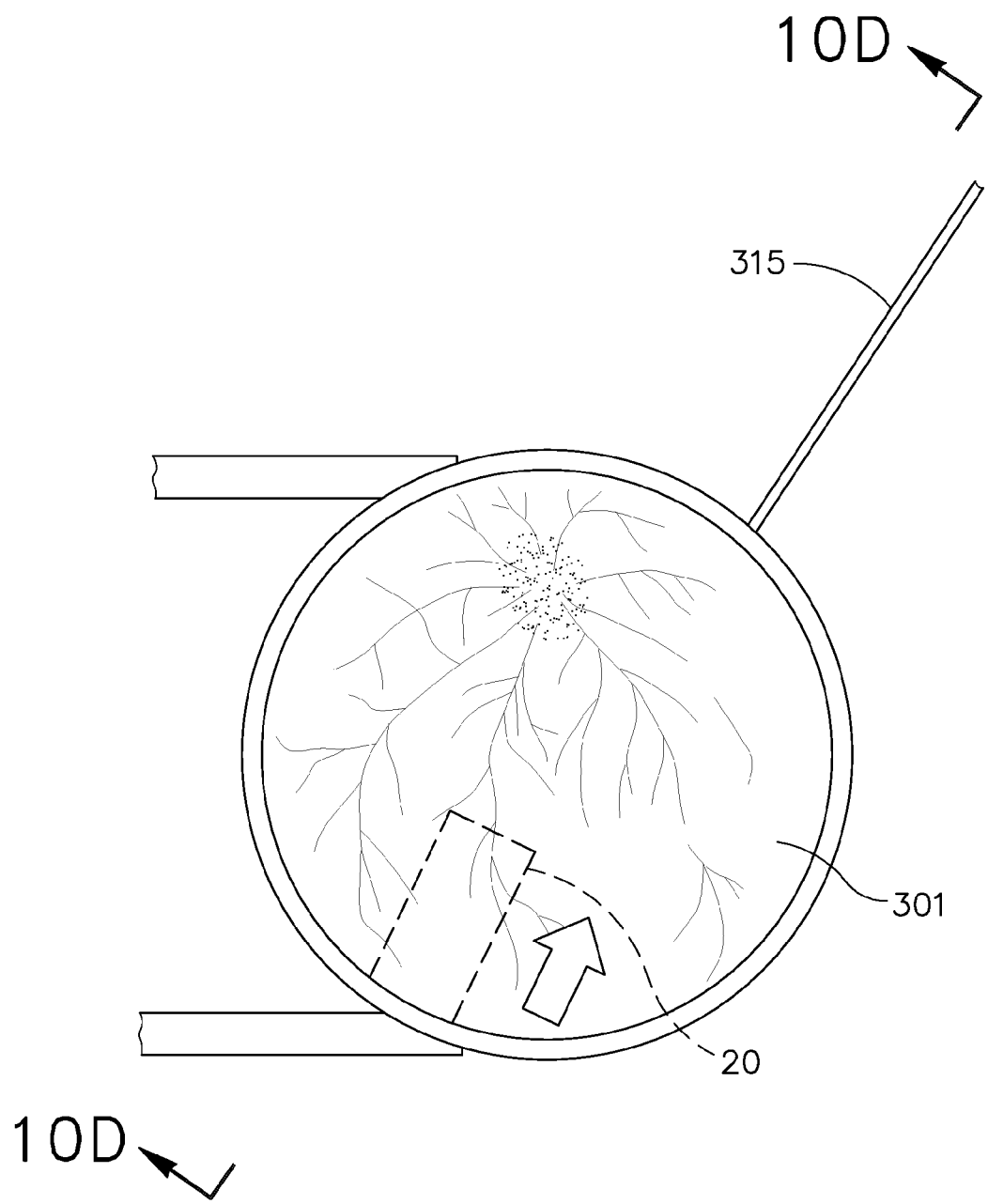
FIG. 9G depicts a top plan view of the eye of FIG. 9A, with the instrument of FIG. 1 under direct visualization at the back of the eye, between the sclera and choroid.
Figure 10C:
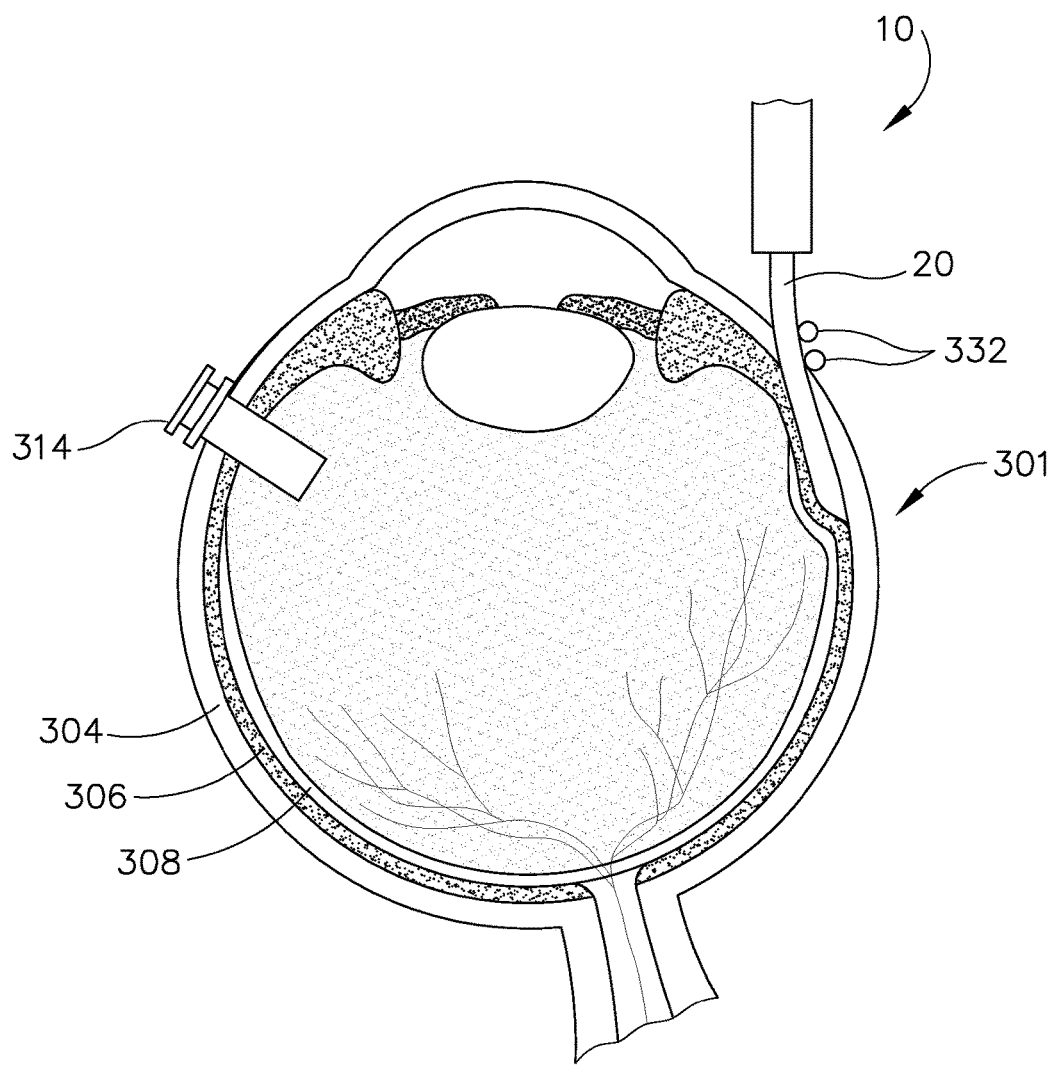
FIG. 10C depicts a cross-sectional view of the eye of FIG. 9A, with the cross-section taken about line 10C-10C of FIG. 9F.
Figure 10D:
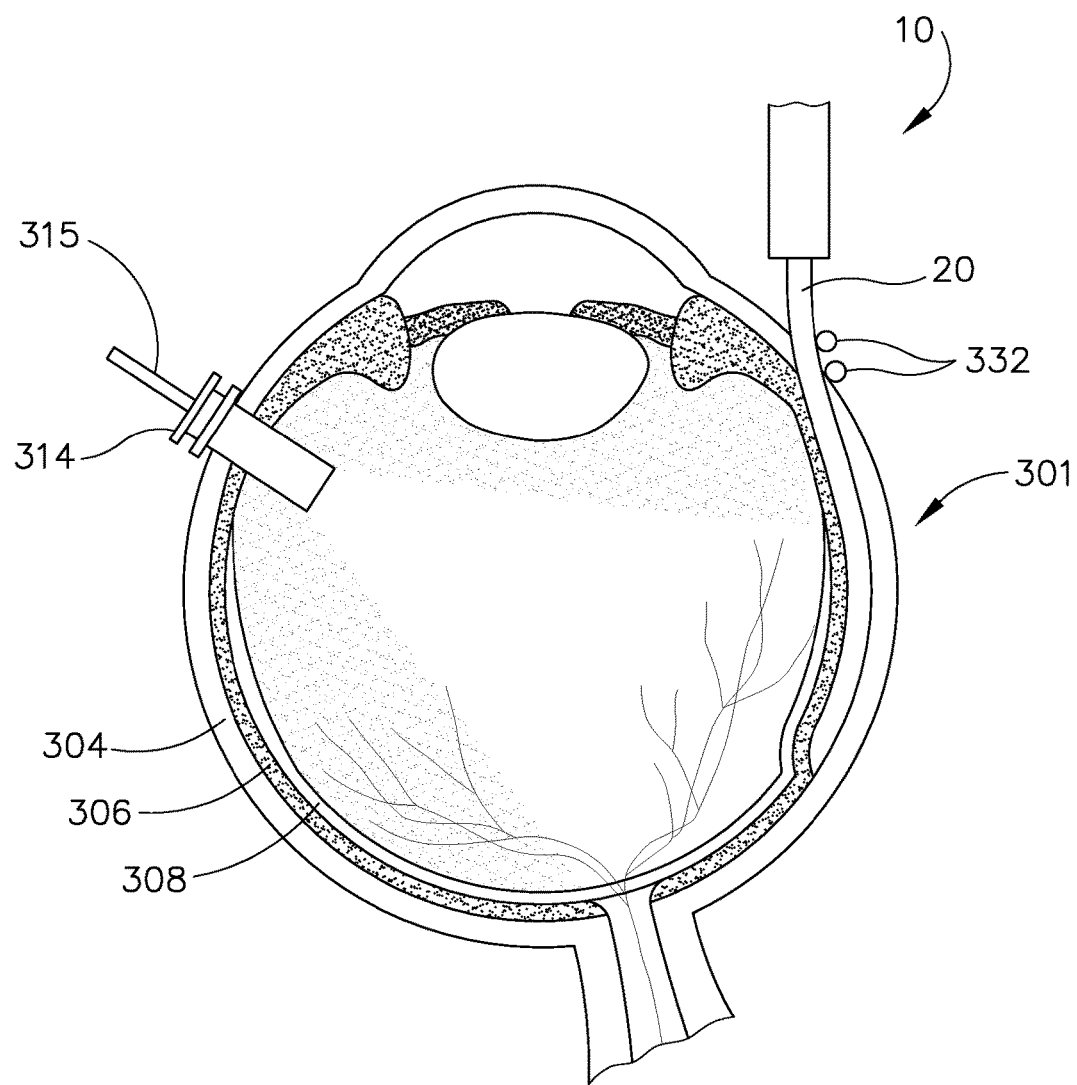
FIG. 10D depicts a cross-sectional view of the eye of FIG. 9A, with the cross-section taken about line 10D-10D of FIG. 9G.
Figure 10E:
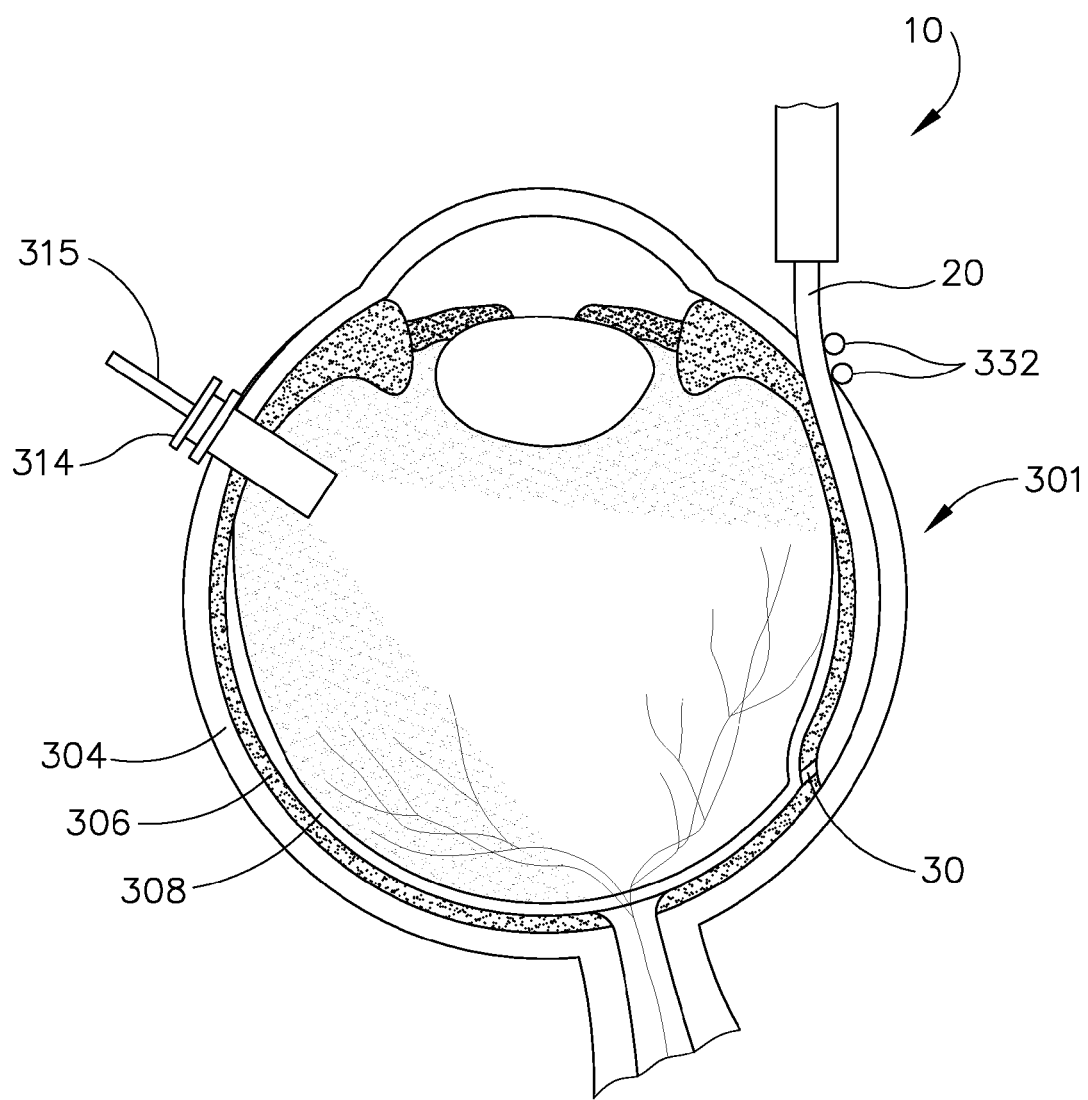
FIG. 10E depicts a cross-sectional view of the eye of FIG. 9A, with the cross-section taken about line 10E-10E of FIG. 9H.

FIGS. 9G and 10C-10D show cannula (20) as it is guided between sclera (304) and choroid (306) to the delivery site for the therapeutic agent. In the present example, the delivery site corresponds to a generally posterior region of eye (301) adjacent to an area of geographic atrophy of retina (308). In particular, the delivery site of the present example is superior to the macula, in the potential space between the neurosensory retina and the retinal pigment epithelium layer. FIG. 9G shows eye (301) under direct visualization through a microscope directed through the pupil of eye (301), with illumination provided through fiber (315) and port (314). As can be seen, cannula (20) is at least partially visible through a retina (308) and choroid (306) of eye (301). Thus, an operator may track cannula (20) as it is advanced through eye (301) from the position shown in FIG. 10C to the position shown in 10D. Such tracking may be enhanced in versions where an optical fiber (34) is used to emit visible light through the distal end of cannula (20).

Figure 9H:
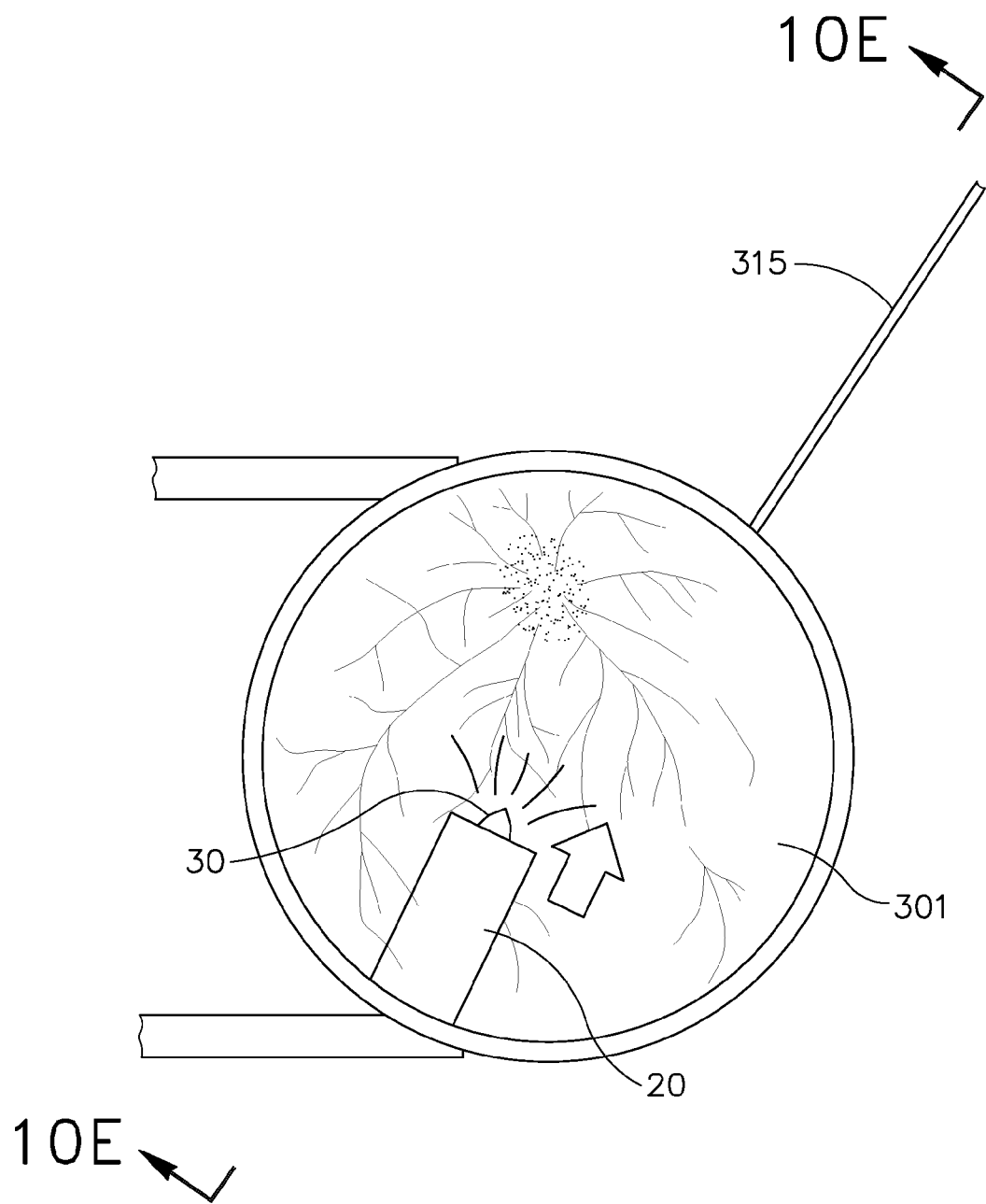
FIG. 9H depicts a top plan view of the eye of FIG. 9A, with the needle of the instrument of FIG. 1 being advanced under direct visualization at the back of the eye, pressing against the outer surface of the choroid causing the choroid to 'tent'.

Once cannula (20) has been advanced to the delivery site as shown in FIG. 10D, an operator may advance needle (30) of instrument (10) as described above with respect to FIGS. 3-4. As can be seen in FIGS. 9H-9I, 10E, and 11A, needle (30) is advanced relative to cannula (20) such that needle (30) pierces through choroid (306) without penetrating retina (308). Immediately prior to penetrating choroid (306), needle (30) may appear under direct visualization as "tenting" the surface of choroid (306), as can be seen in FIG. 9H. In other words, needle (30) may deform choroid (306) by pushing upwardly on choroid, providing an appearance similar to a tent pole deforming the roof of a tent. Such a visual phenomenon may be used by an operator to identify whether choroid (306) is about to be pierced and the location of any eventual piercing. The particular amount of needle (30) advancement sufficient to initiate "tenting" and subsequent piercing of choroid (306) may be of any suitable amount as may be determined by a number of factors such as, but not limited to, general patient anatomy, local patient anatomy, operator preference, and/or other factors. As described above, a merely exemplary range of needle (30) advancement may be between approximately 0.25 mm and approximately 10 mm; or more particularly between approximately 2 mm and approximately 6 mm.

Figure 9I:
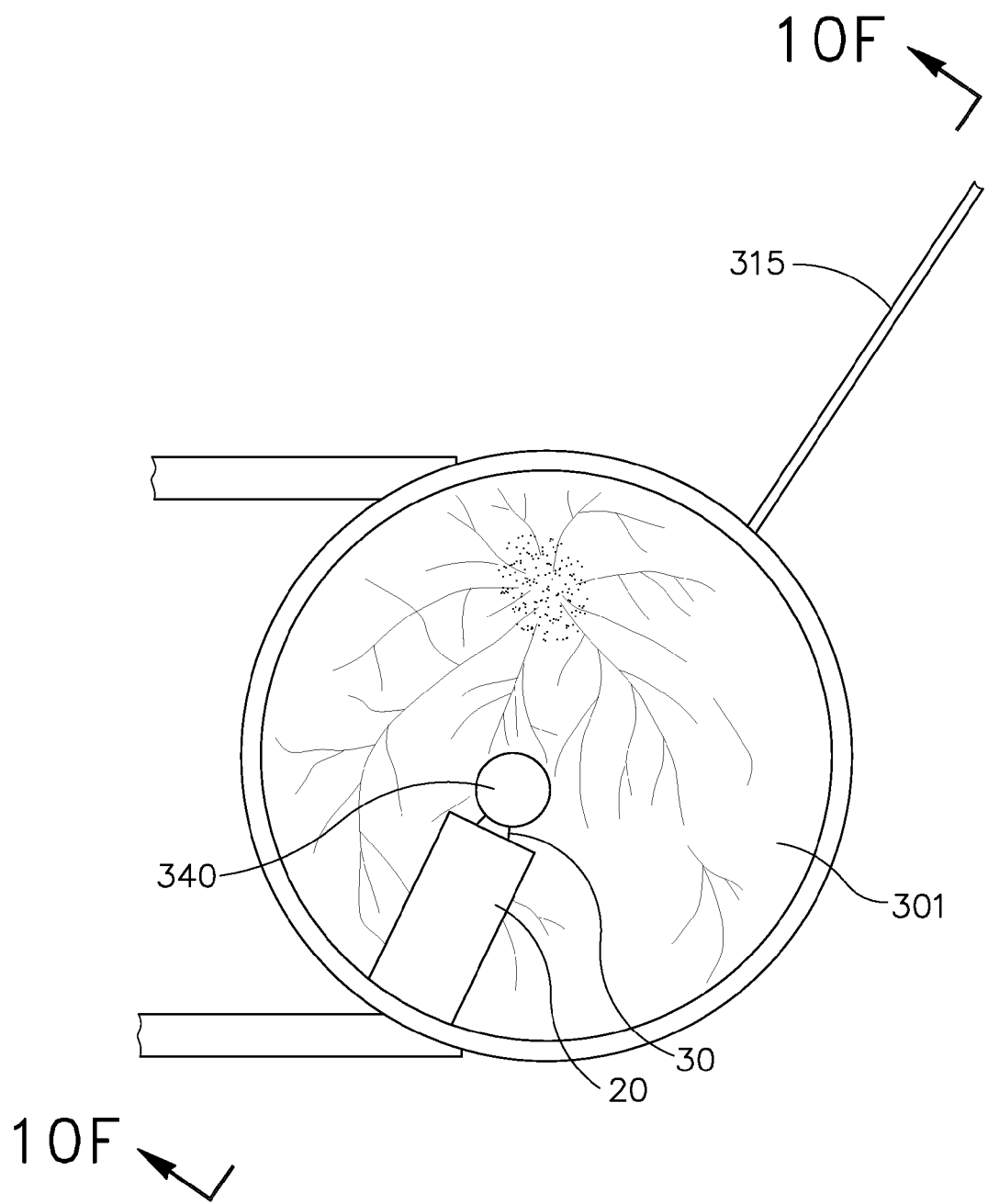
FIG. 9I depicts a top plan view of the eye of FIG. 9A, with the needle dispensing a leading bleb under direct visualization at the back of the eye, the needle between the sclera and choroid, and the leading bleb in the sub retinal space between the choroid and a retina.
Figure 10F:
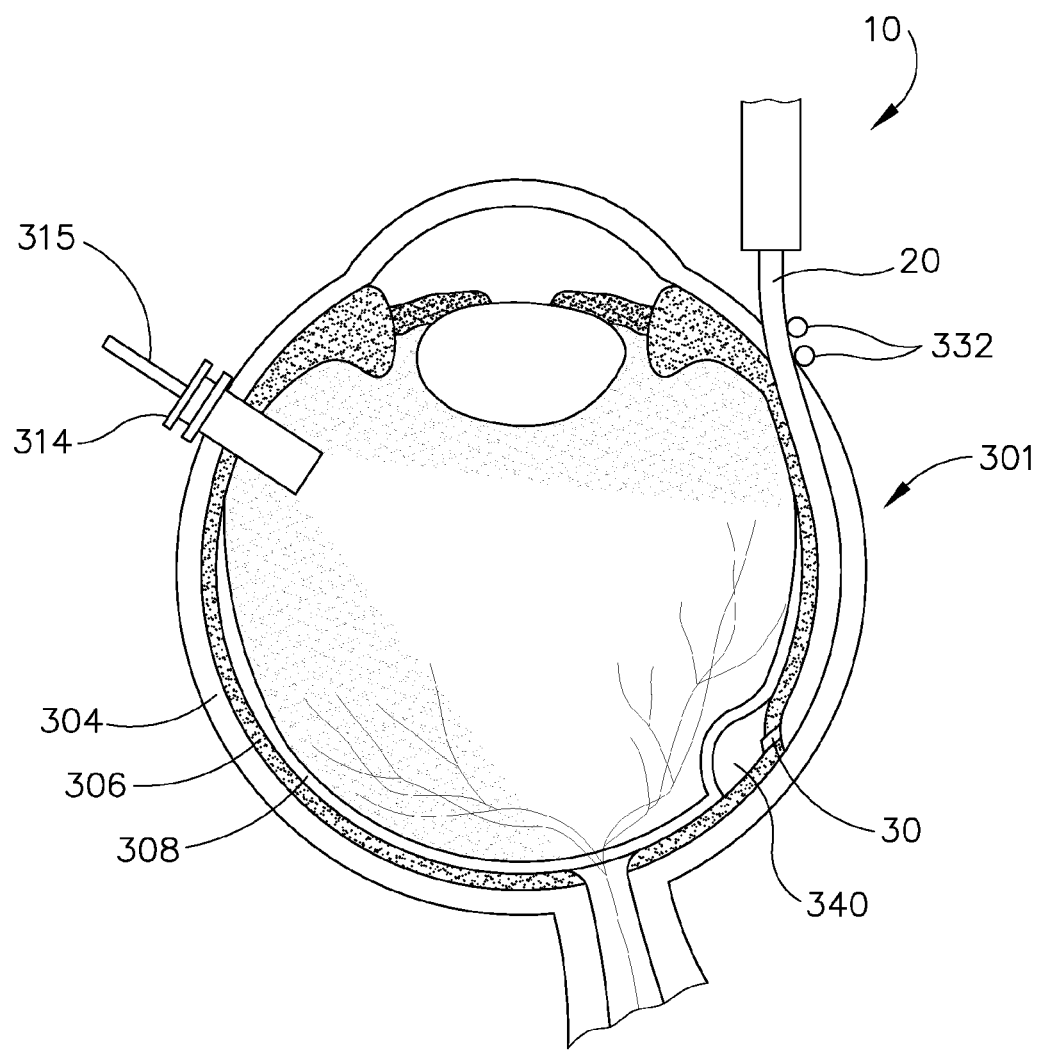
FIG. 10F depicts a cross-sectional view of the eye of FIG. 9A, with the cross-section taken about line 10E-10F of FIG. 9I.
Figure 11A:
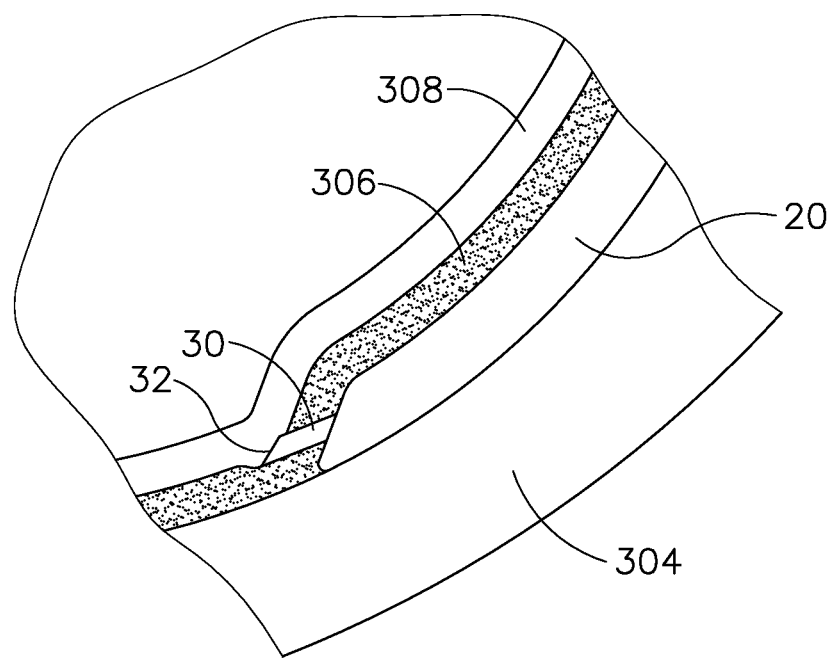
FIG. 11A depicts a detailed cross-sectional view of the eye of FIG. 9A depicted in the state shown in FIG. 10E.
Figure 11B:
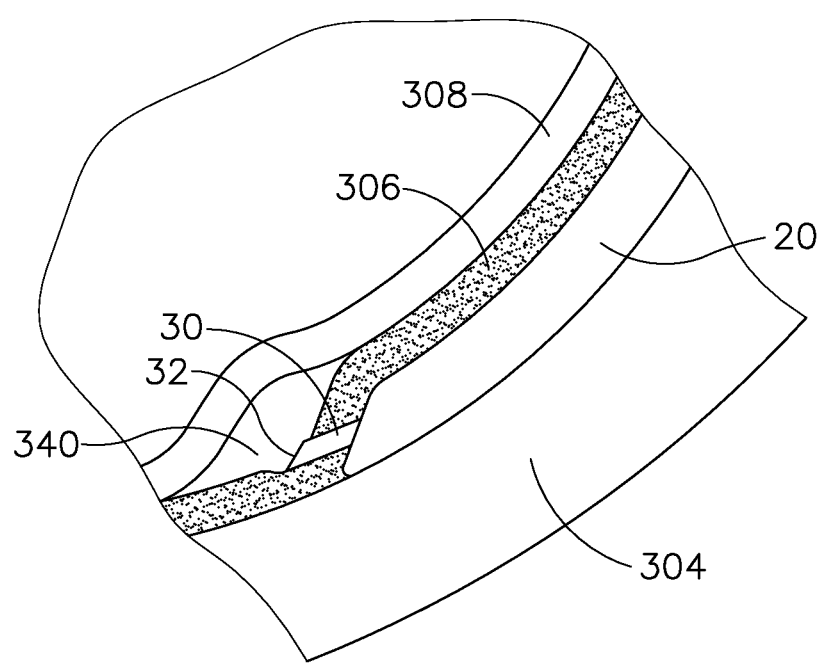
FIG. 11B depicts a detailed cross-sectional view of the eye of FIG. 9A depicted in the state shown in FIG. 10F.

In the present example, after the operator has confirmed that needle (30) has been properly advanced by visualizing the tenting effect described above, the operator infuses a balanced salt solution (BSS) or other similar solution as needle (30) is advanced relative to cannula (20). Such a BSS solution may form a leading bleb (340) ahead of needle (30) as needle (30) is advanced through choroid (306). Leading bleb (340) may be desirable for two reasons. First, as shown in FIGS. 9I, 10F, and 11B, leading bleb (340) may provide a further visual indicator to an operator to indicate when needle (30) is properly positioned at the delivery site. Second, leading bleb (340) may provide a barrier between needle (30) and retina (308) once needle (30) has penetrated choroid (306). Such a barrier may push the retinal wall outwardly (as is best seen in FIGS. 10F and 11B), thereby minimizing the risk of retinal perforation as needle (30) is advanced to the delivery site. In some versions, a foot pedal is actuated in order to drive leading bleb (340) out from needle (30). Alternatively, other suitable features that may be used to drive leading bleb (340) out from needle (30) will be apparent to those of ordinary skill in the art in view of the teachings herein.

Once the operator visualizes leading bleb (340), the operator may cease infusion of BSS, leaving a pocket of fluid as can be seen in FIGS. 9I, 10F, and 11B. Next, a therapeutic agent (341) may be infused by actuating a syringe or other fluid delivery device as described above with respect to instrument (10). The particular therapeutic agent (341) delivered may be any suitable therapeutic agent configured to treat an ocular condition. Some merely exemplary suitable therapeutic agents may include, but are not necessarily limited to, drugs having smaller or large molecules, therapeutic cell solutions, certain gene therapy solutions, and/or any other suitable therapeutic agent as will be apparent to those of ordinary skill in the art in view of the teachings herein. By way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein.

Figure 9J:
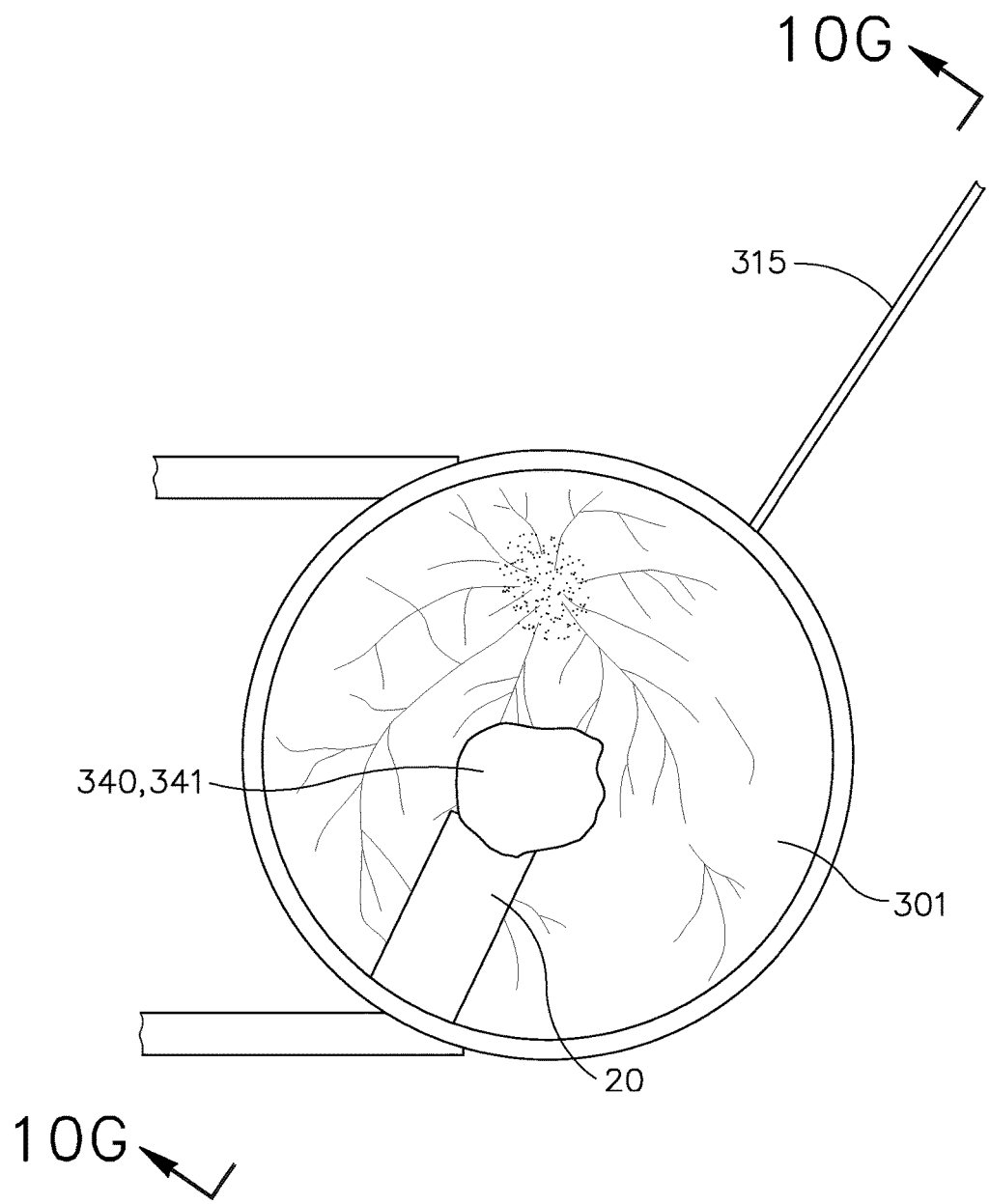
FIG. 9J depicts a top plan view of the eye of FIG. 9A, with the needle dispensing a therapeutic agent to the eye at the back of the eye, between the sclera and choroid.
Figure 10G:
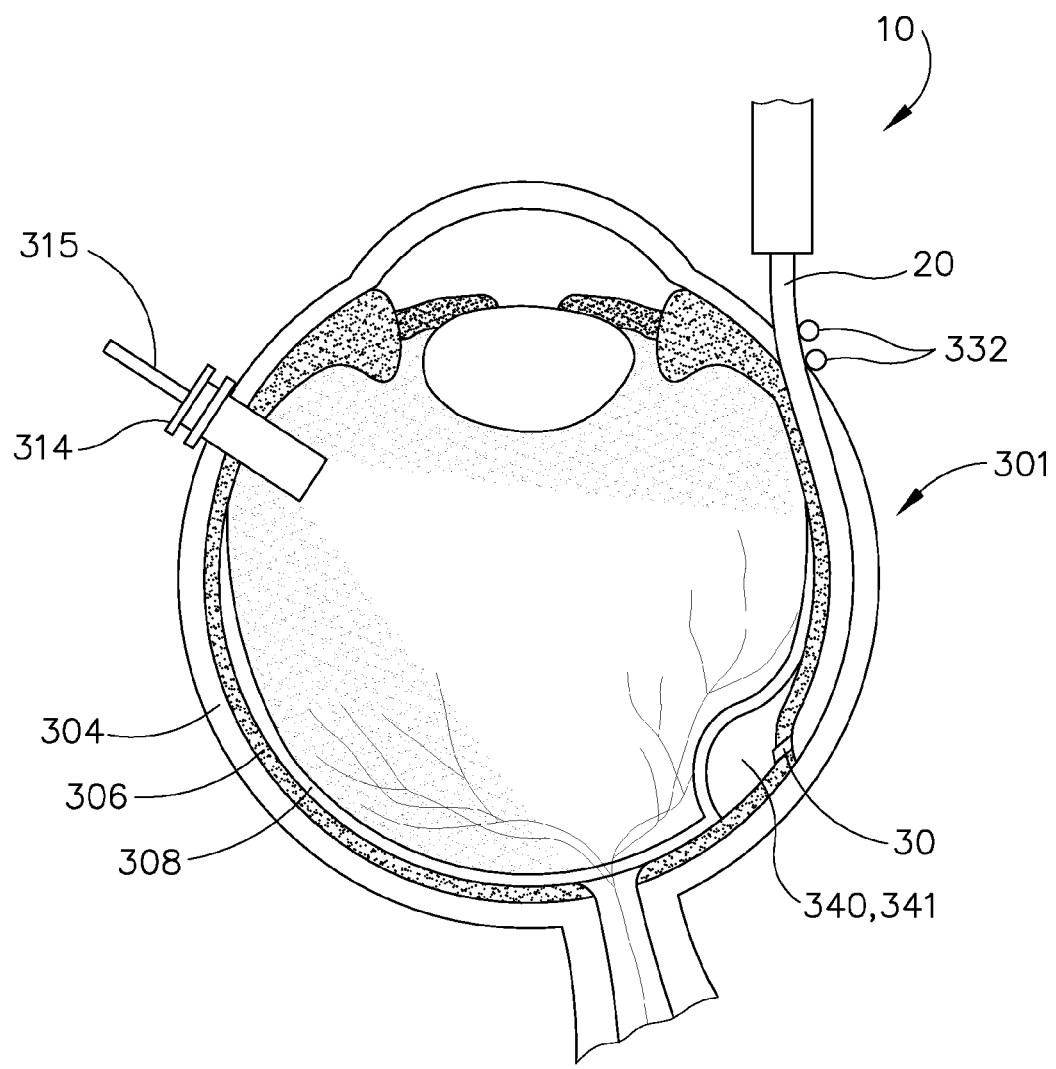
FIG. 10G depicts a cross-sectional view of the eye of FIG. 9A, with the cross-section taken about line 10G-10G of FIG. 9J.
Figure 11C:
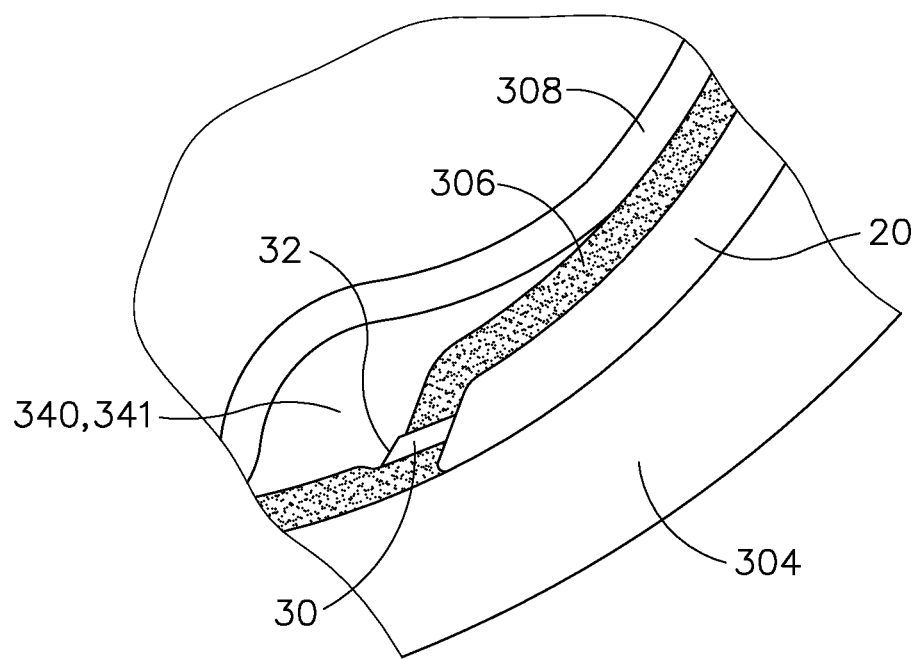
FIG. 11C depicts a detailed cross-sectional view of the eye of FIG. 9A depicted in the state shown in FIG. 10G.
Figure 12:
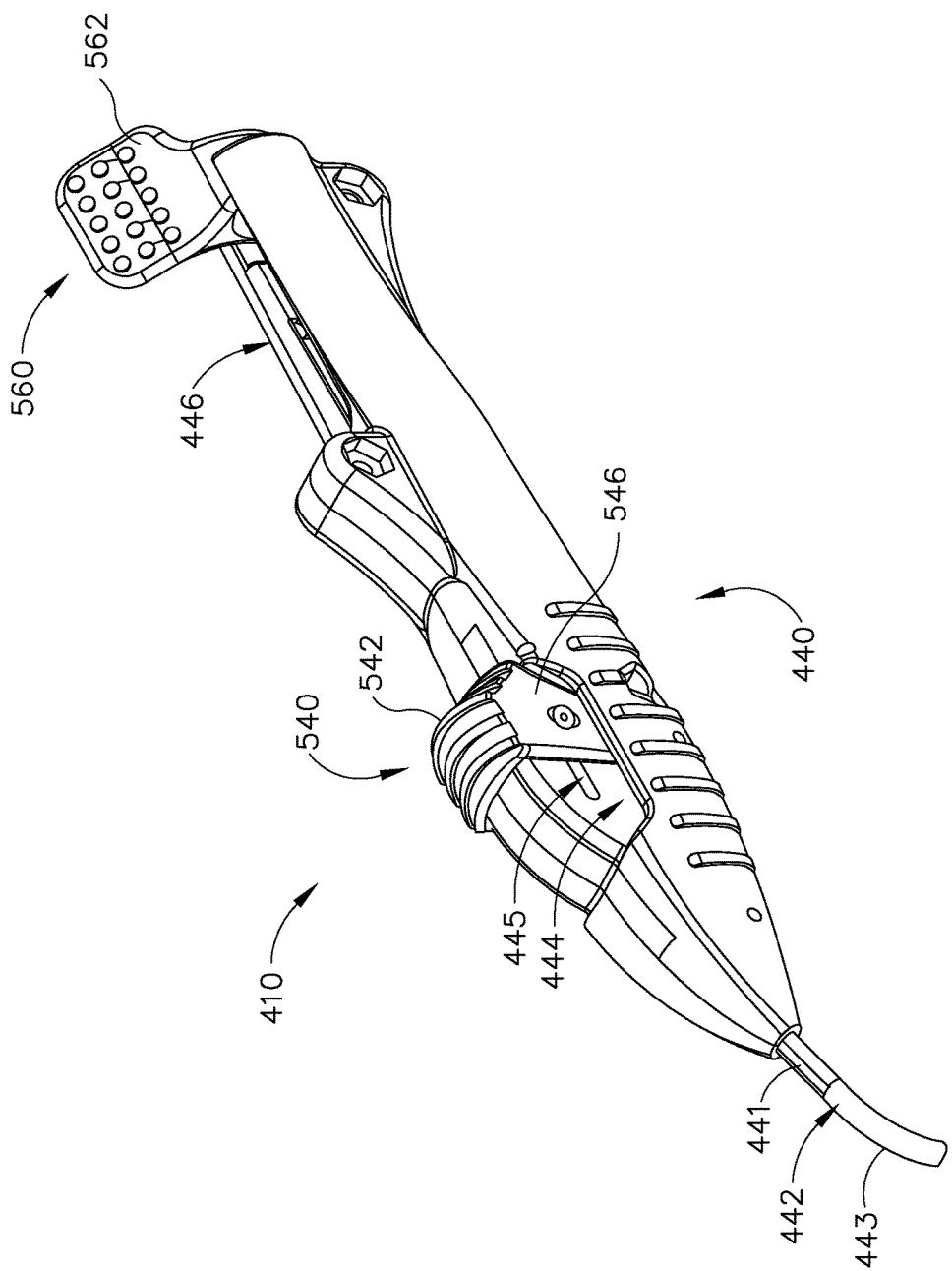
FIG. 12 depicts a perspective view of an exemplary alternative instrument for subretinal administration of a therapeutic agent from a suprachoroidal approach.
Figure 13:
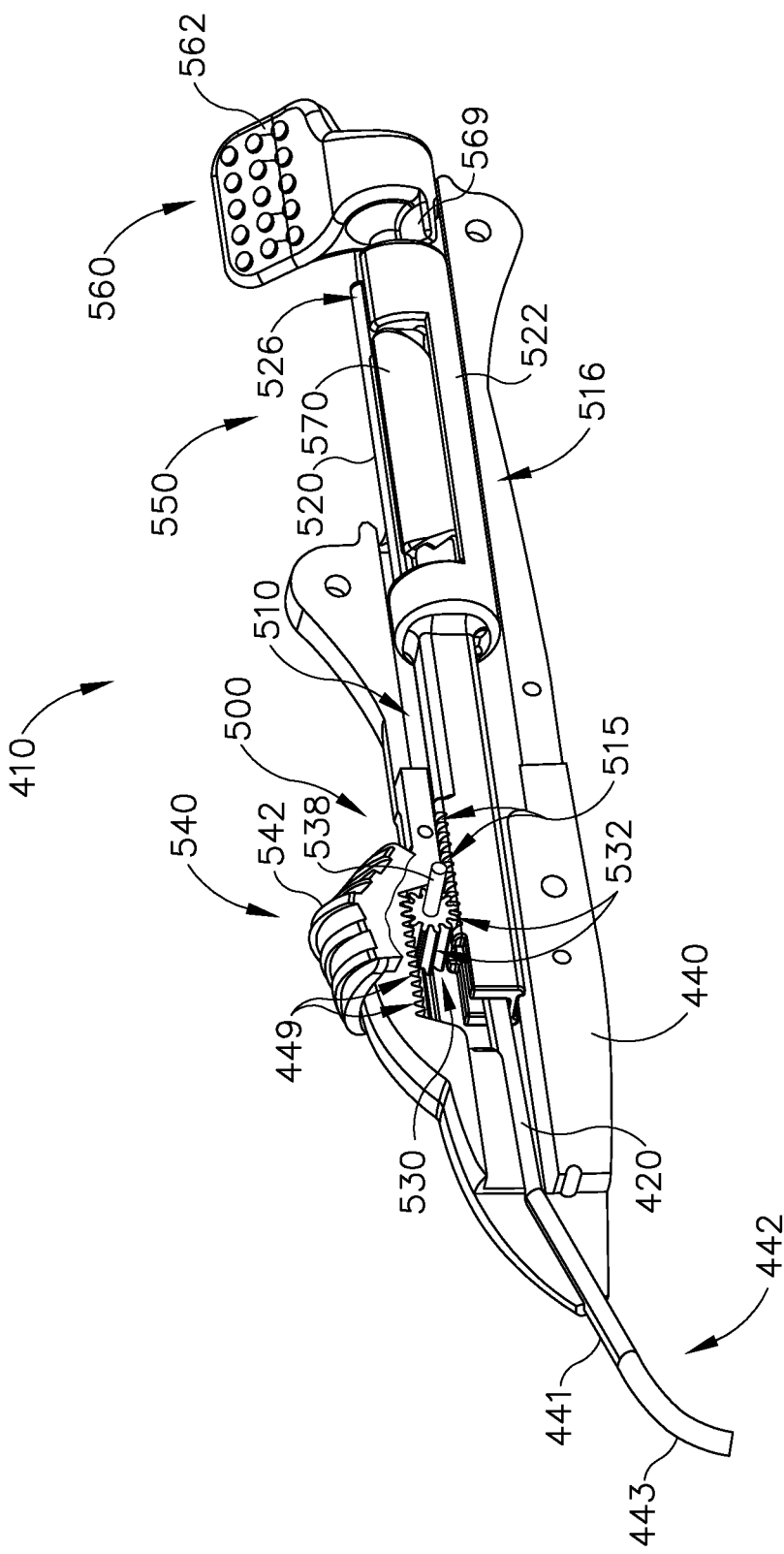
FIG. 13 depicts another perspective view of the instrument of FIG. 12, with a portion of a body removed.

In the present example, the amount of therapeutic agent (341) that is ultimately delivered to the delivery site is approximately 50 µL, although any other suitable amount may be delivered. In some versions, a foot pedal is actuated in order to drive agent (341) out from needle (30). Alternatively, other suitable features that may be used to drive agent (341) out from needle (30) will be apparent to those of ordinary skill in the art in view of the teachings herein. Delivery of therapeutic agent may be visualized by an expansion of the pocket of fluid as can be seen in FIGS. 9J, 10G, and 11C. As shown, therapeutic agent (341) essentially mixes with the fluid of leading bleb (340) as therapeutic agent (341) is injected into the suprachoroidal space.

Once delivery is complete, needle (20) may be retracted by sliding actuation assembly (60) proximally relative to body (40); and cannula (30) may then be withdrawn from eye (301). It should be understood that because of the size of needle (20), the site where needle (20) penetrated through choroid (306) is self sealing, such that no further steps need be taken to seal the delivery site through choroid (306). Suture loop assembly (330) and chandelier (314) may be removed, and incision (316) in the sclera (304) may be closed using any suitable conventional techniques.

As noted above, the foregoing procedure may be carried out to treat a patient having macular degeneration. In some such instances, the therapeutic agent (341) that is delivered by needle (20) may comprise cells that are derived from postpartum umbilicus and placenta. As noted above, and by way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. Alternatively, needle (20) may be used to deliver any other suitable substance or substances, in addition to or in lieu of those described in U.S. Pat. No. 7,413,734 and/or elsewhere herein. By way of example only, therapeutic agent (341) may comprise various kinds of drugs including but not limited to small molecules, large molecules, cells, and/or gene therapies. It should also be understood that macular degeneration is just one merely illustrative example of a condition that may be treated through the procedure described herein. Other biological conditions that may be addressed using the instruments and procedures described herein will be apparent to those of ordinary skill in the art.

V. Exemplary Alternative Instruments for Subretinal Administration of Therapeutic Agent from a Suprachoroidal Approach In some examples, it may be desirable to vary certain components or features of the instruments described herein. For instance, it may be desirable to utilize instruments similar to instrument (10) with alternative mechanisms to actuate needle (30). Additionally or in the alternative, it may be desirable to utilize instruments similar to instrument (10) with additional mechanisms to actuate cannula (20). Instruments having the above referenced variations may be desirable for different surgical procedures, or surgical procedures similar to the procedure discussed above, to engage tissue structures of having varying physical properties. While certain examples of variations are described herein, it should be understood that the instruments described herein may include any other alternative features as will be apparent to those of ordinary skill in the art in view of the teachings herein.

A. Exemplary Alternative Instrument with Lever Actuator

FIGS. 12-26C show an exemplary alternative instrument (410) that is similar to instrument (10) described above. It should be understood that instrument (410) may be readily used in place of instrument (10) to perform the medical procedure described above. It should also be understood that except as otherwise described herein, instrument (410) of this example is substantially the same as instrument (10) described above. Instrument (410) comprises a cannula (420), a body (440), a cannula guide (442) extending distally from body (440), a cannula actuation assembly (500) and a needle actuation assembly (550). Unlike instrument (10) described above, instrument (410) is generally configured to selectively advance both cannula (420) and a needle (430) relative to body (440). Cannula (420) and needle (430) are substantially the same as cannula (20) and needle (30) described above, such that further details will not be described herein.

Body (440) is generally shaped for grasping by the hand of an operator and to enclose the various components of cannula actuation assembly (500) and needle actuation assembly (550). To permit operation of cannula actuation assembly (500), body (440) includes two lever channels (444) and two actuation pin channels (445). Similarly, to permit operation of needle actuation assembly (550), body (440) includes a single actuator opening (446) defined proximally in body (440). As will be described in greater detail below, channels (444, 445) and opening (446) permit movement of various components of cannula actuation assembly (500) and needle actuation assembly (550) such that an operator may actuate such components to thereby advance cannula (420) and/or needle (430).

As described above, cannula guide (442) extends distally from body (440). In particular, cannula guide (442) includes a relatively straight proximal portion (441) and a generally curved distal portion (443). Proximal portion (441) extends distally from body (440) obliquely relative to the longitudinal axis of body (440). Distal portion (443) is shown as curving away from the longitudinal axis of body (440) at an increasing angle. It should be understood that the combination of proximal and distal portions (441, 443) is configured to orient cannula guide (442) at or near sclerotomy (316) or suture loop assembly (330) described above. Accordingly, as will be described in greater detail below, cannula guide (442) is operable to feed cannula (420) into a suitable position as cannula (420) is advanced distally relative to body (440). Although cannula guide (442) is shown and described as having a particular shape herein, it should be understood that in other examples cannula guide (442) may have any other suitable shape as will be apparent to those of ordinary skill in the art in view of the teachings herein.

Cannula guide (442) generally has a cross-sectional shape corresponding to the shape of cannula (420). For instance, as described above, cannula (420) has a generally rectangular cross-sectional shape. Accordingly, cannula guide (442) may also have a corresponding rectangular cross-sectional shape. Cannula guide (442) is generally hollow, or otherwise includes a lumen (not shown) such that cannula guide (442) is configured to slidably receive cannula (420). In addition to having a shape corresponding to cannula (420), cannula guide (442) also includes rounded edges such that cannula guide (420) is atraumatic in nature.

In the present example, cannula guide (442) is comprised of a generally rigid or semi-rigid material such that cannula guide (442) may maintain its shape as cannula (420) is advanced through cannula guide (442). Because cannula guide (442) is atraumatic and rigid or semi-rigid, it should be understood that when instrument is used in the method for suprachoroidal delivery of therapeutic agent described above, cannula guide (442) may be optionally rested or gently pressed against a patient's eye to generate leverage and to help ensure tangential advancement of cannula (420).

FIGS. 13-21 show cannula actuation assembly (500) and needle actuation assembly (550) in detail. In particular, cannula actuation assembly (500) and needle actuation assembly (550) can be seen fully assembled in FIG. 13, where one half of body (440) is removed. As can be seen, cannula actuation assembly (500) includes a cannula sled (510), a pinion gear (530), and a cannula advancement lever (540) (partially cutaway in FIG. 13). Likewise, needle actuation assembly (550) includes a needle advancement member (560) and a cam lock (570) disposed within cannula sled (510). As will be described in greater detail below, cannula actuation assembly (500) is actuated by an operator pressing cannula advancement lever (540) forward thereby causing cannula (420) and needle (430) to advance distally relative to body (440). Needle (430) is then advanced separately from cannula (420) by an operator first rotating needle advancement member (560) and then advancing needle advancement member (560) distally relative to body (440).

FIGS. 14-17 show various components of cannula actuation assembly (500) in detail and the relationship of these components to the rest of instrument (410). As will be described in greater detail below, cannula actuation assembly (500) is actuated via cannula advancement lever (540), which pivots to rotatably drive pinion gear (530). Pinion gear (530) then engages cannula sled (510) to translate cannula sled (510) relative to body (440).

Figure 15:
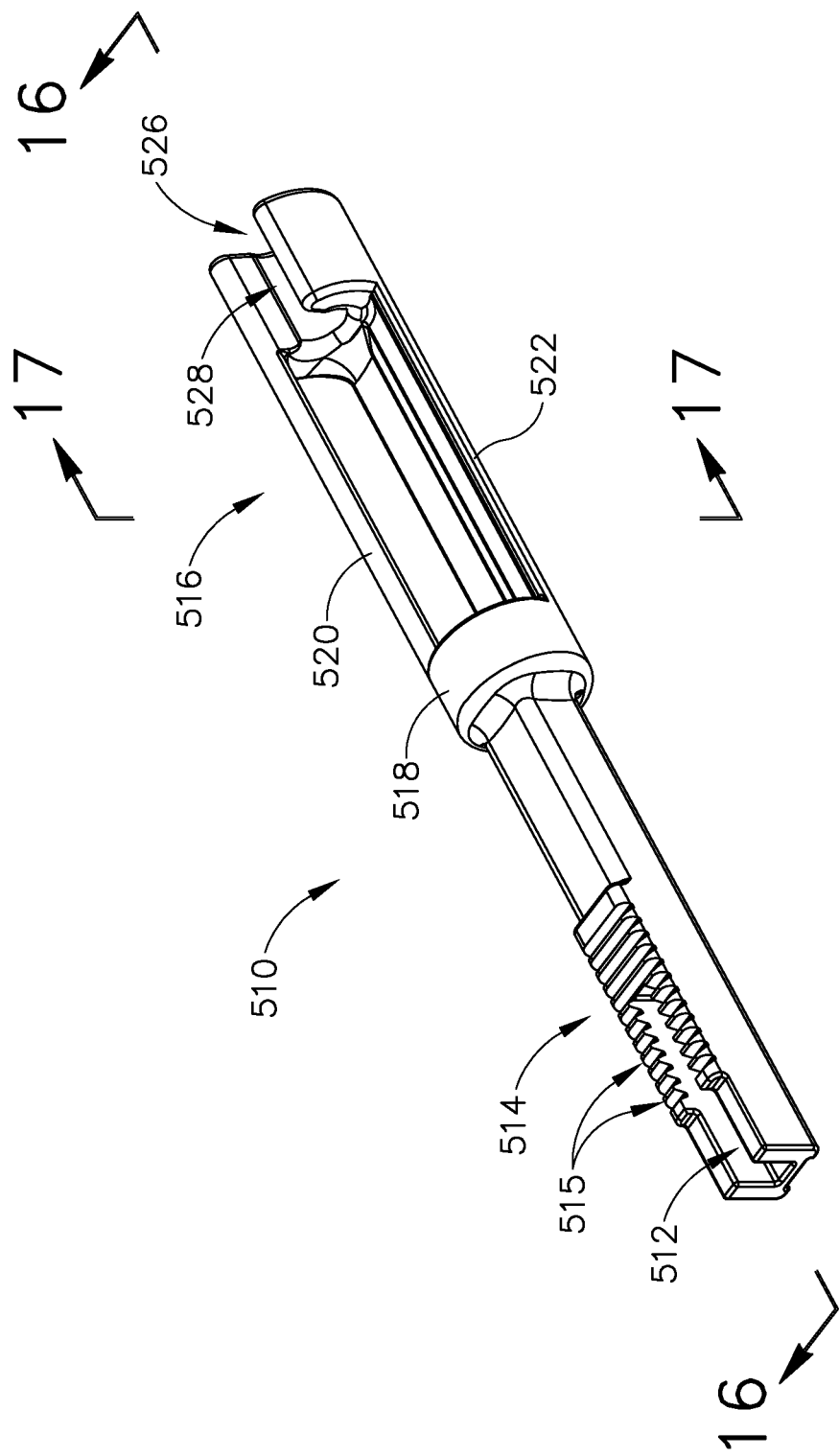
FIG. 15 depicts a perspective view of a cannula sled of the instrument of FIG. 12.
Figure 16:
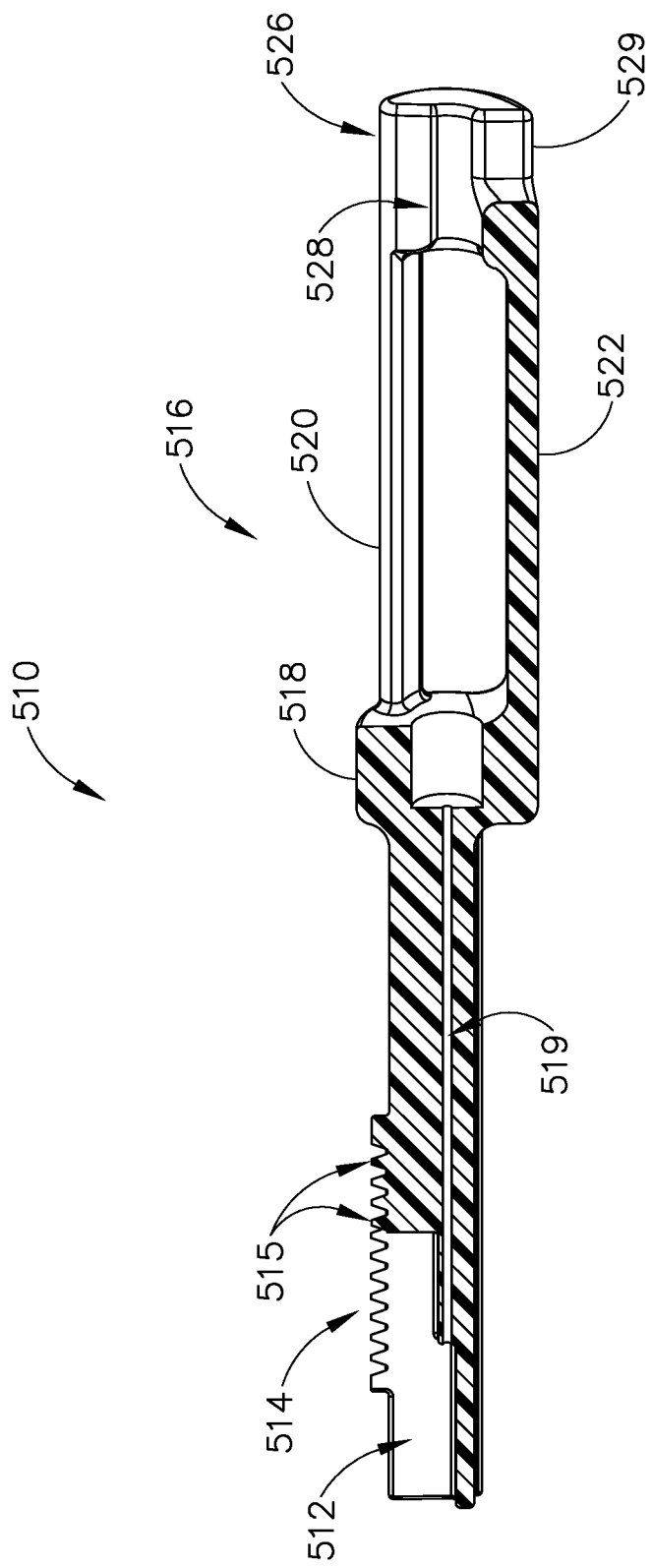
FIG. 16 depicts a side cross-sectional view of the cannula sled of the instrument of FIG. 12, the cross-section taken along line 16-16 of FIG. 15.
Figure 17:
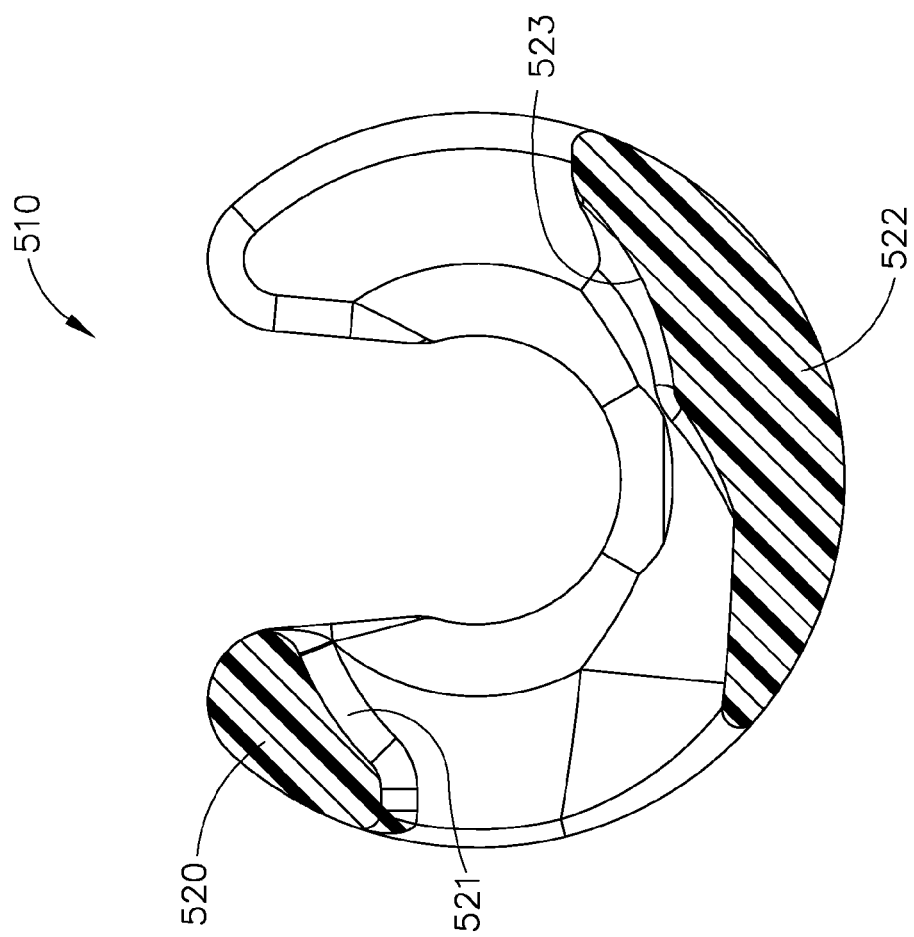
FIG. 17 depicts a cross-sectional front view of the cannula sled of the instrument of FIG. 12, the cross-section taken along line 17-17 of FIG. 15.

FIGS. 15-17 show detailed views of cannula sled (510). As can be seen in FIG. 15, cannula sled (510) comprises a cannula channel (512), a rack portion (514), a lock portion (516), and a needle advancement member receiving portion (526). Cannula channel (512) is configured to receive cannula (420) and is disposed within at least a portion of rack portion (514). As can be seen in FIG. 16, cannula channel (512) terminates in a needle lumen (519), which extends through cannula sled (510). Cannula (420) may be fixedly secured within cannula channel (512) by any suitable means such as adhesive boding, welding, mechanical fastening, and/or using any other suitable structures or techniques. Additionally, it should be understood that cannula channel (512) may include additional structural features configured to receive cannula (420). By way of example only, in some examples the proximal end of cannula (420) may include a flange or other similar structure, while cannula channel (512) may include a corresponding recess to further secure cannula (420) within cannula channel (512). Other suitable ways in which cannula (420) may be secured within cannula channel (512) will be apparent to those of ordinary skill in the art in view of the teachings herein.

Rack portion (514) comprises a plurality of teeth (515) that are spaced apart from each other along a linear, longitudinally extending path. A distal region of teeth (515) is separated into two laterally spaced apart regions, spaced apart by cannula channel (512). The particular size and spacing of teeth (515) corresponds to teeth (532) of pinion gear (530). Accordingly, teeth (515) of rack portion (514) are configured to mesh with teeth (532) of pinion gear (530) to form a rack and pinion mechanism. As will be described in greater detail below, such a mechanism drives translation of cannula sled (510) to actuate cannula (420).

Lock portion (516) of cannula sled (510) comprises a generally cylindrical body (518) with two longitudinally extending members (520, 522) formed integrally therein. As can best be seen in FIG. 17, each longitudinally extending member (520, 522) includes a respective interior camming surface (521, 523). As will be described in greater detail below, camming surfaces (521, 523) are configured to selectively engage with cam lock (570) of needle actuation assembly (550) to lock cannula sled (510) in a particular longitudinal position relative to body (440) of instrument (410).

Needle advancement member receiving portion (526) is positioned proximally of longitudinally extending members (520, 522). Needle advancement member receiving portion (526) includes a rounded upper receiving channel (528) (best seen in FIG. 15) and a rectangular lower receiving channel (529) (best seen in FIG. 16). As will be described in greater detail below, upper receiving channel (528) is configured to receive a corresponding elongate cylindrical portion (566) of needle advancement member (560). Similarly, lower receiving channel (529) is configured to receive a corresponding lock tab (569) of needle advancement member (560). Although receiving channels (528, 529) are shown as having a particular shape, it should be understood that in other examples the shape of receiving channels (528, 529) may be altered depending on the particular geometry of needle advancement member (560).

Returning to FIG. 14, pinion gear (530) is shown as comprising a generally cylindrical body with a plurality of teeth (532) extending outwardly therefrom. The body of pinion gear (530) further includes a bore extending therethrough. The bore is configured to receive pinion gear pin (538). As will be described in greater detail below, pinion gear pin (538) is received within the bore to rotatably couple pinion gear (530) to cannula advancement lever (540).

Figure 14:
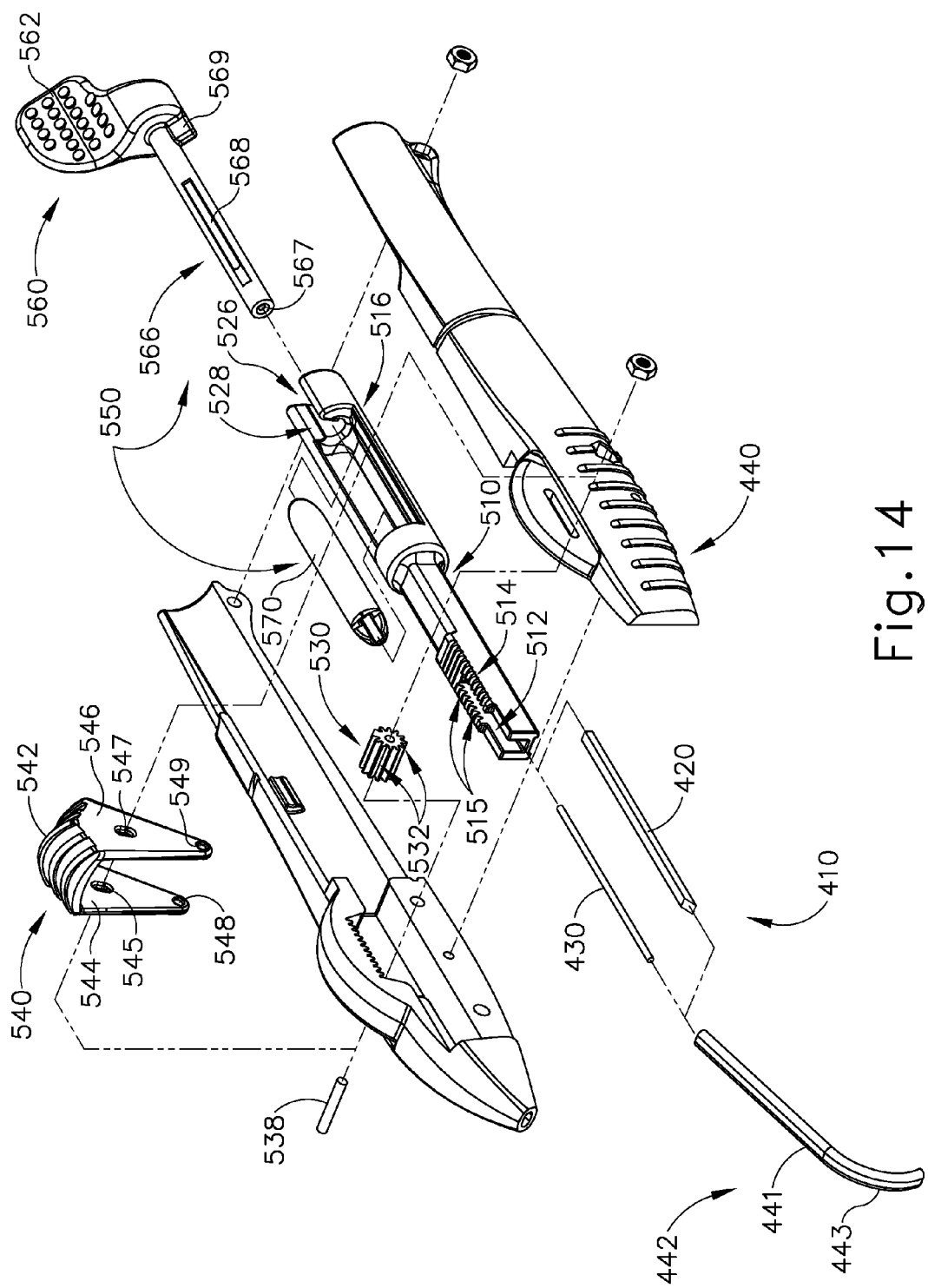
FIG. 14 depicts an exploded perspective view of the instrument of FIG. 12.

Cannula advancement lever (540) is also shown in FIG. 14. As can be seen, lever (540) comprises a grip portion (542) and two arms (544, 546) extending away from grip portion (542). Each arm (544, 546) comprises a respective pin slot (545, 547) that is configured to receive pinion gear pin (538). Pin slots (545, 547) are elongate in shape, permitting some degree of vertical travel of pinion gear pin (538) in each pin slot (545, 547). Each arm (544, 546) further comprises a respective attachment opening (548, 549) which is rotatably secured within lever channels (444) of body (440) (see FIG. 12).

FIGS. 14 and 18-22 show needle actuation assembly (550) in detail and the relationship of needle actuation assembly (550) to the rest of instrument (410). As will be described in greater detail below, needle actuation assembly (550) is generally configured to translate with cannula actuation assembly (500) until cannula actuation assembly (500) is locked in place by needle actuation assembly (550), thereby permitting needle (430) to be advanced relative to cannula (420).

Figure 18:
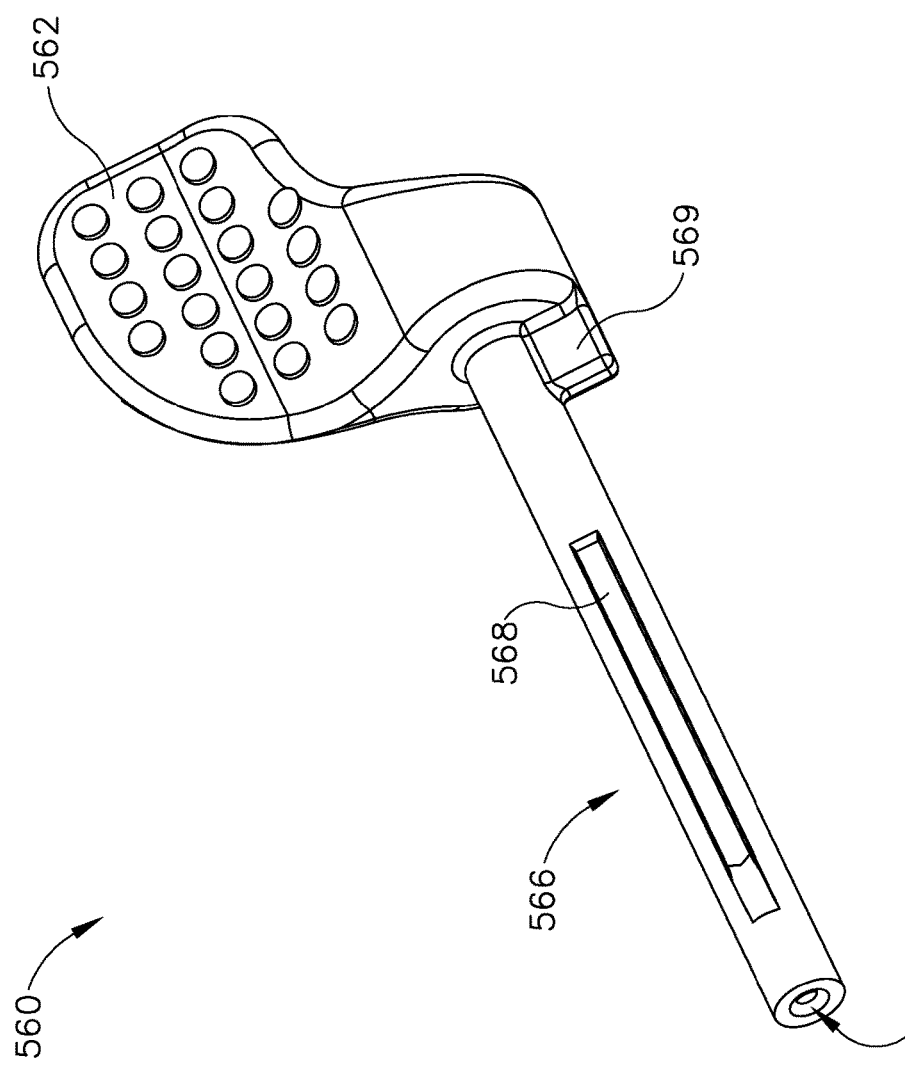
FIG. 18 depicts a perspective view of a needle advancement member of the instrument of FIG. 12.
Figure 19:
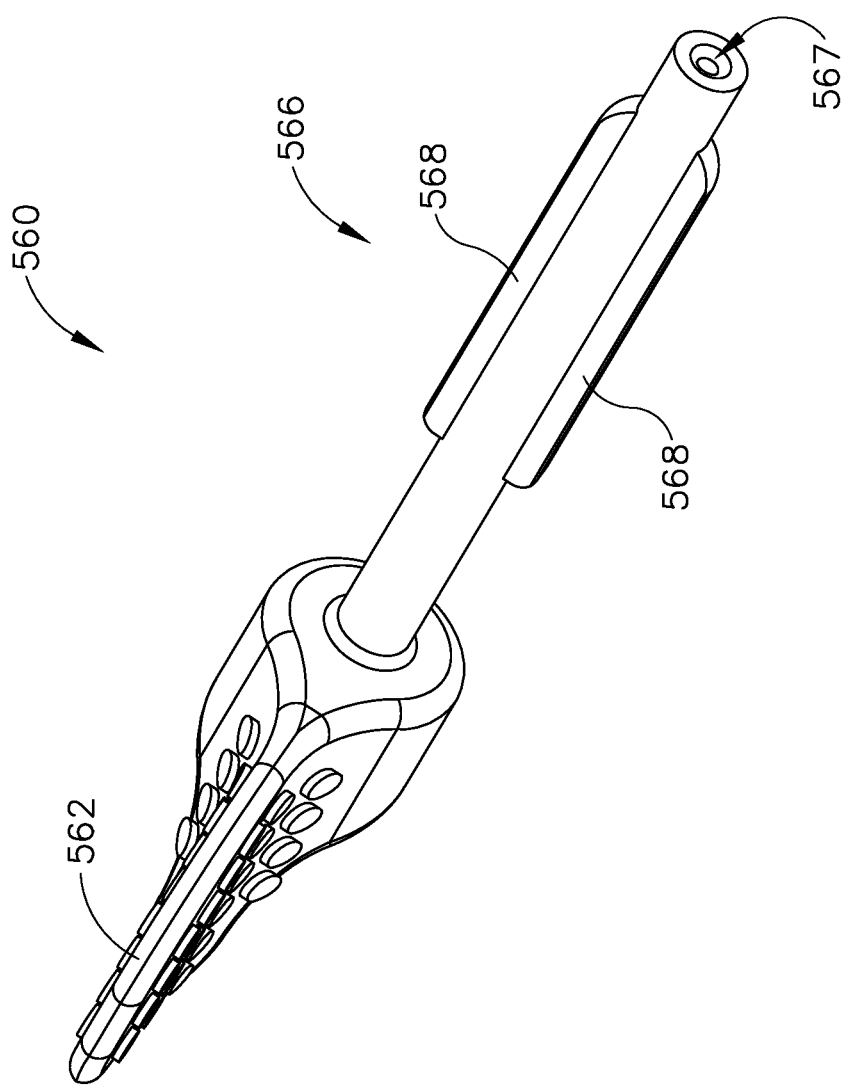
FIG. 19 depicts another perspective view of the needle advancement member of FIG. 18.

As described above, needle actuation assembly (550) comprises needle advancement member (560) and cam lock (570). Detailed views of needle advancement member (560) are shown in FIGS. 18 and 19. As can be seen, needle advancement member (560) comprises an actuation tab (562) and an elongate cylindrical portion (566) extending therefrom. Actuation tab (562) has a tab-like shape and is configured for grasping by an operator. Although actuation tab (562) of the present example is shown as having a tab-like shape, it should be understood that in other examples actuation tab (562) may take on any other shape suitable for grasping. Actuation tab (562) further includes a lock tab (569). Lock tab (569) is generally rectangular in shape and is disposed at the interface between actuation tab (562) and elongate cylindrical portion (566). As will be described in greater detail below, lock tab (569) is configured to prevent translation of needle (430) relative to cannula (420) when needle actuation assembly (550) is positioned in a locked position.

As can best be seen in FIG. 19, elongate cylindrical portion (566) includes a pair of elongate protrusions (568) in the form of fins extending outwardly from elongate cylindrical portion (566). As will be described in greater below, elongate protrusions (568) are configured to slidably engage a corresponding pair of elongate channels (574) defined within the interior of cam lock (570) such that elongate cylindrical portion (566) is operable to rotate cam lock (570) yet translate relative to cam lock (570). While elongate cylindrical portion (566) is shown as being generally cylindrical with elongate protrusions (568) protruding outwardly from elongate cylindrical portion (566), in other examples similar functionality of elongate cylindrical portion (566) may be accomplished using other configurations. For instance, in other examples elongate protrusions (568) may be omitted. In lieu of elongate protrusions (568), elongate cylindrical portion (566) may comprise an irregular cross-sectional shape such as hexagonal, ovular, triangular, etc. Of course, in such configurations shape of cam lock (570) would also be modified accordingly to correspond to the cross-sectional shape of elongate cylindrical portion (566).

Elongate cylindrical portion (566) further comprises a lumen (567) extending therethrough. Lumen (567) is configured to receive needle (430). It should be understood that lumen (567) may extend through the proximal end of needle advancement member (560) to thereby permit lumen (567) to receive a supply tube or multiple supply tubes. Accordingly, it should be understood that needle advancement member (560) is configured to act as a needle coupling device to thereby couple needle (430) to needle advancement member (560) and/or the supply tube or tubes. In some examples, needle (430) may be fixedly secured to needle advancement member (560) such that any rotational or translational movement of needle advancement member (560) is transferred to needle (430). In other examples, needle (430) may be merely translationally fixed relative to needle advancement member (560) such that only translational movement of needle advancement member (560) is transferred to needle (430), while needle (430) remains rotationally independent of needle advancement member (560). Various suitable configurations for coupling needle (430) to needle advancement member (560) to achieve the desired functionality described herein will be apparent to those of ordinary skill in the art in view of the teachings herein.

Figure 22:
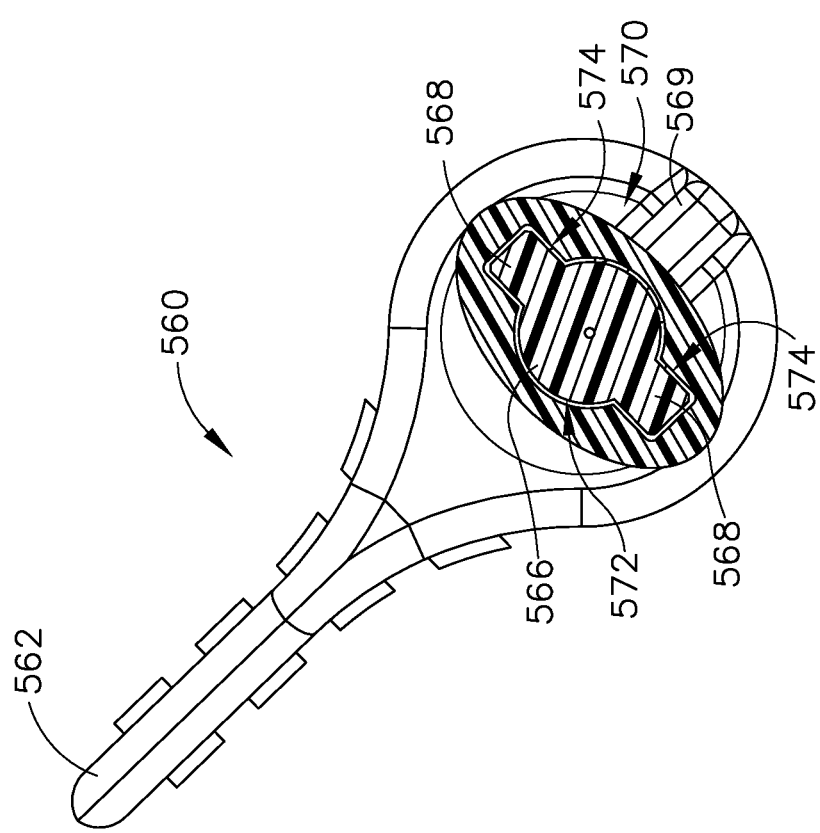
FIG. 22 depicts a front cross-sectional view of the cam lock of FIG. 20 disposed about the cannula sled of FIG. 15.
Figure 23C:
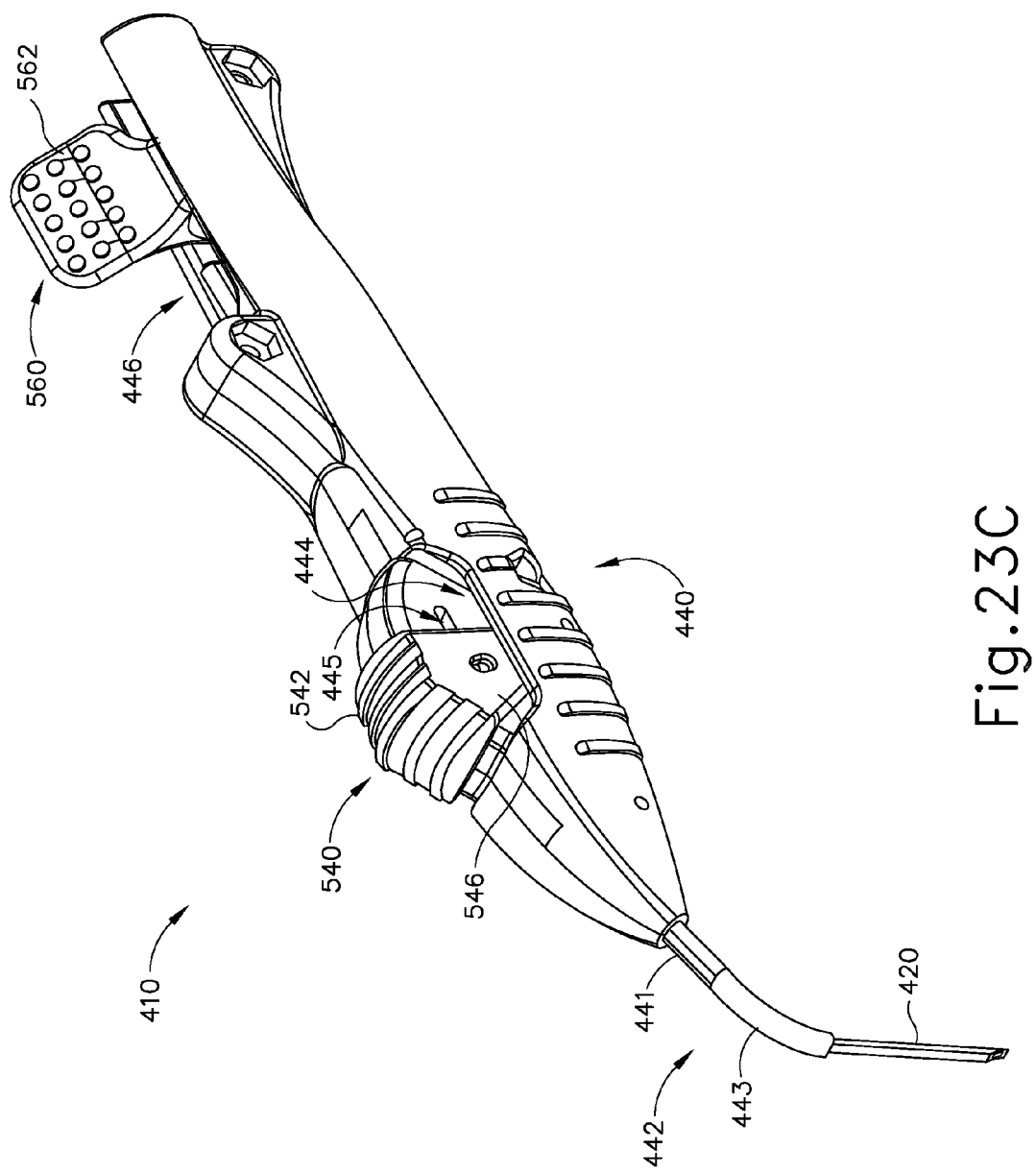
FIG. 23C depicts yet another perspective view of the instrument of FIG. 12, with the cannula fully advanced and the needle locked and retracted.
Figure 23D:
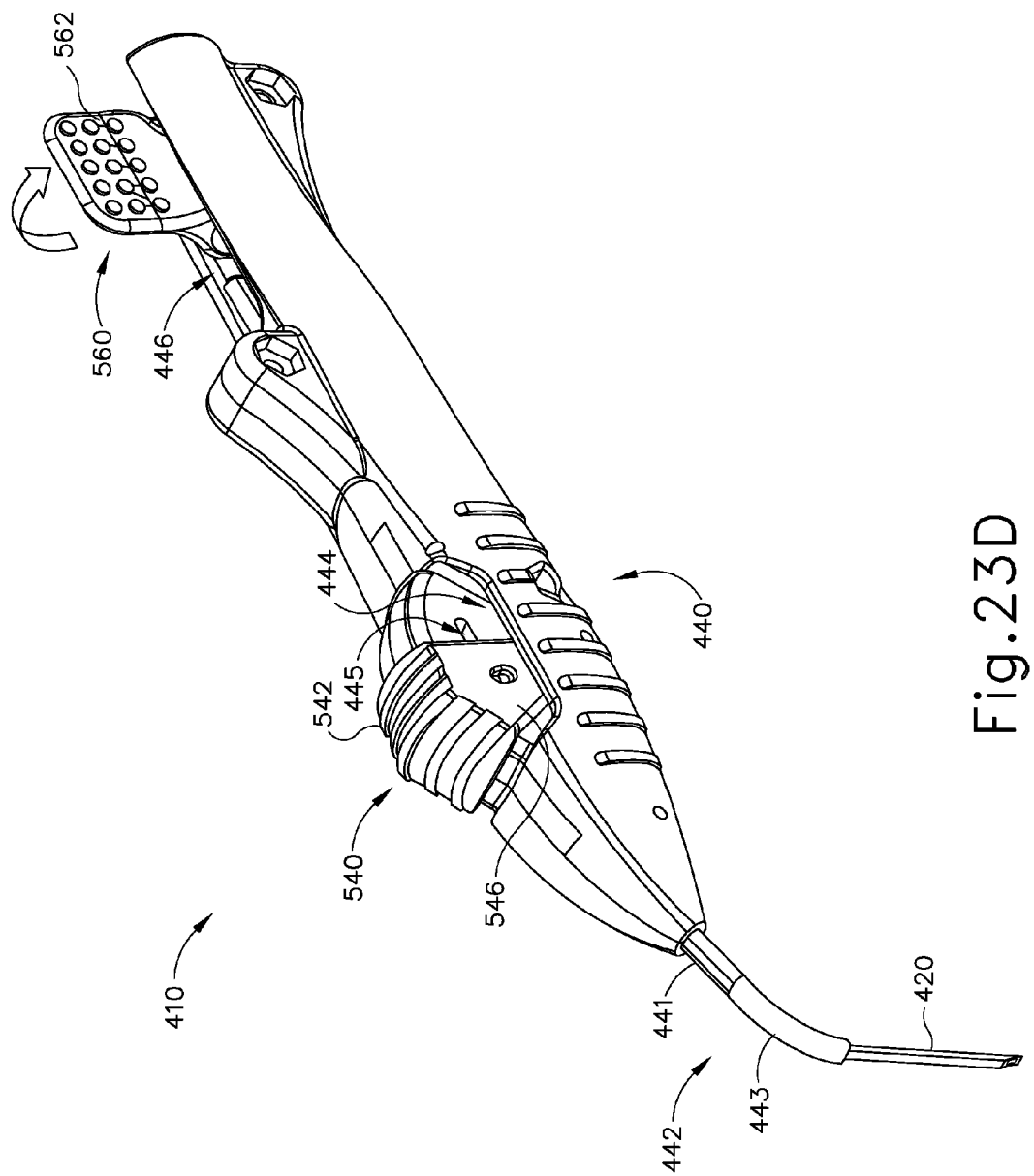
FIG. 23D depicts yet another perspective view of the instrument of FIG. 12, with the cannula fully advanced and the needle unlocked yet retracted.
Figure 23E:
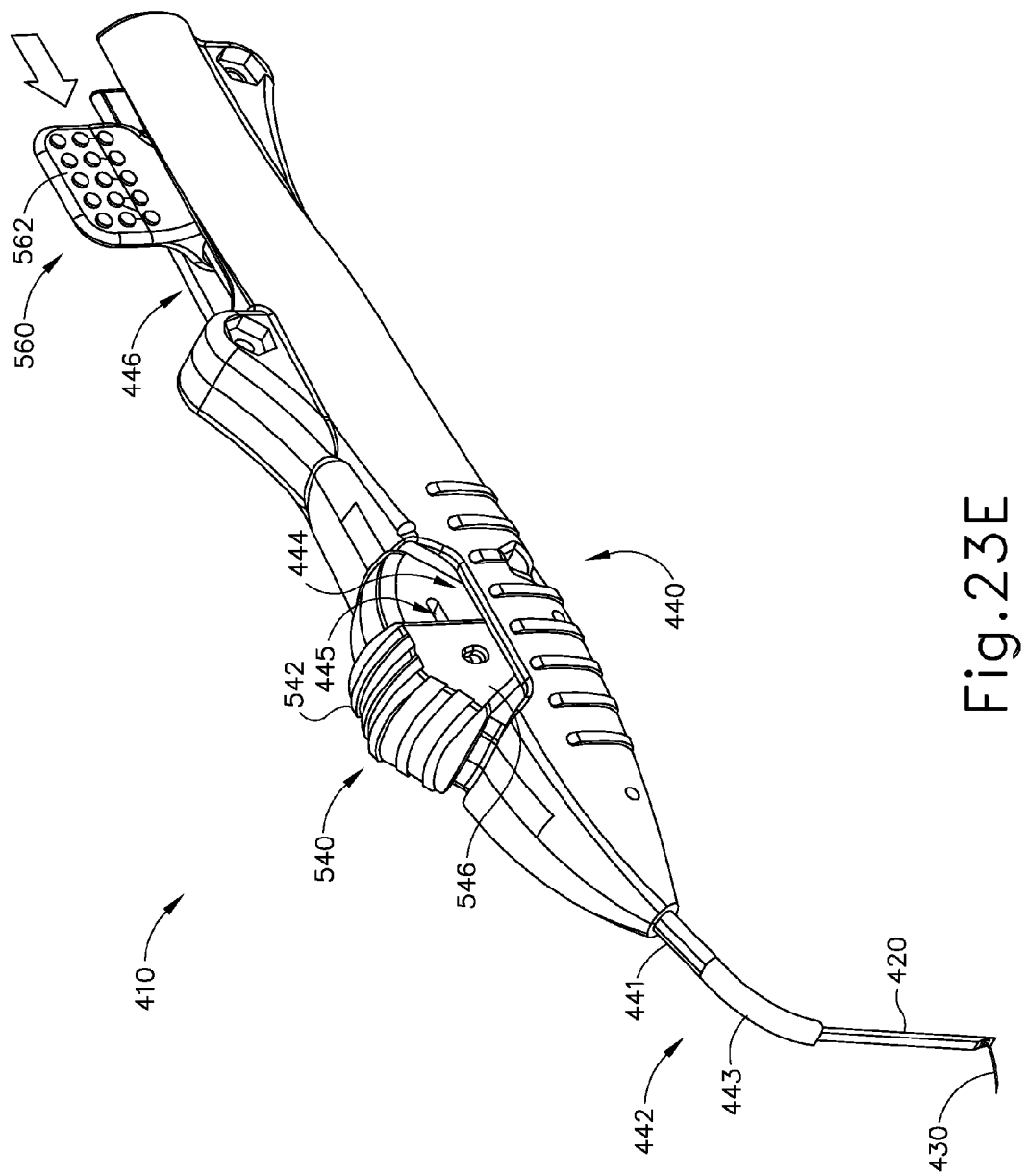
FIG. 23E depicts yet another perspective view of the instrument of FIG. 12, with the cannula and needle in an advanced position.

Cam lock (570) is best seen in FIGS. 20 and 21. As can be seen, cam lock (570) comprises an elongate structure with a generally elliptical cross-sectional shape. Cam lock (570) further defines a lumen (572) extending through cam lock (570). Lumen (570) is generally circular in shape with a pair of elongate channels (574) defined by cam lock (570) on opposing sides of lumen (572). As can be seen in FIG. 22 and as was described above, lumen (572) and channels (574) are configured to slidably receive elongate cylindrical portion (566) and elongate protrusions (568) of needle advancement member (560). Thus, it should be understood that when an operator rotates needle advancement member (560) via actuation tab (562), cam lock (570) will correspondingly rotate unitarily with elongate cylindrical portion (566). Yet when needle advancement member (560) is translated relative to instrument (410), cam lock (570) may remain stationary relative to needle advancement member (560).

FIGS. 23A-26C show an exemplary mode of operation using instrument (410). In particular, instrument (410) begins in the state shown in FIGS. 23A and 24A. As can be seen, cannula actuation assembly (500) and needle actuation assembly (550) are initially both in a retracted proximal position relative to body (440). In this position, cannula advancement lever (540) is retracted proximally relative to body (440). Correspondingly, cannula sled (510) and pinion gear (530) are positioned proximally within body (440). Because cannula (420) is fixedly secured to cannula sled (510), cannula (420) is similarly disposed proximally relative to body (440) such that cannula (420) is disposed within cannula guide (442). In this position, needle (430) is also in a proximal position such that the distal tip of needle (430) is disposed within cannula (442).

Figure 24A:
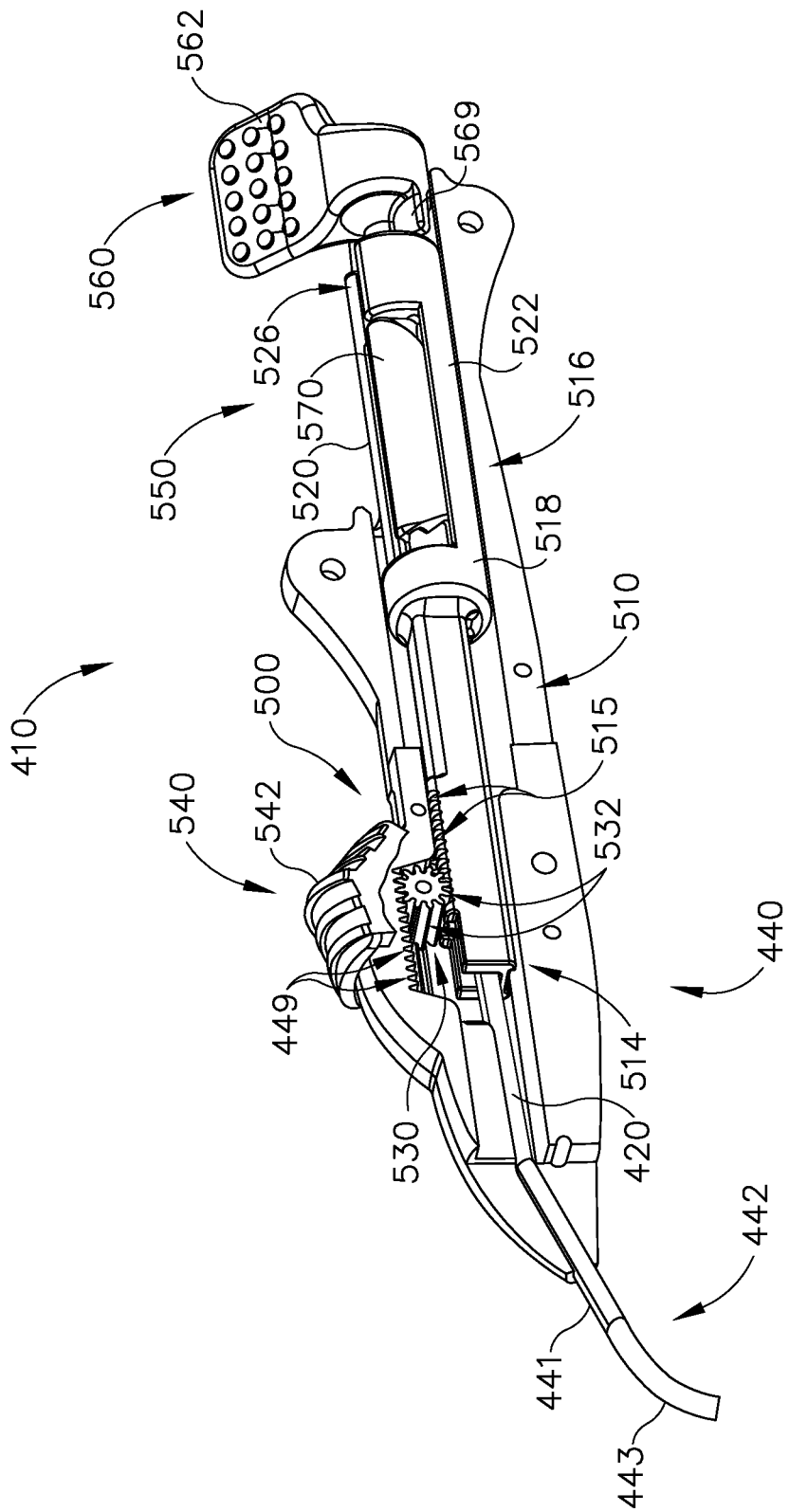
FIG. 24A depicts yet another perspective view of the instrument of FIG. 12, with a housing of the instrument removed and the cannula and needle in a retracted position.
Figure 24B:
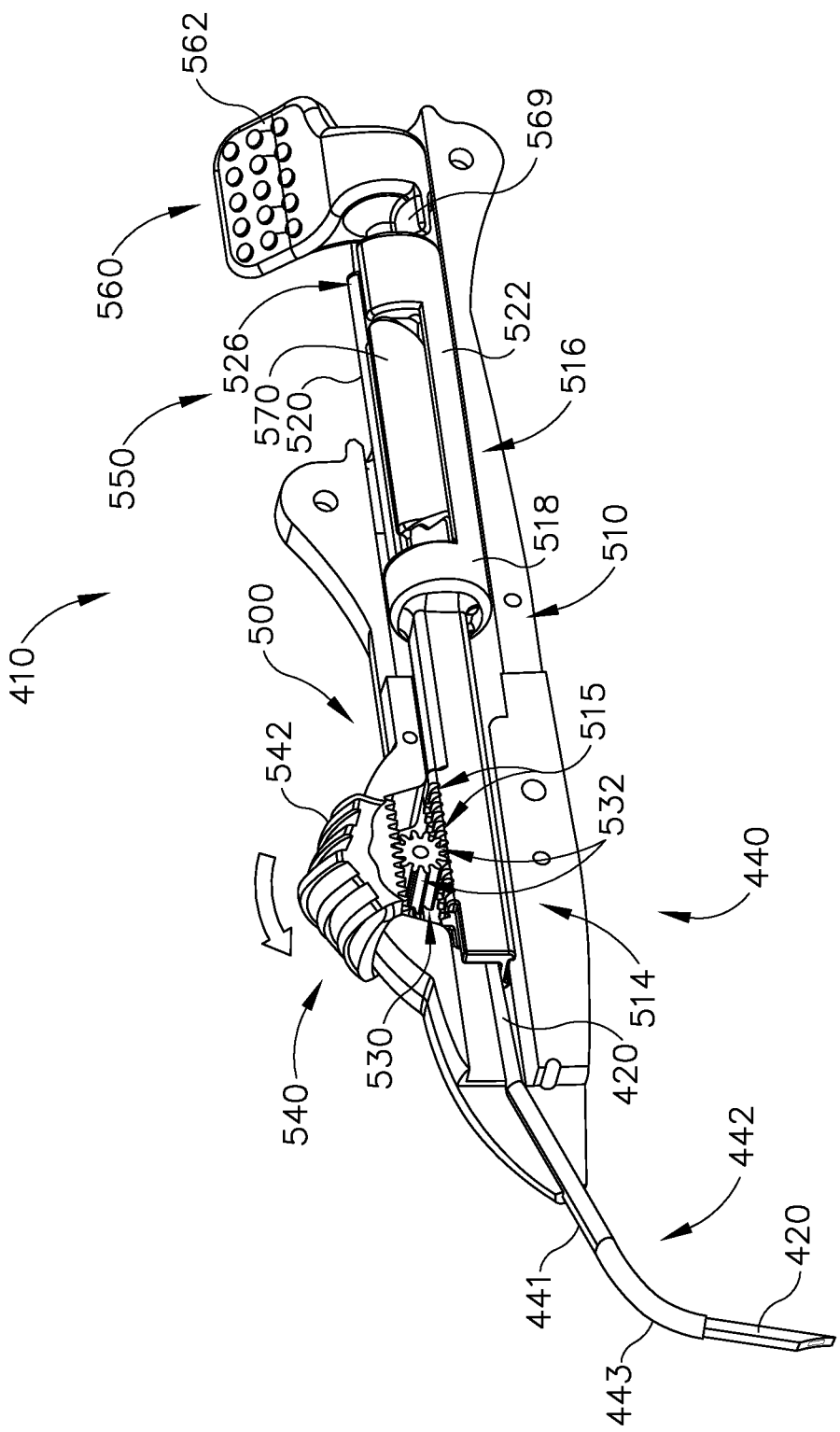
FIG. 24B depicts yet another perspective view of the instrument of FIG. 12, with a housing of the instrument removed and the cannula partially advanced and the needle locked and retracted.

To initiate advancement of cannula (420), an operator may apply a force to cannula advancement lever (540) to pivot cannula advancement lever (540) distally relative to body (440), as can be seen in FIGS. 23B and 24B. Because pinion gear (530) is rotatably attached to cannula advancement lever (540) via pinion gear pin (538), advancement of cannula advancement lever (540) will cause pinion gear (530) to correspondingly advance along a linear path. As pinion gear (530) advances linearly, teeth (532) of pinion gear (530) will engage teeth (515) of cannula sled (510). Additionally, teeth (532) of pinion gear (530) will also engage corresponding teeth (449) that are integral to body (440). Thus, linear movement of pinion gear (530) will initiate clockwise rotation of pinion gear (530) via engagement between teeth (532) of pinion gear (530) and teeth (449) of body (440). Clockwise rotation of pinion gear (530) will then initiate distal translation of cannula sled (510) via engagement between teeth (532) pinion gear (530) and teeth (515) of cannula sled (510). Because cannula (420) is fixedly secured to cannula sled (510), advancement of cannula sled (510) will result in corresponding advancement of cannula (420). As cannula sled (510) is advanced, needle advancement assembly (550) may also incidentally advance with cannula sled (510) due to friction between the various parts of needle advancement assembly (550) and cannula sled (510).

Figure 24C:
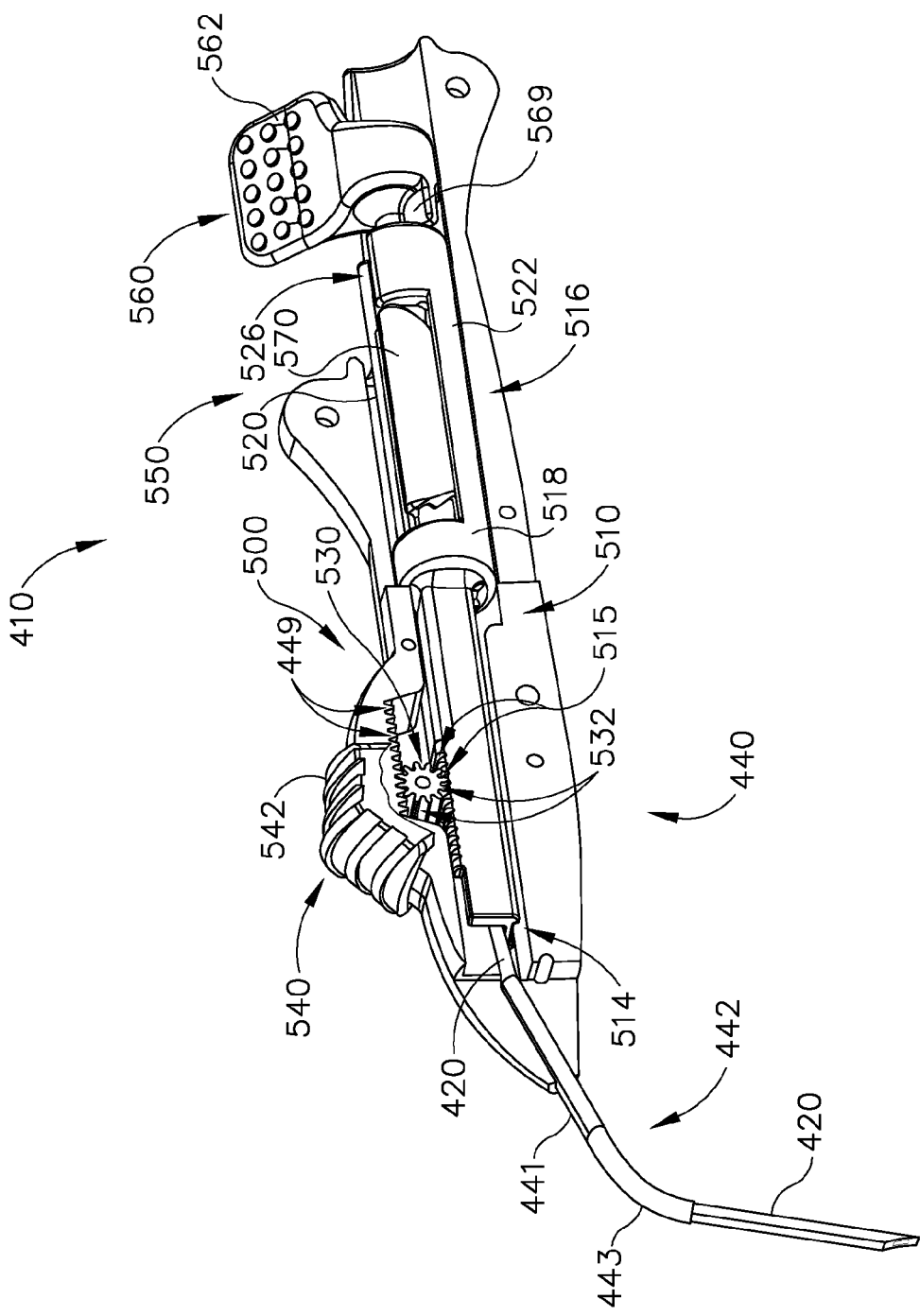
FIG. 24C depicts yet another perspective view of the instrument of FIG. 12, with a housing of the instrument removed and the cannula fully advanced and the needle locked and retracted.
Figure 24D:
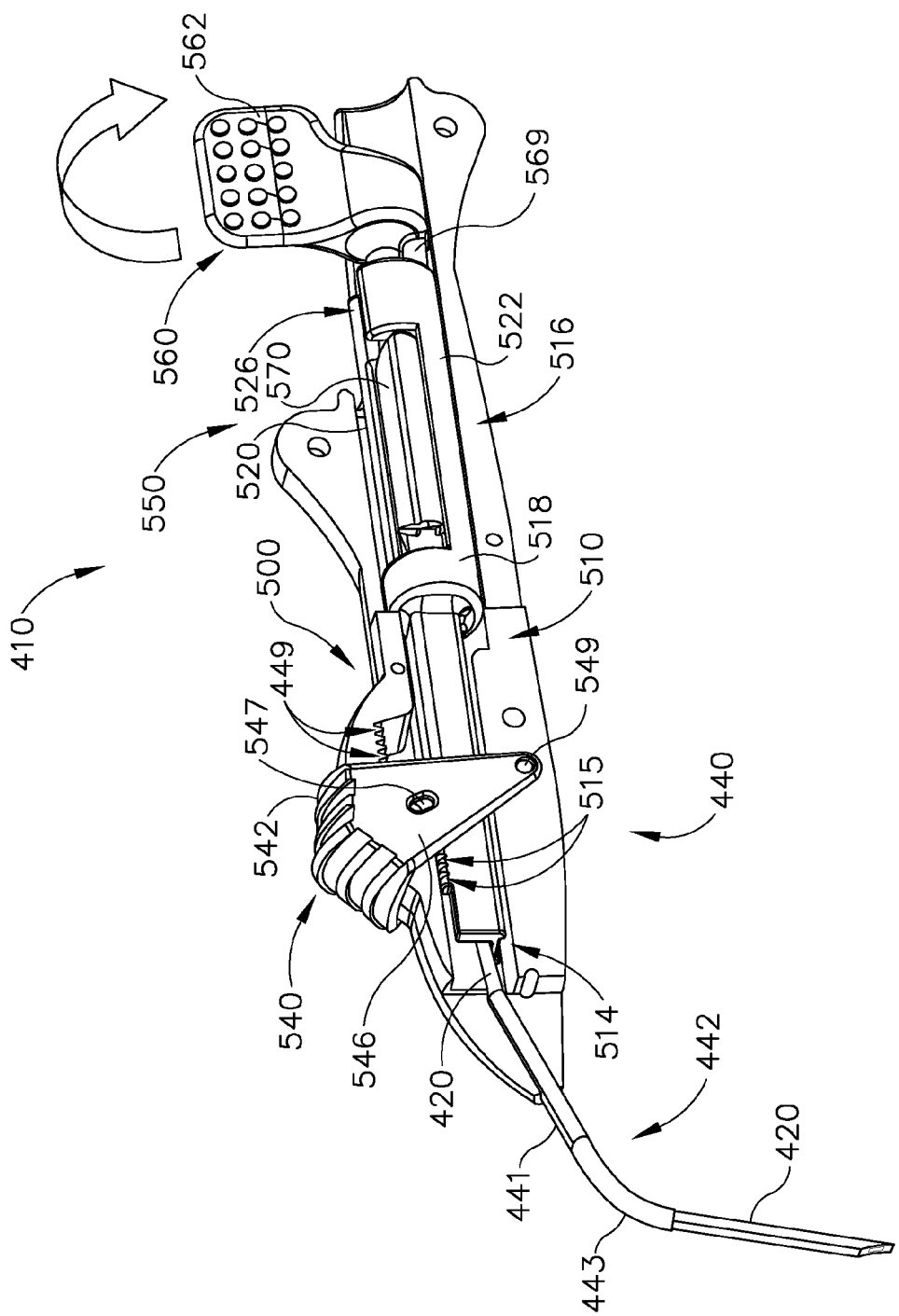
FIG. 24D depicts yet another perspective view of the instrument of FIG. 12, with a housing of the instrument removed and the cannula fully advanced and the needle unlocked yet retracted.
Figure 25A:
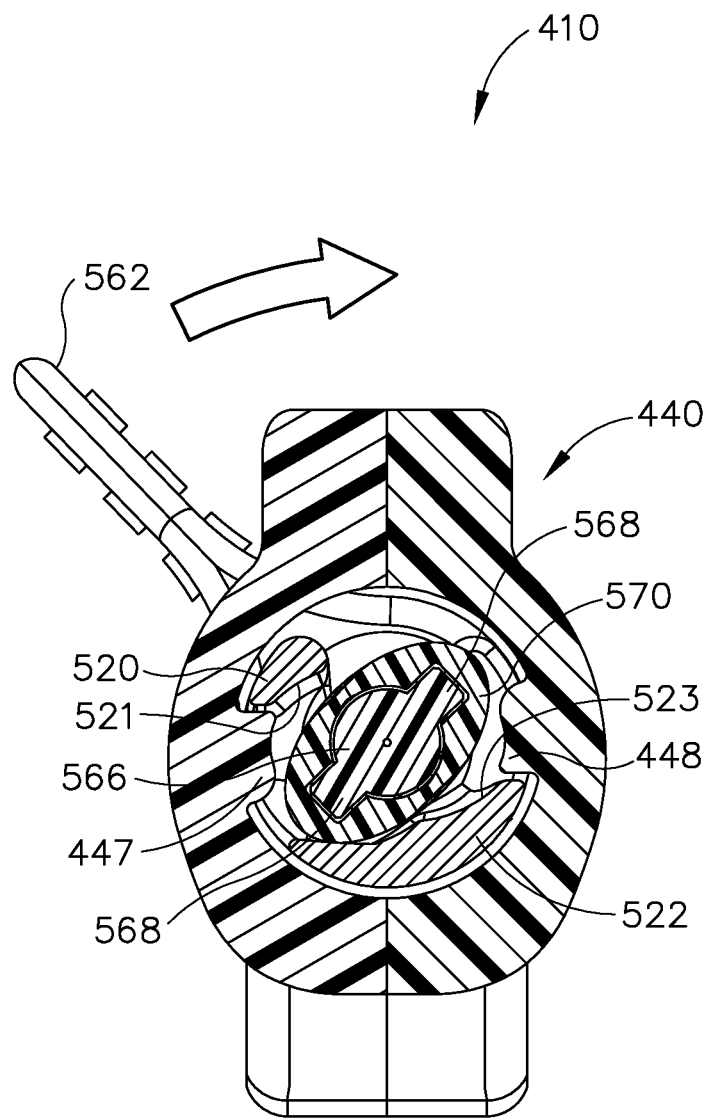
FIG. 25A depicts a front cross-sectional view of the instrument of FIG. 12, with the cam lock in a locked position.
Figure 25B:
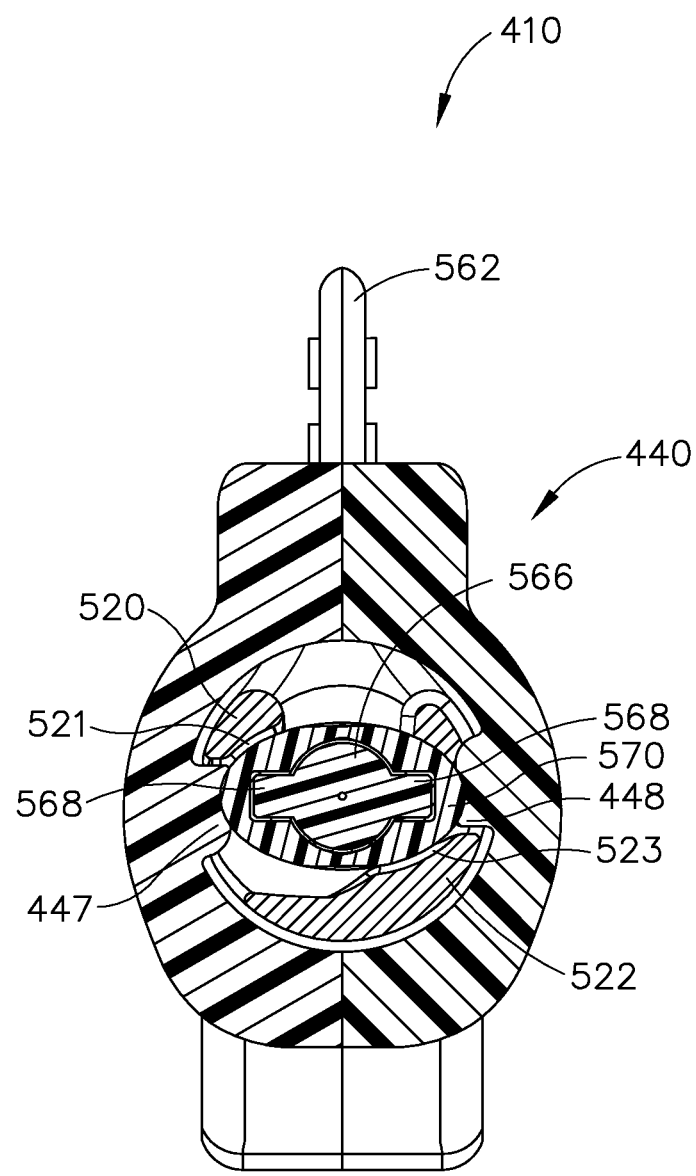
FIG. 25B depicts another front cross-sectional view of the instrument of FIG. 12, with the needle advancement member in an unlocked position.

FIGS. 24C and 25C show instrument (410) with cannula (420) in a fully advanced position. As can be seen, in the fully advanced position, cannula sled (510) has been fully advanced relative to body (440) via pinion gear (530) by an operator fully pivoting cannula advancement lever (540) distally. Although cannula (420) has been fully advanced distally, it should be understood that in this position needle (430) still remains disposed within cannula (420). In particular, needle (430) is maintained within cannula (420) by lock tab (569) of needle advancement member (560). As will be described in greater detail below, lock tab (569) of needle advancement member (560) prevents needle advancement member (560) from being advanced relative to cannula sled (510) until an operator rotates needle advancement member (560) to permit engagement of lock tab (569) with lower receiving channel (529) of cannula sled (510).

Once cannula (420) has been fully advanced distally, an operator may initiate the process for advancing needle (430). As can be seen in FIGS. 23C, 24C, 25A, and 26A, needle advancement member (560) is initially positioned at a rotational angle relative to body (440). To initiate advancement of needle (430), an operator may rotate needle advancement member (560) in a counter clockwise direction to a vertical position shown in FIGS. 23D, 24D, 25B, and 26B. When needle advancement member (560) is rotated to the vertical position, cannula sled (510) is locked in position relative to body (440). In particular, as can best be seen in FIG. 25B, cam lock (570) rotates as needle advancement member (560) is rotated. As cam lock (570) rotates, the elliptical configuration of cam lock (570) engages camming surfaces (521, 523) of cannula sled (510) to maintain the position of cannula sled (510) relative to cam lock (570). Cam lock (570) further engages a pair of lock protrusions (447, 448) integral to the interior of body (440). Lock protrusions (447, 448) engage cam lock (570) such that the position of cam lock (570) is longitudinally fixed relative to body (440), thereby locking cannula sled (510).

Figure 26A:
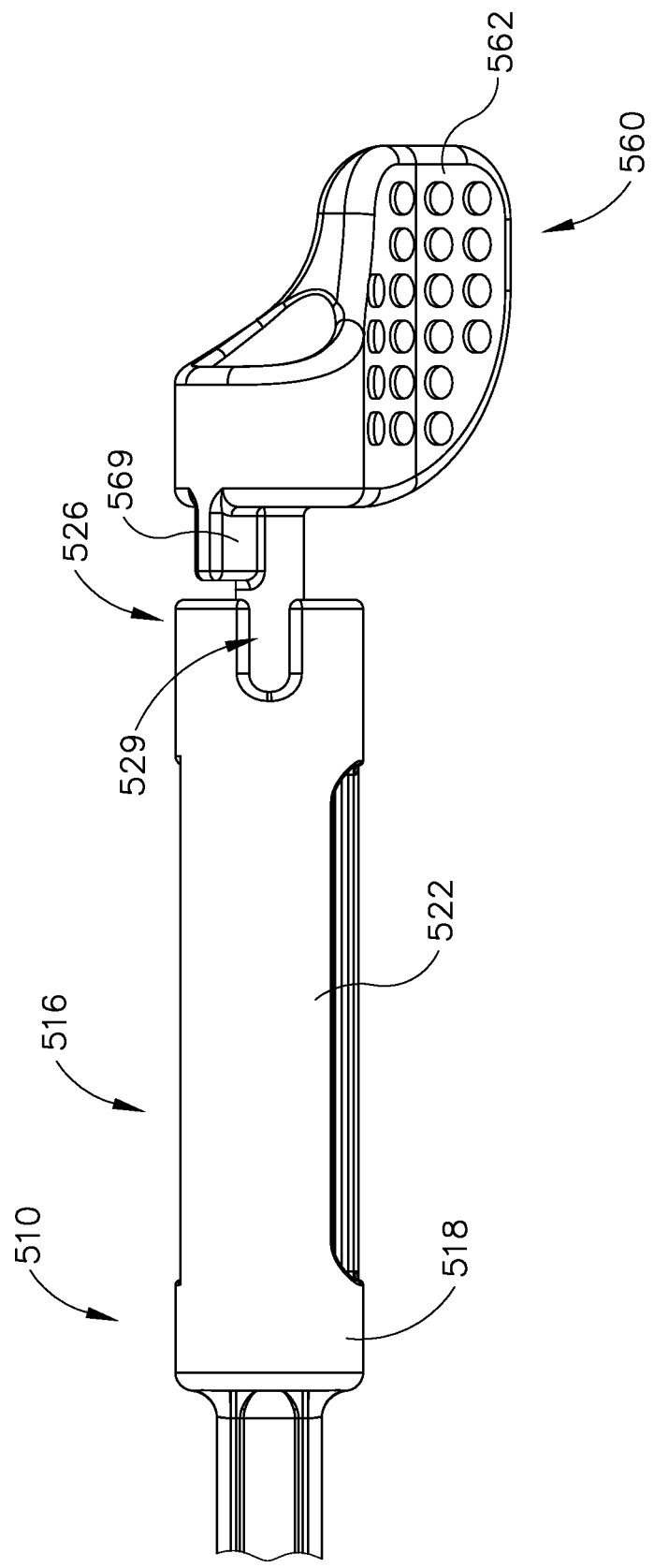
FIG. 26A depicts a partial bottom plan view of the cannula sled and the needle advancement member, with the needle advancement member in a locked and retracted position.
Figure 26B:
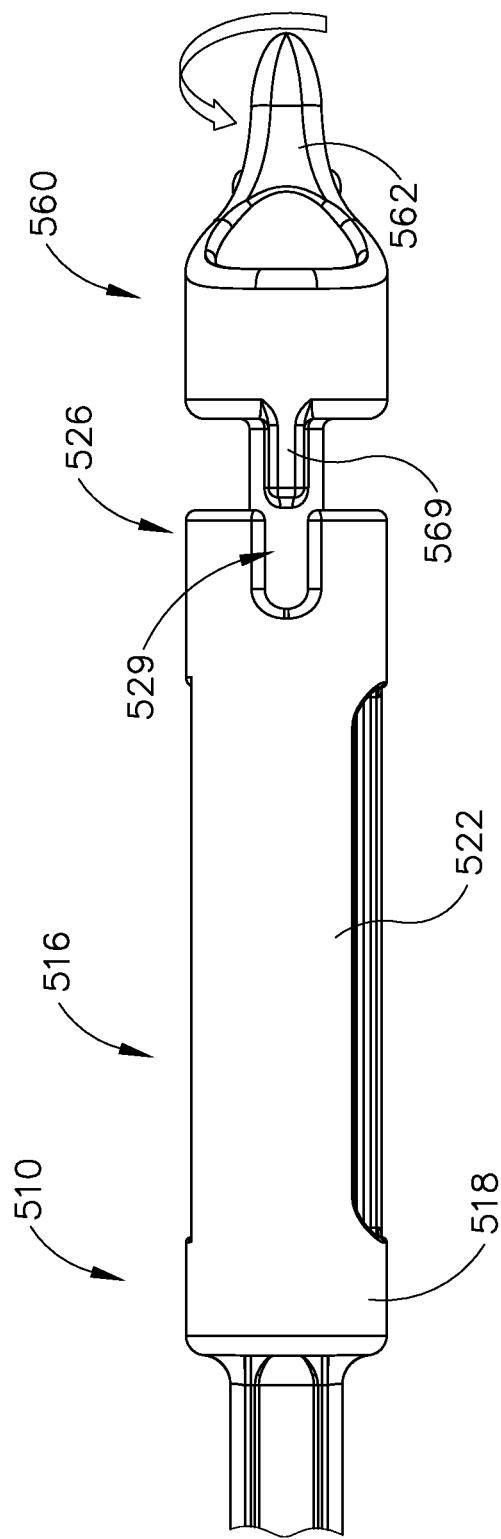
FIG. 26B depicts another partial bottom plan view of the cannula sled and the needle advancement member, with the needle advancement member in an unlocked and retracted position.
Figure 26C:
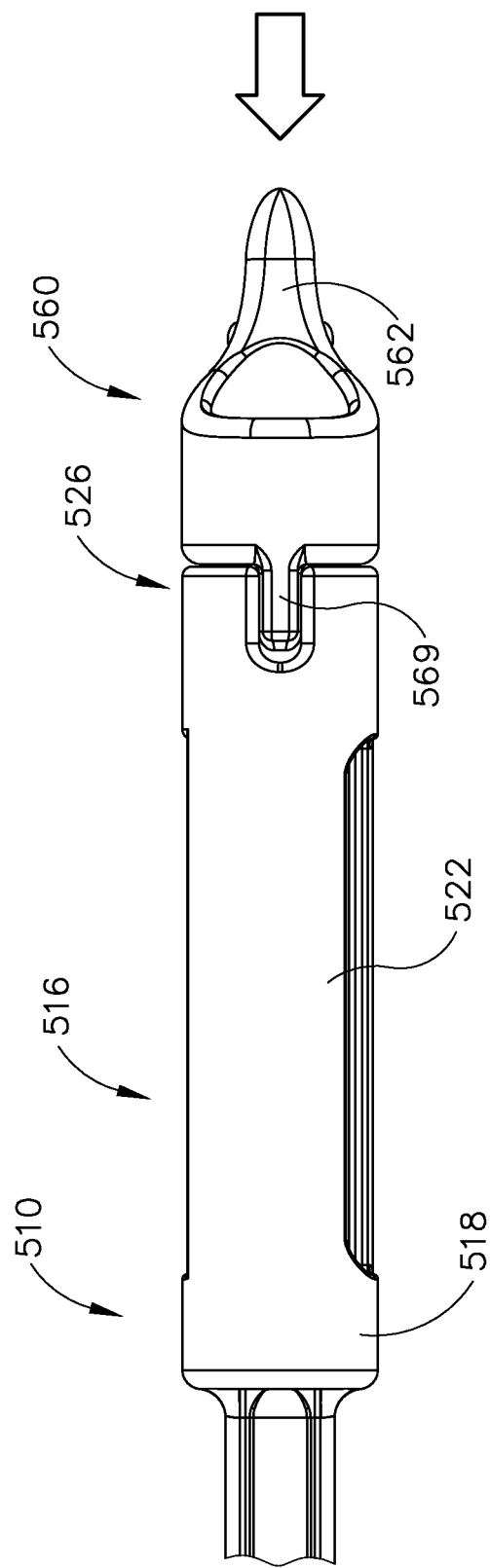
FIG. 26C depicts still another partial bottom plan view of the cannula sled and the needle advancement member, with the needle advancement member in an unlocked and advanced position.
Figure 27:
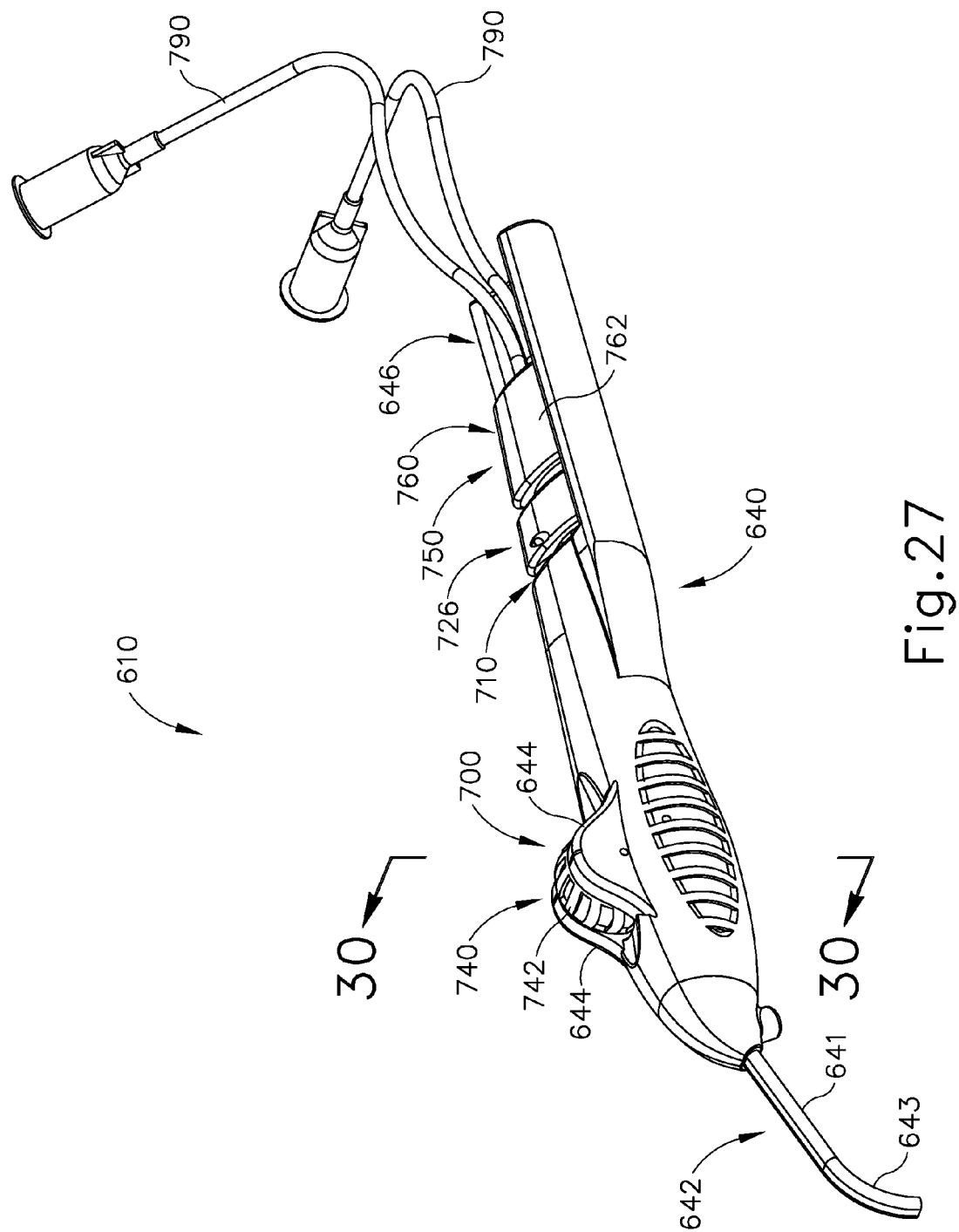
FIG. 27 depicts a perspective view of another exemplary alternative instrument for subretinal administration of a therapeutic agent from a suprachoroidal approach.

Rotation of needle advancement member (560) to the vertical position also aligns lock tab (569) of needle advancement member (560) with lower receiving channel (529) of cannula sled (510), as can best be seen in FIG. 26B. With lock tab (569) and lower receiving channel (529) aligned, an operator may then translate needle advancement member (560) distally to a distal position shown in FIGS. 23E, 24E, and 26C. As needle advancement member (560) is advanced distally, needle (430) correspondingly advances. Because cannula sled (510) is now fixed relative to needle advancement member (560), advancement of needle advancement member (560) will cause needle (430) to advance relative to cannula (420) such that the distal tip of needle (430) extends outwardly from cannula (420). A therapeutic agent may then be delivered as described above with respect to the method for suprachoroidal delivery of therapeutic agent. It should be understood that, when needle advancement member (560) is in the angular position shown in FIG. 26A, lock tab (569) may engage the proximal end of a needle advancement member receiving portion (526), thereby preventing needle advancement member (560) from being advanced distally relative to lock portion (516).

B. Exemplary Alternative Instrument with Scroll Wheel Actuator

FIGS. 27-31D show an exemplary alternative instrument (610) that is similar to instruments (10, 410) described above. It should be understood that instrument (610) may be readily used in place of instruments (10, 410) to perform the medical procedure described above. It should also be understood that except as otherwise described herein, instrument (610) of this example is substantially the same as instruments (10, 410) described above. Instrument (610) comprises a cannula (620), a body (640), a cannula guide (642) extending distally from body (640), a cannula actuation assembly (700) and a needle actuation assembly (750). Unlike instrument (10) described above, instrument (610) is generally configured to selectively advance both cannula (620) and a needle (630) relative to body (640). Cannula (620) and needle (630) are substantially the same as cannula (20) and needle (30) described above, such that further details will not be described herein.

Body (640) is generally shaped for grasping by the hand of an operator and to enclose the various components of cannula actuation assembly (700) and needle actuation assembly (750). To permit operation of cannula actuation assembly (700), body (640) includes two wheel supports (644) positioned near the distal end of body (640). Similarly, to permit operation of needle actuation assembly (750), body (640) includes a single actuator opening (646) defined proximally in body (640). As will be described in greater detail below, supports (644) and opening (646) permit movement of various components of cannula actuation assembly (700) and needle actuation assembly (750) such that an operator may actuate such components to thereby advance cannula (620) and/or needle (630).

As described above, cannula guide (642) extends distally from body (640). In particular, cannula guide (642) includes a relatively straight proximal portion (641) and a generally curved distal portion (643). Proximal portion (641) extends distally from body (640) obliquely relative to the longitudinal axis of body (640). Distal portion (643) is shown as curving away from the longitudinal axis of body (640) at an increasing angle. It should be understood that the combination of proximal and distal portions (641, 643) is configured to orient cannula guide (642) at or near sclerotomy (316) or suture loop assembly (330) described above. Accordingly, as will be described in greater detail below, cannula guide (642) is operable to feed cannula (620) into a suitable position as cannula (620) is advanced distally relative to instrument. Although cannula guide (642) is shown and described as having a particular shape herein, it should be understood that in other examples cannula guide (642) may have any other suitable shape as will be apparent to those of ordinary skill in the art in view of the teachings herein.

Cannula guide (642) generally has a cross-sectional shape corresponding to the shape of cannula (620). For instance, as described above, cannula (620) has a generally rectangular cross-sectional shape. Accordingly, cannula guide (642) may also have a corresponding rectangular cross-sectional shape. Cannula guide (642) is generally hollow, or otherwise includes a lumen (not shown) such that cannula guide (642) is configured to slidably receive cannula (620). In addition to having a shape corresponding to cannula (620), cannula guide (642) also includes rounded edges such that cannula guide (620) is atraumatic in nature.

In the present example, cannula guide (642) is comprised of a generally rigid or semi-rigid material such that cannula guide (642) may maintain its shape as cannula (620) is advanced through cannula guide (642). Because cannula guide (642) is atraumatic and rigid or semi-rigid, it should be understood that when instrument is used in the method for suprachoroidal delivery of therapeutic agent described above, cannula guide (642) may be optionally rested or gently pressed against a patient's eye to generate leverage and to help ensure tangential advancement of cannula (620).

Figure 28:
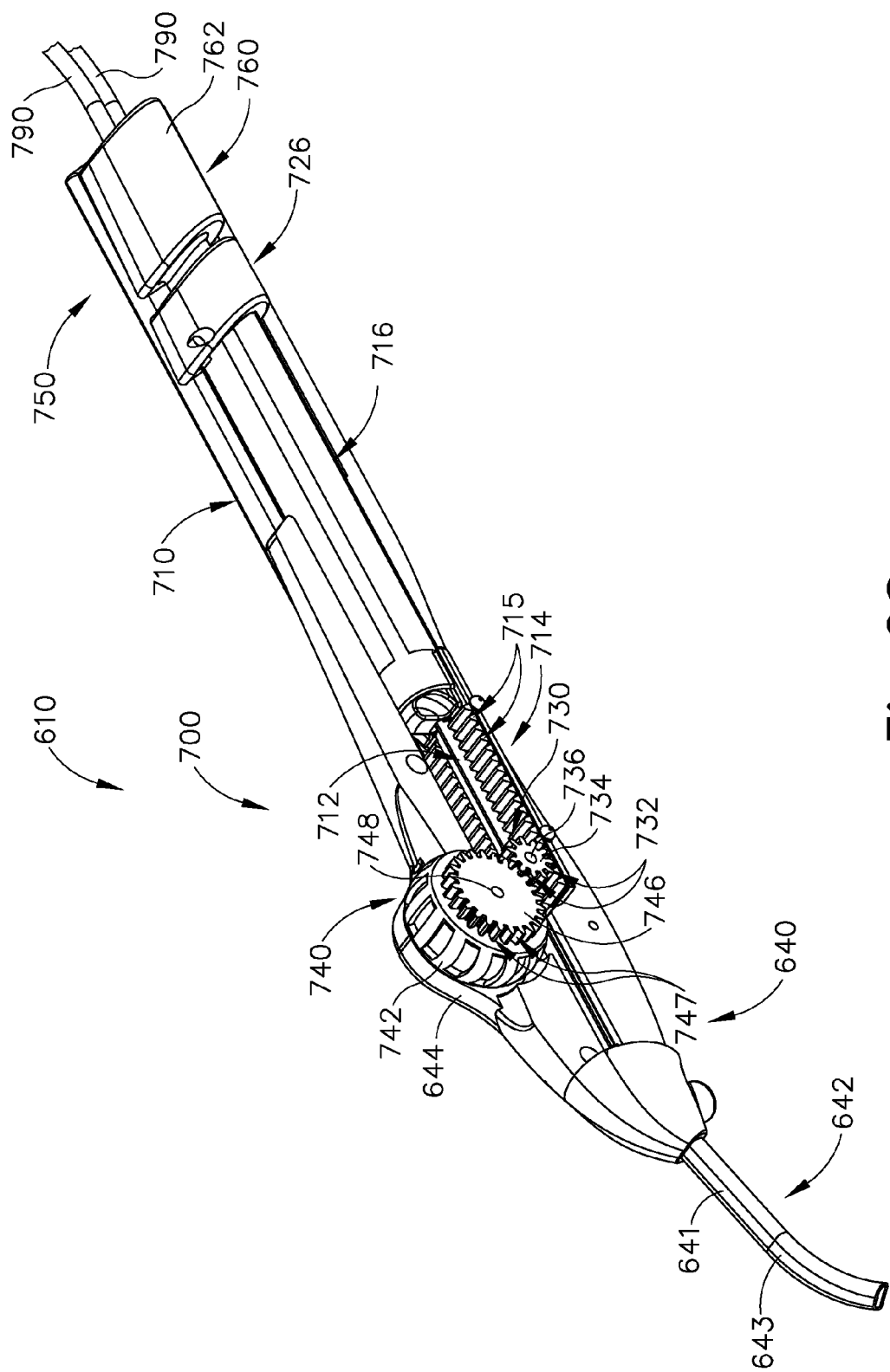
FIG. 28 depicts another perspective view of the instrument of FIG. 27, with a portion of a body removed.
Figure 29:
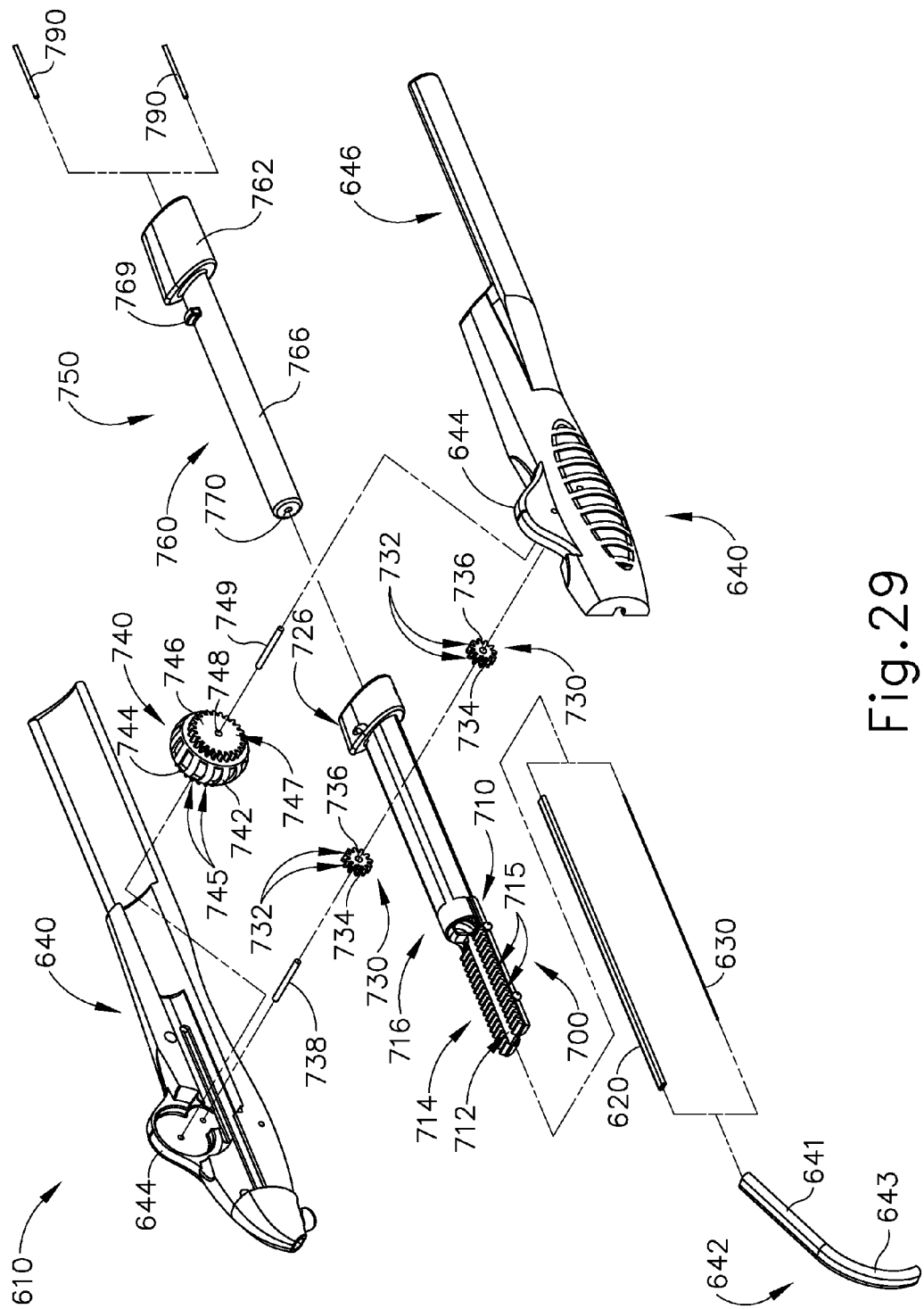
FIG. 29 depicts an exploded perspective view of the instrument of FIG. 27.
Figure 30:
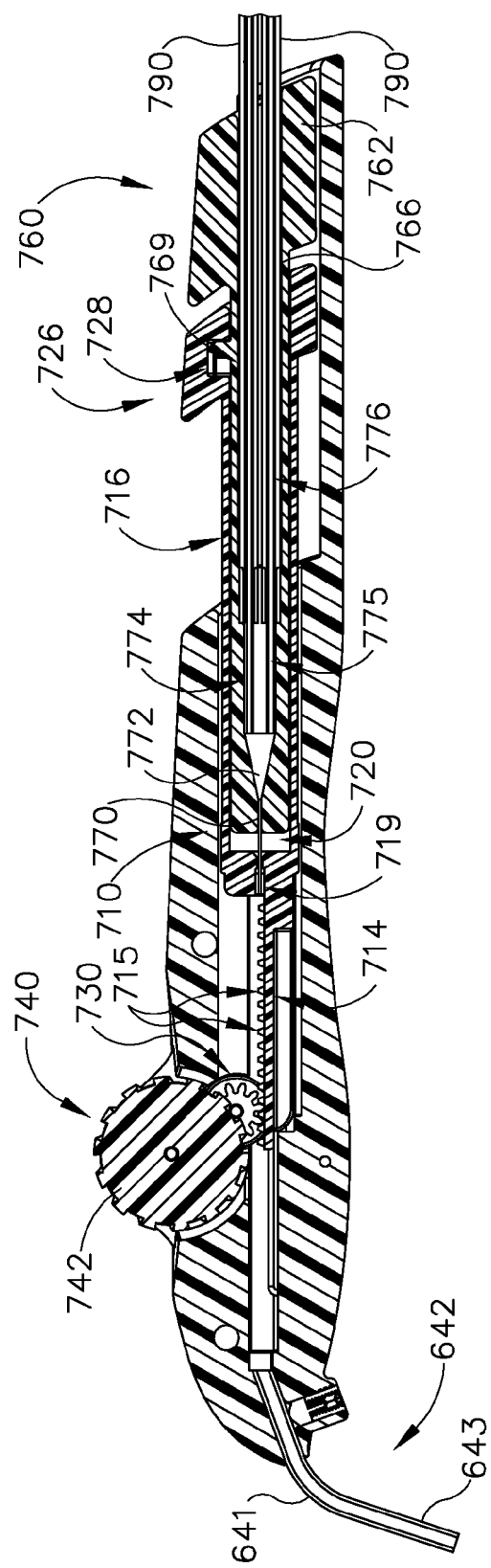
FIG. 30 depicts a cross-sectional view of the instrument of FIG. 27, with the cross-section taken along line 30-30 of FIG. 27.

FIGS. 28-30 show cannula actuation assembly (700) and needle actuation assembly (750) in detail. In particular, cannula actuation assembly (700) and needle actuation assembly (750) can be seen fully assembled in FIG. 28, where one half of body (740) is removed. As can be seen, cannula actuation assembly (700) includes a cannula sled (710), a pair of pinion gears (730), and a cannula advancement wheel (740). Needle actuation assembly (750) includes a needle advancement member (760) at least partially disposed within cannula sled (710). As will be described in greater detail below, cannula actuation assembly (700) is actuated by an operator rotating cannula advancement wheel (740) forward (e.g., in the counter clockwise direction) thereby causing cannula (620) and needle (630) to advance distally relative to body (640). Needle (630) is then advanced separately from cannula (620) by an operator advancing needle advancement member (760) distally relative to body (640).

FIG. 29 shows cannula actuation assembly (700) in detail and the relationship of cannula actuation assembly (700) to the rest of instrument (610). As will be described in greater detail below, cannula actuation assembly (700) is actuated via cannula advancement wheel (740), which rotates to drive pinion gears (730). Pinion gears (730) then engage cannula sled (710) to translate cannula sled (710) relative to body (640).

FIGS. 29 and 30 show detailed views of cannula sled (710). As can be seen, cannula sled (710) comprises a cannula channel (712), a rack portion (714), an elongate portion (716), and a needle advancement member receiving portion (726). Cannula channel (712) is configured to receive cannula (620) and is disposed within at least a portion of rack portion (714). As can best be seen in FIG. 30, cannula channel (712) terminates in a needle lumen (719), which extends through cannula sled (710). Cannula (620) may be fixedly secured within cannula channel (712) by any suitable means such as adhesive boding, welding, mechanical fastening, etc. Additionally, it should be understood that cannula channel (712) may include additional structural features configured to receive cannula (620). By way of example only, in some examples the proximal end of cannula (620) may include a flange or other similar structure, while cannula channel (712) may include a corresponding channel to further secure cannula (620) within cannula channel (712). Of course, other means of securing cannula (620) within cannula channel (712) will be apparent to those of ordinary skill in the art in view of the teachings herein.

Rack portion (714) comprises a plurality of teeth (715) that are spaced apart from each other along a linear, longitudinally extending path. A distal region of teeth (715) is separated into two laterally spaced apart regions, spaced apart by cannula channel (712). The particular size and spacing of teeth (715) corresponds to teeth (732) of pinion gears (730). Accordingly, teeth (715) of rack portion (714) are configured to mesh with teeth (732) of each pinion gear (730) to form a rack and pinion mechanism. As will be described in greater detail below, such a mechanism drives translation of cannula sled (710) to actuate cannula (620).

Elongate portion (716) of cannula sled (710) is generally cylindrical and extends between rack portion (714) and needle advancement member receiving portion (726). As can best be seen in FIG. 30, elongate portion (716) defines a bore (720) extending through elongate portion (716) and needle advancement member receiving portion (726). Bore (720) is configured to slidably receive needle advancement member (760) such that needle advancement member (760) may be selectively translated relative to cannula sled (710). The distal end of bore (720) is in communication with needle lumen (719) such that needle (630) may extend from needle advancement member (760) through needle lumen (719).

Needle advancement member receiving portion (726) is positioned proximally of elongate portion (716). Needle advancement member receiving portion (726) is generally cylindrical in shape having a larger radius than that of elongate member (716). As described above, bore (720) of elongate portion (716) extends through needle advancement member receiving portion (726). As best seen in FIG. 30, the interior of needle advancement member receiving portion (726) includes an upper receiving channel (728). As will be described in greater detail below, upper receiving channel (728) is configured to receive a corresponding tab (769) of needle advancement member (760). The longitudinal length of upper receiving channel (728) corresponds to the travel distance of needle advancement member (760). As will be understood, tab (769) of needle advancement member (760) translates within upper receiving channel (728) as needle advancement member (760) is translated relative to cannula sled (710) to advance needle (630). Translation of needle advancement member (760) is permitted until tab (769) of needle advancement member (760) reaches the distal end of upper receiving channel (728). Thus, it should be understood that upper receiving channel (728) may act as a stop for needle advancement member (760) to prevent needle (630) from being advanced beyond a certain distance.

Returning to FIG. 29, each pinion gear (730) is shown as comprising a generally cylindrical body (734) with a plurality of teeth (732) extending outwardly therefrom. Body (734) of each pinion gear (730) further includes a bore (736) extending therethrough. Bore (736) is configured to receive pinion gear pin (738). As will be described in greater detail below, pinion gear pin (738) is received within bore (736) to rotatably couple pinion gear (730) to body (640) of instrument (610).

Cannula advancement wheel (740) is also shown in FIG. 29. As can be seen, wheel (740) comprises a grip portion (742) and two driver portions (744, 746) extending outwardly from grip portion (742). Each driver portion (744, 746) is circular in shape and comprises a respective set of teeth (745, 747). Teeth (745, 747) are configured to engage teeth (732) of each pinion gear (730) such that teeth (745, 747) may drive rotation of each pinion gear (730) in unison. Cannula advancement wheel (740) further includes a bore (748) extending therethrough. Bore (748) is configured to receive a wheel pin (749) to rotatably couple wheel (740) to body (640) of instrument (610).

FIGS. 28-30 show needle actuation assembly (750) in detail and the relationship of needle actuation assembly (750) to the rest of instrument (610). As will be described in greater detail below, needle actuation assembly (750) is generally configured to translate with cannula actuation assembly (700) until cannula actuation assembly (700) is locked in place by needle actuation assembly (750) thereby permitting needle (630) to be advanced relative to cannula (620). As described above, needle actuation assembly (750) comprises needle advancement member (760) and two supply tubes (790) extending proximally from the proximal end of needle advancement member (760). As can be seen, needle advancement member (760) comprises an actuation portion (762) and an elongate cylindrical portion (766) extending therefrom. Actuation portion (762) is generally cylindrical in shape and is configured for grasping by an operator. Although actuation portion (762) of the present example is shown as having a cylindrical shape, it should be understood that in other examples actuation portion (762) may take on any other shape suitable for grasping. As will be described in greater detail below, actuation member (762) receives supply tubes (790) such that supply tubes (790) may be in communication with needle (730).

As can best be seen in FIG. 29, elongate cylindrical portion (766) includes a tab (769) extending outwardly from elongate cylindrical portion (766). As was described above, tab (769) is configured to fit within upper receiving channel (728) of cannula sled (710) to thereby permit limited slidability of needle advancement member (760) relative to cannula sled (710). It should be understood that "limited slidability" in this context refers to restriction of the movement of tab (769) in the longitudinal direction by upper receiving channel (728) such that needle advancement member (760) may translate relative to cannula sled (710) a certain predetermined distance. In the transverse or rotational direction, tab (769) is relatively fixed by upper receiving channel (728) such that transverse or rotational movement of tab (769) relative to upper receiving channel (728) is minimized. In other words, tab (769) and upper receiving channel (728) act cooperatively such that needle advancement member (760) may translate a predetermined distance relative to cannula sled (710); while needle advancement member (760) is prevented from rotating relative to cannula sled (710).

Elongate cylindrical portion (766) further comprises a lumen (770) extending at least partially through elongate cylindrical portion (766) from the distal end of elongate cylindrical portion (766). Lumen (770) is configured to receive needle (430) and it should be understood that in some examples lumen (770) may include needle securing features such as channels, ports for adhesives, etc. As can best be seen in FIG. 30, lumen (770) extends proximally through elongate cylindrical portion (766) until lumen (770) intersects with a conical mixing chamber (772). In particular, in the present example needle advancement member (760) is configured to accommodate two supply tubes (790). Accordingly, conical mixing chamber (772) is positioned between supply tubes (790) and lumen (770) to ensure proper flow and/or mixing of fluid expelled from supply tubes (790). It should be understood that mixing chamber (772) is entirely optional and may be omitted in some examples. For instance, in some examples needle advancement member (760) may be equipped with a single supply tube (790), thus eliminating the need for mixing chamber (772). It should also be understood that it is not necessary for two or more fluid components to be mixed in mixing chamber (772), such that chamber (772) may simply serve as a multi-input intake manifold for needle (630). For instance, chamber (772) may selectively receive leading bleb (340) followed by therapeutic agent (341) during a medical procedure as described above.

Supply tubes (790) are connected to mixing chamber (772) by two tube lumens (774, 775) extending proximally from mixing chamber (772). Tube lumens (774, 775) are configured to fixedly secure supply tubes (790) within elongate cylindrical portion (766). In some examples this may be accomplished by an interference fit between tube lumens (774, 775) and supply tubes (790). In other examples, supply tubes (790) may be fixedly secured by any other suitable means such as adhesive bonding, mechanical fastening, etc. Tube lumens (774, 775) extend proximally within elongate cylindrical portion (766) until tube lumens (774, 775) intersect with a tube bore (776). Tube bore (776) extends to through elongate cylindrical portion (766) and actuation portion (762) to the proximal end of needle advancement member (760) and permits supply tubes (790) to freely move about within tube bore (776). Although tube lumens (774, 775) are shown as only extending partially through elongate cylindrical portion (766) it should be understood that in other examples tube lumens (774, 775) may extend through elongate cylindrical portion (766) in place of tube bore (776).

FIGS. 31A-31D show an exemplary mode of operation using instrument (610). In particular, instrument (610) begins in the state shown in FIG. 31A. As can be seen, cannula actuation assembly (700) and needle actuation assembly (750) are initially both in a retracted proximal position relative to body (640). In this position, cannula advancement wheel (740) is rotated to its furthest counter clockwise position. Correspondingly, cannula sled (710) has been driven proximally to its proximal most position within body (640). Because cannula (620) is fixedly secured to cannula sled (710), cannula (620) is similarly disposed proximally relative to body (640) such that cannula (620) is disposed within cannula guide (642). In this position, needle (630) is also in a proximal position such that the distal tip of needle (630) is disposed within cannula (642).

Figure 31A:
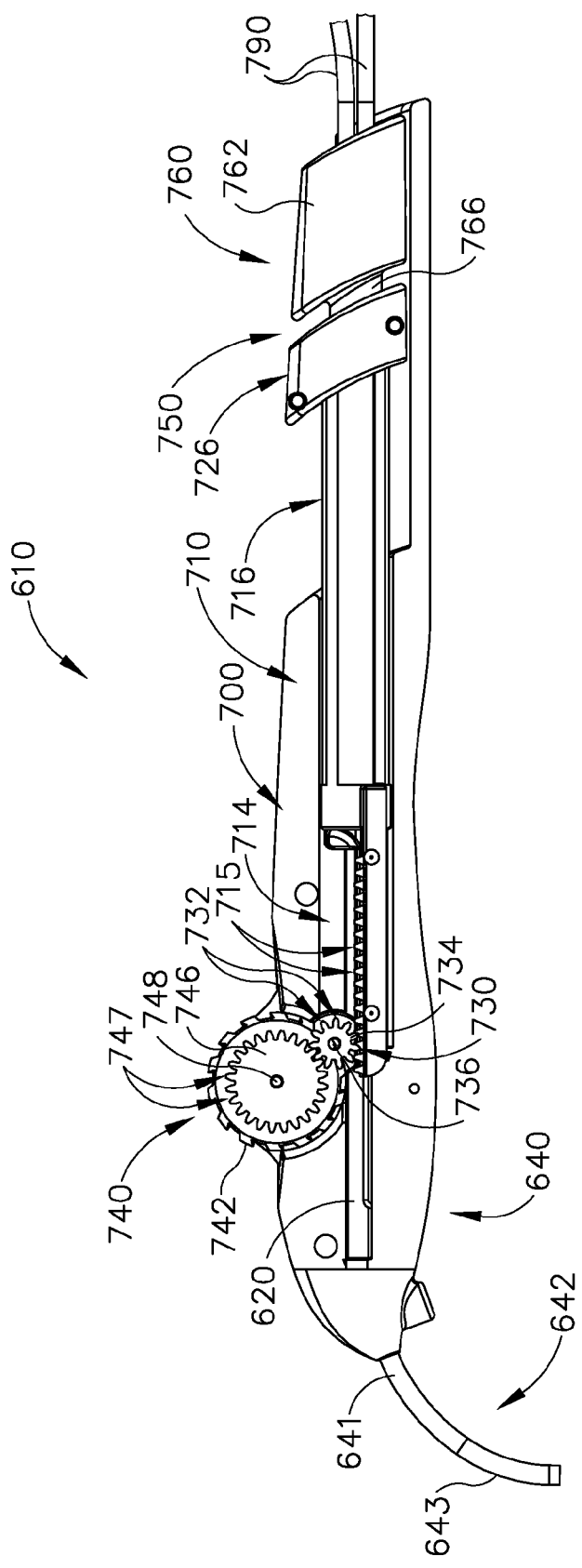
FIG. 31A depicts a side elevational view of the instrument of FIG. 27, with a portion of the body removed and a cannula and needle in a retracted position.
Figure 31B:
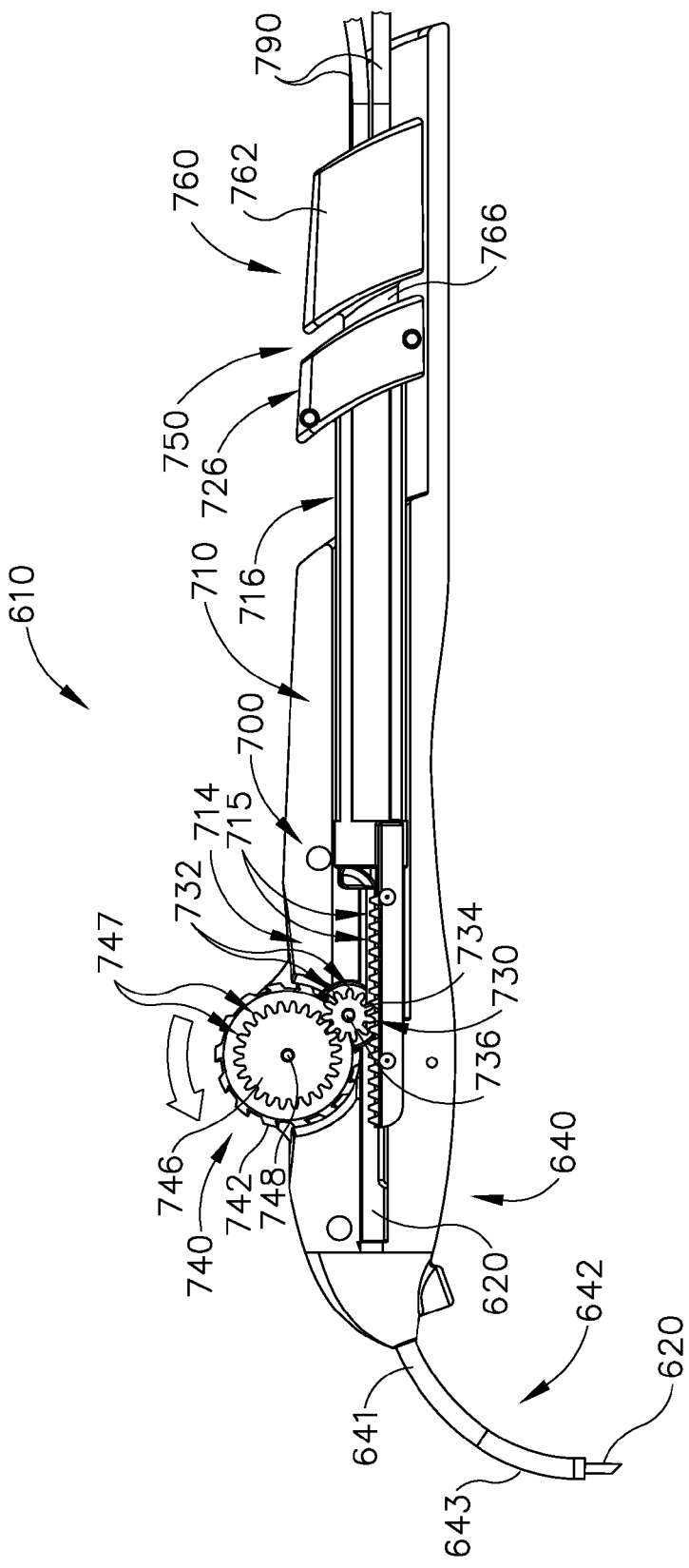
FIG. 31B depicts another side elevational view of the instrument of FIG. 27, with the cannula in a partially advanced position and the needle in a retracted position.

To initiate advancement of cannula (620), an operator may apply a force to cannula advancement wheel (740) to rotate cannula advancement wheel (740) in a counter clockwise direction relative to body (640), as can be seen in FIG. 31B. Because teeth (732) of pinion gears (730) are engaged with teeth (745, 747) of cannula advancement wheel (740), rotation of cannula advancement wheel (740) will cause pinion gears (730) to correspondingly rotate in a clockwise direction. As pinion gears (730) rotate in a clockwise direction, teeth (732) of pinion gears (730) will engage teeth (715) of cannula sled (710) to translate cannula sled (710) distally. Thus, counter clockwise rotational movement of cannula advancement wheel (740) will initiate distal translation of cannula sled (710) via pinion gears (730). Because cannula (620) is fixedly secured to cannula sled (710), advancement of cannula sled (710) will result in corresponding advancement of cannula (620). As cannula sled (710) is advanced, needle advancement assembly (750) is also correspondingly advanced due to engagement between tab (769) of needle advancement member (760) and upper receiving channel (728) of cannula sled (710).

Figure 31C:
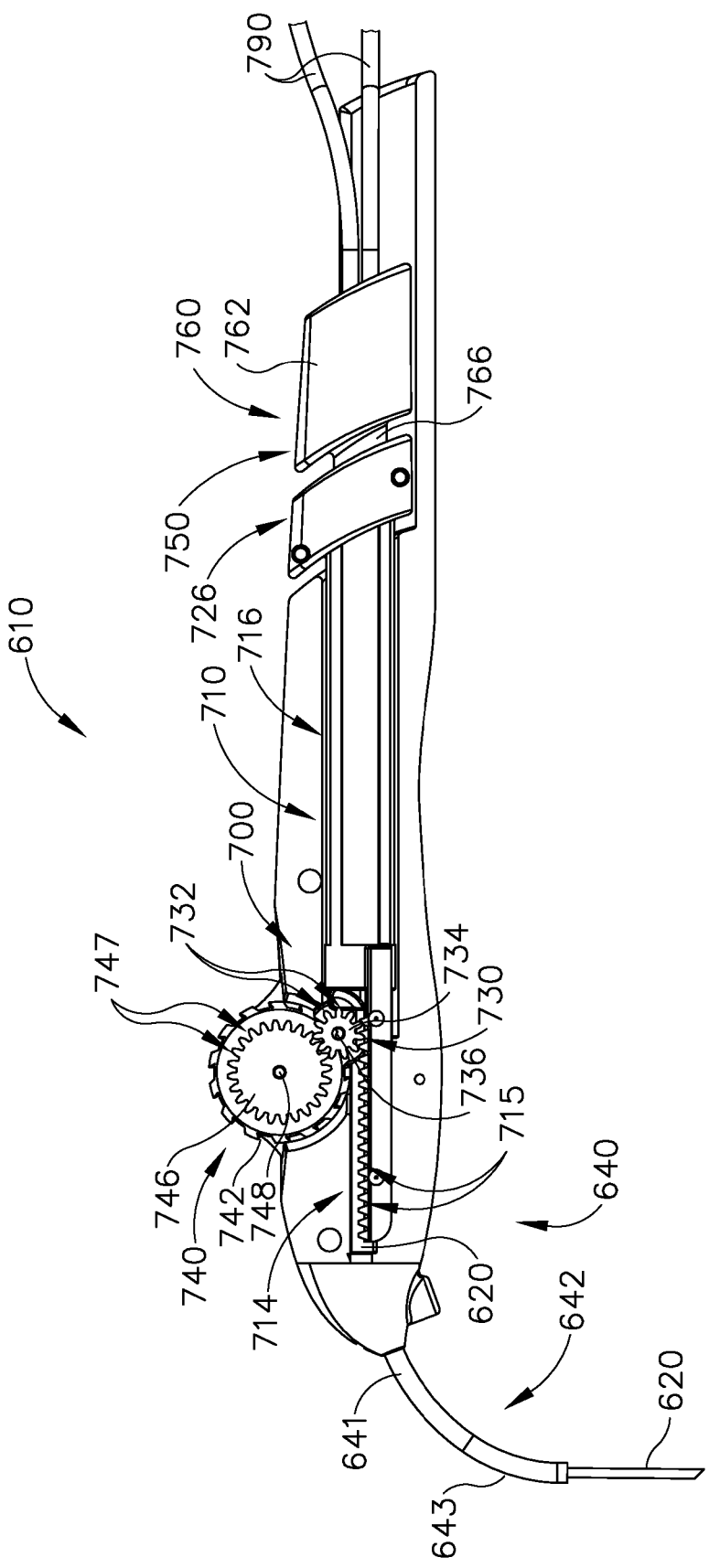
FIG. 31C depicts still another side elevational view of the instrument of FIG. 27, with the cannula in a fully advanced position and the needle in a retracted position.
Figure 31D:
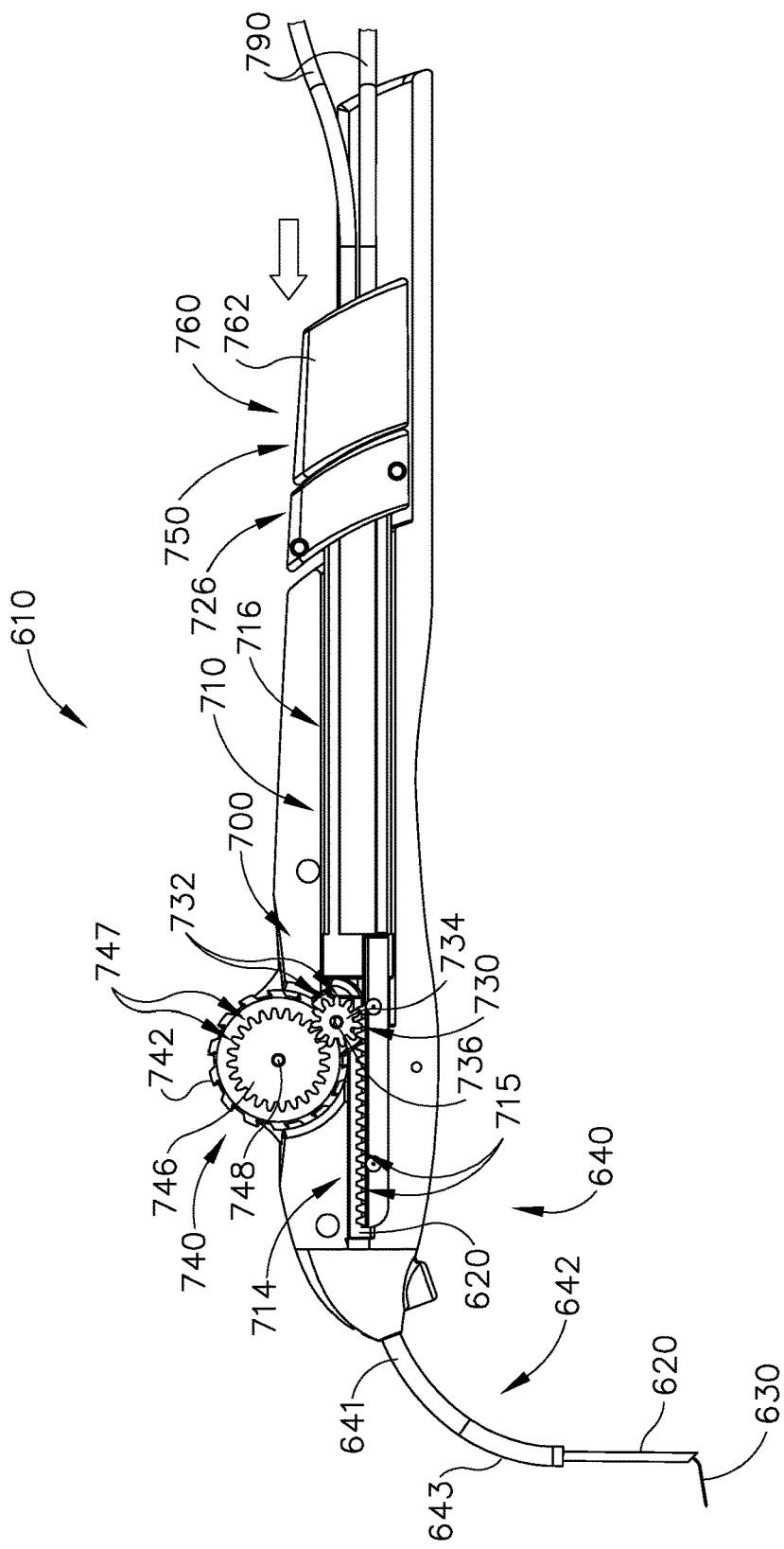
FIG. 31D depicts yet another side elevational view of the instrument of FIG. 27, with the cannula in a fully advanced position and the needle in an advanced position.

FIG. 31C shows instrument (610) with cannula (620) in a fully advanced position. As can be seen, in the fully advanced position, cannula sled (710) has been fully advanced relative to body (640) via pinion gears (730) by an operator fully rotating cannula advancement wheel (740). Although cannula (620) has been fully advanced distally, it should be understood that in this position needle (630) still remains disposed within cannula (620) until an operator forces needle advancement member (760) distally to translate needle advancement member (760) relative to cannula sled (710).

Once cannula (620) has been fully advanced distally, an operator may initiate the process for advancing needle (630). As can be seen in FIG. 31C, needle advancement member (760) is initially positioned such that there is at least some clearance between needle advancement member receiving portion (726) of cannula sled (710) and actuation portion (762) of needle advancement member (760). Although not shown, it should be understood that in some examples, such a clearance may be maintained with a removable member disposed between needle advancement member receiving portion (726) of cannula sled (710) and actuation portion (762) of needle advancement member (760). When instrument (610) is equipped with such a removable member, such a removable member will be removed prior to initiation of needle (630) advancement. To initiate advancement of needle (630) in the present example, an operator may grasp needle advancement member (760) and translate needle advancement member (760) relative to cannula sled until needle (630) is positioned in a desired position relative to cannula (620). Alternatively, an operator may translate needle advancement member (760) until tab (769) of needle advancement member (760) contacts the distal end of upper receiving channel (728) of cannula sled (710) thereby preventing further translation of needle advancement member (760) relative to cannula sled (710). A therapeutic agent may then be delivered as described above with respect to the method for suprachoroidal delivery of therapeutic agent.

C. Exemplary Alternative Instrument with Lock Collet

Figure 32A:
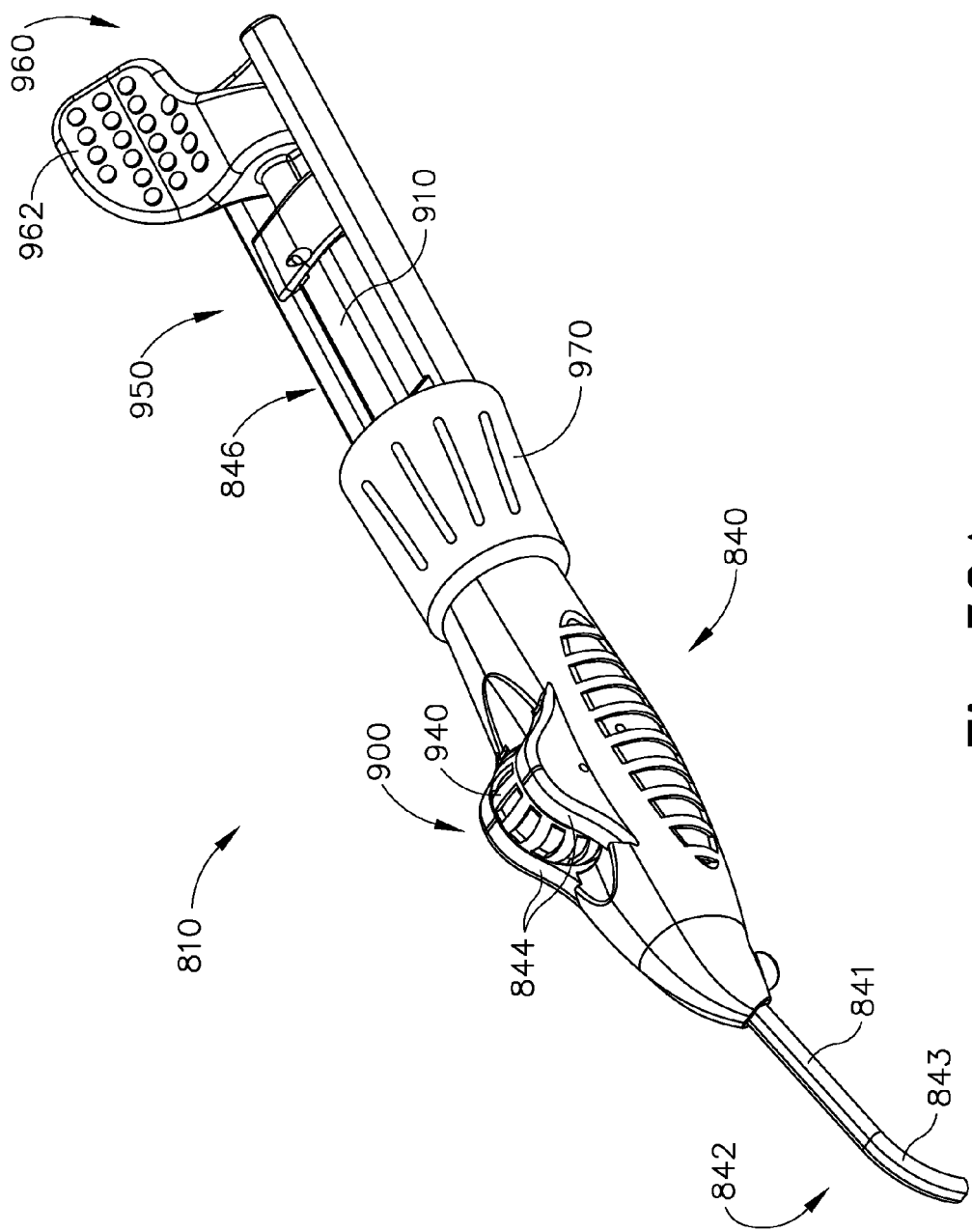
FIG. 32A depicts a perspective view of another exemplary alternative instrument for subretinal administration of therapeutic agent from a suprachoroidal approach.
Figure 32B:
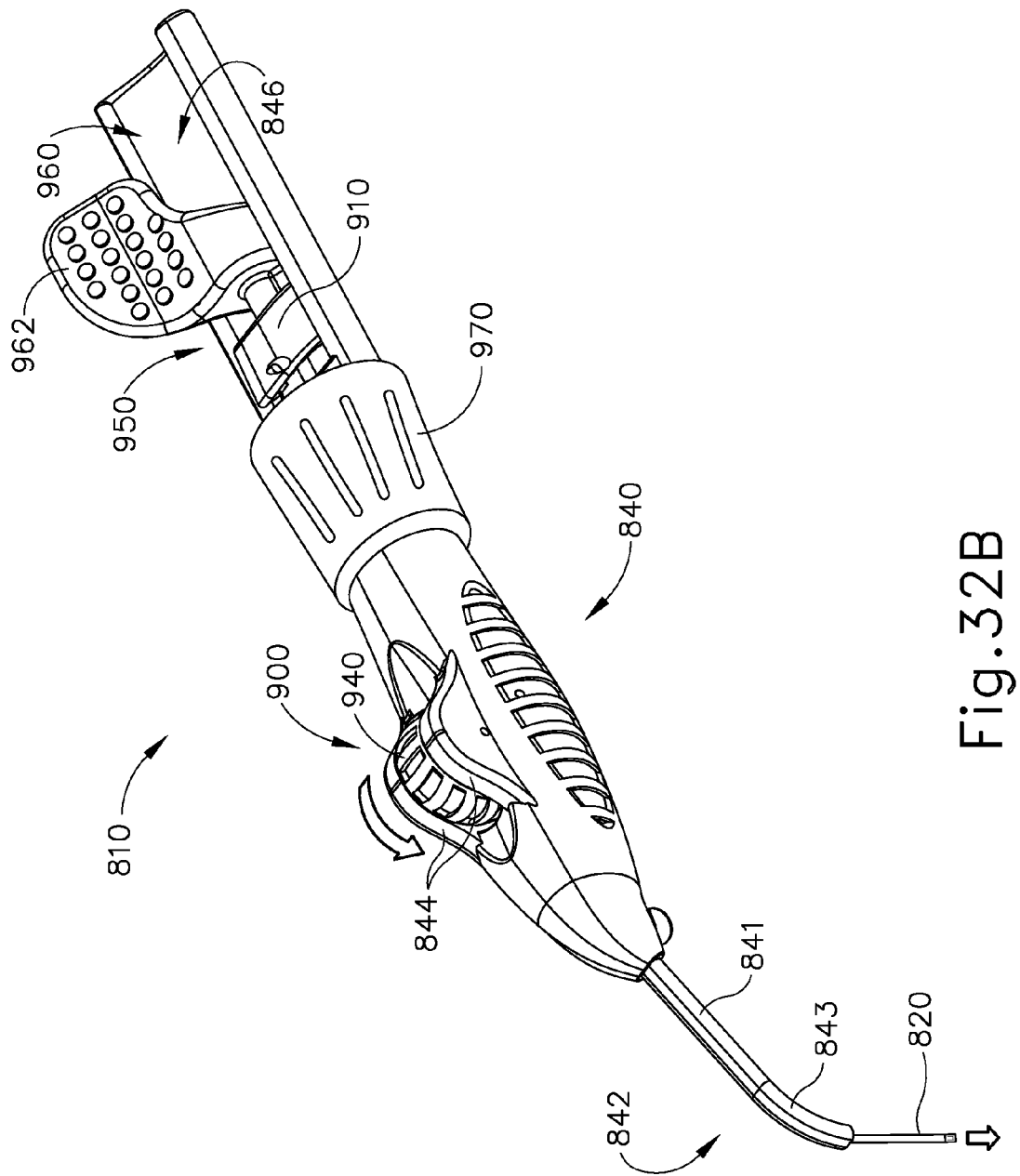
FIG. 32B depicts another perspective view of the instrument of FIG. 32A, with a cannula in an advanced position and a needle in a retracted and locked position.
Figure 32C:
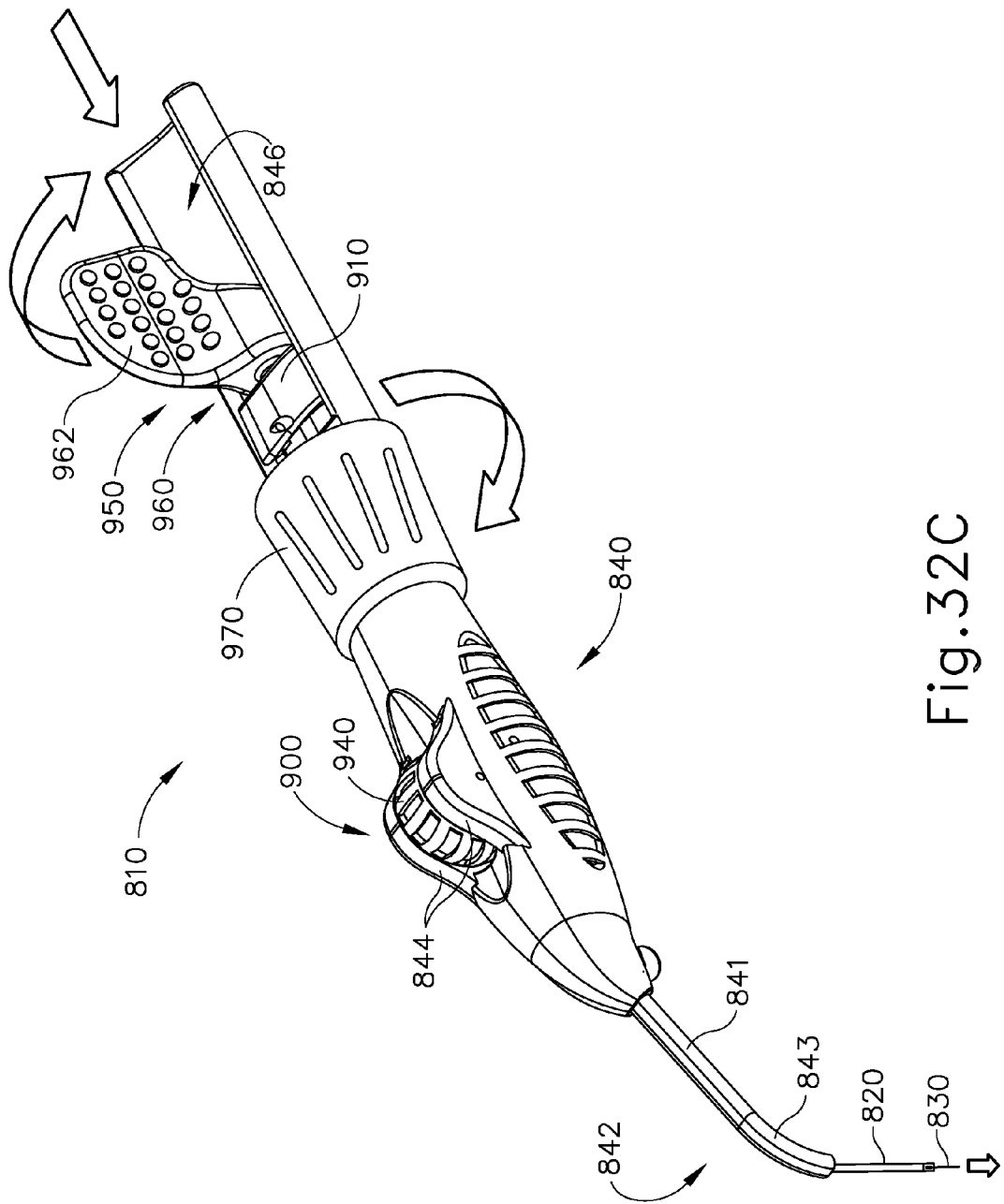
FIG. 32C depicts still another perspective view of the instrument of FIG. 32A, with the cannula in an advanced position and the needle in an unlocked and advanced position.

FIGS. 32A-32C show an exemplary alternative instrument (810) that is similar to instruments (410, 610) described above. It should be understood that instrument (810) may be readily used in place of instruments (10, 410, 610) to perform the medical procedure described above. It should also be understood that except as otherwise described herein, instrument (810) of this example is substantially the same as instruments (10, 410, 610) described above. Instrument (810) comprises a cannula (820) (FIG. 32B), a body (840), a cannula guide (842) extending distally from body (840), a cannula actuation assembly (900), and a needle actuation assembly (950). Unlike instrument (10) described above, instrument (810) is generally configured to selectively advance both cannula (820) and a needle (830) (FIG. 32C) relative to body (840). Cannula (820) and needle (830) are substantially the same as cannula (20) and needle (30) described above, such that further details will not be described herein.

Body (840) is generally shaped for grasping by the hand of an operator and to enclose the various components of cannula actuation assembly (900) and needle actuation assembly (950). To permit operation of cannula actuation assembly (900), body (840) includes two wheel supports (844) positioned near the distal end of body (840). Similarly, to permit operation of needle actuation assembly (950), body (840) includes a single actuator opening (846) defined proximally in body (840). As will be described in greater detail below, supports (844) and opening (846) permit movement of various components of cannula actuation assembly (900) and needle actuation assembly (850) such that an operator may actuate such components to thereby advance cannula (820) and/or needle (830).

As described above, cannula guide (842) extends distally from body (840). In particular, cannula guide (842) includes a relatively straight proximal portion (841) and a generally curved distal portion (843). Proximal portion (841) extends distally from body (840) obliquely relative to the longitudinal axis of body (840). Distal portion (843) is shown as curving away from the longitudinal axis of body (840) at an increasing angle. It should be understood that the combination of proximal and distal portions (841, 843) is configured to orient cannula guide (842) at or near sclerotomy (316) or suture loop assembly (330) described above. Accordingly, as will be described in greater detail below, cannula guide (842) is operable to feed cannula (820) into a suitable position as cannula (820) is advanced distally relative to instrument. Although cannula guide (842) is shown and described as having a particular shape herein, it should be understood that in other examples cannula guide (842) may have any other suitable shape as will be apparent to those of ordinary skill in the art in view of the teachings herein.

Cannula guide (842) generally has a cross-sectional shape corresponding to the shape of cannula (820). For instance, as described above, cannula (820) has a generally rectangular cross-sectional shape. Accordingly, cannula guide (842) may also have a corresponding rectangular cross-sectional shape. Cannula guide (842) is generally hollow, or otherwise includes a lumen (not shown) such that cannula guide (842) is configured to slidably receive cannula (820). In addition to having a shape corresponding to cannula (820), cannula guide (842) also includes rounded edges such that cannula guide (820) is atraumatic in nature.

In the present example, cannula guide (842) is comprised of a generally rigid or semi-rigid material such that cannula guide (842) may maintain its shape as cannula (820) is advanced through cannula guide (842). Because cannula guide (842) is atraumatic and rigid or semi-rigid, it should be understood that when instrument is used in the method for suprachoroidal delivery of therapeutic agent described above, cannula guide (842) may be optionally rested or gently pressed against a patient's eye to generate leverage and to help ensure tangential advancement of cannula (820).

Cannula actuation assembly (900) of the present example is substantially the same as cannula actuation assembly (700) described above. For instance, cannula actuation assembly (900) includes a cannula sled (910), a pair of pinion gears (not shown), and a cannula advancement wheel (940). Cannula actuation assembly (900) of the present example operates similarly to cannula actuation assembly (700) with wheel (940) being rotatable to drive pinion gears (not shown), which in turn drive cannula sled (910) to thereby advance cannula (820) relative to body (840).

Needle actuation assembly (950) is similar to needle actuation assembly (550) described above, except needle actuation assembly (950) of the present example includes a different locking mechanism. As can be seen, needle actuation assembly (950) includes a needle advancement member (960) at least partially disposed within cannula sled (910). Needle advancement member (960) is substantially the same as needle advancement member (560) described above. For instance, like with needle advancement member (560), needle advancement member (960) of the present example includes an actuation tab (962) that is substantially the same as actuation tab (562) described above. As will be described in greater detail below, in some examples actuation tab (962) may be used to rotate needle advancement member (960) to a vertical position thereby unlocking translation of needle advancement member (960) relative to cannula sled (910).

Unlike needle actuation assembly (550) described above, needle actuation assembly (950) of the present example lacks a member similar to cam lock (570) described above. Instead, needle actuation assembly (950) includes a lock collet (970) disposed about body (840). Lock collet (970) is configured to engage cannula sled (910) of cannula actuation assembly (900) to selectively lock and unlock translational movement of cannula sled (910). As will be described in greater detail below, lock collet (970) is configured such that rotation of lock collet (970) relative to body (840) will cause lock collet (970) to shift between a locked and unlocked state.

FIGS. 32A-32C show an exemplary mode of operation using instrument (810). In particular, instrument (810) begins in the state shown in FIG. 32A. As can be seen, cannula actuation assembly (900) and needle actuation assembly (950) are initially both in a retracted proximal position relative to body (840). In this position, cannula advancement wheel (940) is rotated to its furthest counter clockwise position. Correspondingly, cannula sled (910) has been driven proximally to its proximal most position within body (840). Because cannula (820) is fixedly secured to cannula sled (910), cannula (820) is similarly disposed proximally relative to body (840) such that cannula (820) is disposed within cannula guide (842). In this position, needle (830) is also in a proximal position such that the distal tip of needle (830) is disposed within cannula (842).

To initiate advancement of cannula (820), an operator may first rotate lock collet (970) of needle actuation assembly (950) if lock collet (970) is in the locked state. If lock collet (970) is in the unlocked state, an operator may alternatively immediately begin advancement of cannula (820) without first moving lock collet (970) to the unlocked state. An operator may advance cannula (820) by applying a force to cannula advancement wheel (940) to rotate cannula advancement wheel (940) in a counter clockwise direction relative to body (840), as can be seen in FIG. 32B. Because teeth (not shown) of pinion gears are engaged with teeth (not shown) of cannula advancement wheel (940), rotation of cannula advancement wheel (940) will cause pinion gears to correspondingly rotate in a clockwise direction. As pinion gears rotate in a clockwise direction, the teeth of pinion gears will engage the teeth of cannula sled (910) to translate cannula sled (910) distally. Thus, counter clockwise rotational movement of cannula advancement wheel (940) will initiate distal translation of cannula sled (910) via pinion gears. Because cannula (820) is fixedly secured to cannula sled (910), advancement of cannula sled (910) will result in corresponding advancement of cannula (820). As cannula sled (910) is advanced, needle advancement assembly (950) may also correspondingly advance due to incidental friction between the parts of needle advancement member (960) and cannula sled (910).

FIG. 32B shows instrument (810) with cannula (820) in a fully advanced position. In the fully advanced position, cannula sled (910) has been fully advanced relative to body (840) via pinion gears by an operator fully rotating cannula advancement wheel (940). Although cannula (820) has been fully advanced distally, it should be understood that at this stage needle (830) still remains disposed within cannula (820) until an operator forces needle advancement member (960) distally to translate needle advancement member (960) relative to cannula sled (910).

Once cannula (820) has been fully advanced distally, the operator may initiate the process for advancing needle (830). As can be seen in FIG. 32C, needle advancement member (960) is initially positioned such that there is at least some clearance between cannula sled (910) and needle advancement member (960). Although not shown, it should be understood that in some examples, such a clearance may be maintained with a removable member disposed between cannula sled (910) and needle advancement member (960). When instrument (810) is equipped with such a removable member, such a removable member will be removed prior to initiation of needle (830) advancement. Alternatively, needle advancement member (960) and cannula sled (910) may include features such as a lock tab and corresponding channel similar to lock tab (569) of needle advancement member (560) and lower receiving channel (529) of cannula sled (510) described above with respect to instrument (410). As was described above, if needle advancement member (960) is equipped with such a feature, needle advancement member (960) is rotated to a vertical position prior to advancement of needle (830) (as shown in FIG. 32C). Once any unlocking step is completed by an operator, the operator may next lock cannula sled (910) in place by rotating lock collet (970). Next, needle (830) may be advanced by the operator grasping needle advancement member (960) and translating needle advancement member (960) distally relative to cannula sled (910) until needle (830) is positioned in a desired position relative to cannula (820). A therapeutic agent may then be delivered as described above with respect to the method for suprachoroidal delivery of therapeutic agent.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus for delivering therapeutic agent to an eye, wherein the apparatus comprises: (a) a body; (b) a cannula movable relative to the body, wherein the cannula is sized and configured to be insertable between a choroid and a sclera of a patient's eye, wherein the cannula defines a longitudinal axis; (c) a hollow needle, wherein the needle is slidable relative to the cannula; (d) a cannula actuation assembly, wherein the cannula actuation assembly is operable to actuate the cannula relative to the body; and (e) a needle actuation assembly, wherein the needle actuation assembly is operable to actuate the needle relative to the cannula.

Example 2

The apparatus of Example 1, wherein the cannula actuation assembly and the needle actuation assembly are operable independent of each other.

Example 3

The apparatus of any one or more of Examples 1 through 2, wherein the needle actuation assembly is responsive to actuation of the cannula relative to the body.

Example 4

The apparatus of Example 3, wherein the needle actuation assembly is configured to actuate the needle relative to the body as the cannula actuation assembly actuates the cannula relative to the body.

Example 5

The apparatus of any one or more of Examples 1 through 4, further comprising a lock feature, wherein the lock feature is operable to transition between a first state and a second state, wherein the lock feature is operable to lock the cannula actuation assembly to thereby prevent actuation of the cannula relative to the body when the lock feature is in the second state.

Example 6

The apparatus of Example 5, wherein the lock feature is operable to lock the needle actuation assembly to thereby prevent actuation of the needle relative to the cannula when the lock feature is in the first state.

Example 7

The apparatus of Example 6, wherein the lock feature comprises a cam feature, wherein the cam feature has an elliptical cross-sectional shape, wherein the cam feature is rotatable to transition the lock feature between the first state and the second state.

Example 8

The apparatus of any one or more of Examples 1 through 7, wherein the cannula actuation assembly comprises a cannula member, wherein the cannula member is configured to translate relative to the body to actuate the cannula relative to the body.

Example 9

The apparatus of Example 8, wherein the cannula actuation assembly further comprises a rack and pinion assembly, wherein the rack and pinion assembly is in communication with the cannula member, wherein the rack and pinion assembly is configured to drive translation of the cannula member.

Example 10

The apparatus of any one or more of Examples 8 through 9, wherein the cannula member comprises a lumen extending from a distal end of the cannula member to a proximal end of the cannula member, wherein the lumen is configured to slidably receive the needle.

Example 11

The apparatus of any one or more of Examples 8 through 10, wherein the needle actuation assembly comprises a needle member, wherein at least a portion of the needle member is insertable within the cannula member.

Example 12

The apparatus of Example 11, wherein the needle member is configured to selectively translate relative to the cannula member.

Example 13

The apparatus of Example 12, wherein the needle actuation assembly further comprises an actuation selector, wherein the actuation selector is responsive to rotation of the needle member to simultaneously unlock translation of the needle member relative to the cannula member and lock translation of the cannula member relative to the body.

Example 14

The apparatus of any one or more of Examples 1 through 13, further comprising a cannula guide, wherein the cannula guide extends distally from the body, wherein the cannula guide is configured to direct the cannula along a predetermined path.

Example 15

The apparatus of Example 14, wherein the cannula guide comprises a lumen extending from a proximal end to a distal end of the cannula guide, wherein the lumen is configured to receive the cannula and direct the cannula along the predetermined path.

Example 16

An apparatus for delivering therapeutic agent to an eye, wherein the apparatus comprises: (a) a body; (b) a cannula, wherein the cannula is sized and configured to be insertable between a choroid and a sclera of a patient's eye, wherein the cannula comprises a needle lumen extending therethrough; (c) a hollow needle, wherein the needle is configured to slidably engage the needle lumen of the cannula; and (d) an actuation assembly, wherein the actuation assembly comprises: (i) a cannula actuator, and (ii) a needle actuator.

Example 17

The apparatus of Example 16, further comprising an actuation mechanism, wherein the actuation mechanism is configured to drive the cannula actuator distally relative to the body.

Example 18

The apparatus of Example 17, wherein the actuation mechanism comprises a wheel and a gear, wherein the wheel has a plurality of teeth, wherein the teeth are configured to engage a corresponding plurality of teeth of the gear, wherein the cannula actuator is in communication with the gear.

Example 19

A method of administering a therapeutic solution to an eye of a patient, the method comprising the steps of: (a) threading a suture through the eye of the patient to form at least one loop defined by the suture; (b) incising at least a portion of the eye to provide access to the choroid of the eye; (c) positioning an cannula guide of an instrument near the eye such that a distal end of the cannula guide is positioned adjacent to the at least one loop defined by the suture; (d) advancing a cannula through the at least one loop defined by the suture and into an incision created by incising at least a portion of the eye by advancing an actuator of the instrument; and (e) advancing a needle through the cannula to penetrate through the choroid and administer the therapeutic solution by advancing a second actuator of the instrument.

Example 20

The method of Example 19, wherein the method further comprises locking the cannula relative to the instrument prior to advancing the needle through the cannula using a locking feature of the instrument.

VII. MISCELLANEOUS

Although the procedures and devices described herein are discussed in the context of the treatment of age-related macular degeneration, it should be understood that no such limitation is intended or implied. The procedures and devices described herein may be used to treat various other kinds of medical conditions. By way of example only, the procedures and devices described herein (and variations thereof) may be used to treat retinitis pigmentosa, diabetic retinopathy, wet age-related macular degeneration, and/or other medical conditions. Various suitable medical contexts in which the procedures and devices described herein may be used will be apparent to those of ordinary skill in the art.

It should be understood that any of the versions of the instruments described herein may include various other features in addition to or in lieu of those described above. By way of example only, any of the devices herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for delivering therapeutic agent to an eye, wherein the apparatus comprises:
   (a) a body;
   (b) a cannula extending distally from the body, wherein the cannula is sized and configured to be insertable between a choroid and a sclera of a patient's eye, wherein the cannula defines a longitudinal axis;
   (c) a hollow needle having a proximal end, a sharp distal tip, and a needle lumen extending therebetween with a uniform inner diameter, wherein the needle is slidable within the cannula;
   (d) an actuation assembly, wherein the actuation assembly is operable to actuate the needle relative to the body, wherein the actuation assembly comprises:
      (i) a rotating member rotatably coupled with the body, and
      (ii) a translating member translatably coupled with the body such that a distal end of the translating member is housed within the body, wherein the translating member is operatively coupled with the rotating member and with the needle such that the proximal end of the needle extends directly from the distal end of the translating member, wherein the translating member is operable to actuate the needle relative to the body in response to rotation of the rotating member; and
   (e) a fluid path extending from a proximal end of the apparatus to a distal end of the needle, wherein a distal portion of the fluid path is defined by the needle lumen, wherein the fluid path is configured to communicate with a fluid source through the proximal end of the device to deliver therapeutic agent to an eye, wherein the apparatus is operable to deliver therapeutic agent distally along the fluid path independently of translation of the translating member.

2. The apparatus of claim 1, wherein the actuation assembly comprises a cannula actuation assembly and a needle actuation assembly, wherein the cannula actuation assembly includes the rotating member, wherein the needle actuation assembly includes the translating member.

3. The apparatus of claim 2, wherein the needle actuation assembly is responsive to actuation of the cannula relative to the body.

4. The apparatus of claim 3, wherein the needle actuation assembly is configured to actuate the needle relative to the body as the cannula actuation assembly actuates the cannula relative to the body.

5. The apparatus of claim 2, further comprising a lock feature, wherein the lock feature is operable to transition between a first state and a second state, wherein the lock feature is operable to lock the cannula actuation assembly to thereby prevent actuation of the cannula relative to the body when the lock feature is in the second state.

6. The apparatus of claim 5, wherein the lock feature is operable to lock the needle actuation assembly to thereby prevent actuation of the needle relative to the cannula when the lock feature is in the first state.

7. The apparatus of claim 6, wherein the lock feature comprises a cam feature, wherein the cam feature has an elliptical cross-sectional shape, wherein the cam feature is rotatable to transition the lock feature between the first state and the second state.

8. The apparatus of claim 2, wherein the cannula actuation assembly comprises a cannula member, wherein the cannula member is configured to translate relative to the body to actuate the cannula relative to the body.

9. The apparatus of claim 8, wherein the cannula actuation assembly further comprises a rack and pinion assembly, wherein the rack and pinion assembly is in communication with the cannula member, wherein the rack and pinion assembly is configured to drive translation of the cannula member.

10. The apparatus of claim 8, wherein the cannula member comprises a lumen extending from a distal end of the cannula member to a proximal end of the cannula member, wherein the lumen is configured to slidably receive the needle.

11. The apparatus of claim 8, wherein the needle actuation assembly includes the translating member, wherein at least a portion of the translating member is insertable within the cannula member.

12. The apparatus of claim 11, wherein the translating member is configured to selectively translate relative to the cannula member.

13. The apparatus of claim 12, wherein the needle actuation assembly further comprises an actuation selector, wherein the actuation selector is responsive to rotation of the translating member to simultaneously unlock translation of the translating member relative to the cannula member and lock translation of the cannula member relative to the body.

14. The apparatus of claim 1, further comprising a cannula guide, wherein the cannula guide extends distally from the body, wherein the cannula guide is configured to direct the cannula along a predetermined path.

15. The apparatus of claim 14, wherein the cannula guide comprises a lumen extending from a proximal end to a distal end of the cannula guide, wherein the lumen is configured to receive the cannula and direct the cannula along the predetermined path.

16. The apparatus of claim 1, wherein the actuation assembly further comprises:
(i) a projection affixed to the translating member, and
(ii) a channel defined by a channel wall, wherein the projection is slidably disposed within the channel, wherein the channel wall is movable relative to the body to engage the projection and drive the translating member relative to the body to thereby actuate the needle relative to the body in response to rotation of the rotating member.

17. An apparatus for delivering therapeutic agent to an eye, wherein the apparatus comprises:
(a) a body;
(b) a cannula, wherein the cannula is sized and configured to be insertable between a choroid and a sclera of a patient's eye, wherein the cannula comprises a cannula lumen extending therethrough;
(c) a hollow needle, wherein the needle is slidably disposed within the cannula lumen; and
(d) an actuation assembly, wherein the actuation assembly is operable to actuate the needle relative to the body, wherein the actuation assembly comprises:
(i) a rotating member rotatably coupled with the body,
(ii) a translating member translatably coupled with the body, wherein the translating member is operatively coupled with the rotating member and with the needle,
(iii) a projection affixed to the translating member, and
(iv) a movable structure operatively coupled with the body, wherein the movable structure includes a channel,
wherein the projection is slidably disposed within the channel, wherein the movable structure is movable relative to the body to engage the projection and drive the translating member relative to the body to thereby actuate the needle relative to the body in response to rotation of the rotating member.

18. The apparatus of claim 17, wherein the rotating member is operable to drive the translating member distally when rotated in a first direction, wherein the rotating member is operable to drive the translating member proximally when rotated in a second direction.

19. The apparatus of claim 18, wherein the rotating member comprises a wheel, wherein the actuation assembly further comprises a gear, wherein the wheel has a plurality of teeth, wherein the teeth are configured to engage a corresponding plurality of teeth of the gear, wherein the translating member is engaged with the gear.

20. An apparatus for delivering therapeutic agent to an eye, wherein the apparatus comprises:
(a) a body;
(b) a guide extending distally from the body;
(c) a cannula slidably disposed within the guide, wherein the cannula is sized and configured to be insertable between a choroid and a sclera of a patient's eye;
(d) a hollow needle slidably disposed within the cannula; and
(e) an actuation assembly, wherein the actuation assembly comprises:
(i) a rotating member rotatably coupled with the body,
(ii) a first translating member translatably coupled with the body, wherein the cannula is fixed axially relative to the first translating member, and
(iii) a second translating member moveably coupled with the first translating member, wherein the needle is fixed axially relative to the second actuating member,
wherein the first and second translating members are operable to translate together relative to the body in response to rotation of the rotating member to thereby actuate the cannula and the needle relative to the body,
wherein the second actuating member is movable relative to the first actuating member to actuate the needle relative to the cannula.

* * * * *